(12) United States Patent
Huang et al.

(10) Patent No.: US 10,028,728 B2
(45) Date of Patent: Jul. 24, 2018

(54) ULTRASOUND WAVEFORM TOMOGRAPHY WITH SPATIAL AND EDGE REGULARIZATION

(71) Applicant: LOS ALAMOS NATIONAL SECURITY, LLC, Los Alamos, NM (US)

(72) Inventors: Lianjie Huang, Los Alamos, NM (US); Youzuo Lin, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 864 days.

(21) Appl. No.: 14/339,738

(22) Filed: Jul. 24, 2014

(65) Prior Publication Data

US 2014/0364736 A1    Dec. 11, 2014

Related U.S. Application Data

(63) Continuation of application No. PCT/US2013/024662, filed on Feb. 4, 2013.
(Continued)

(51) Int. Cl.
*A61B 8/08* (2006.01)
*A61B 8/13* (2006.01)
(Continued)

(52) U.S. Cl.
CPC .......... *A61B 8/5207* (2013.01); *A61B 5/0073* (2013.01); *A61B 5/7275* (2013.01);
(Continued)

(58) Field of Classification Search
None
See application file for complete search history.

(56) References Cited

U.S. PATENT DOCUMENTS

| 4,075,883 A | 2/1978 | Glover |
| 4,582,065 A | 4/1986 | Adams |

(Continued)

FOREIGN PATENT DOCUMENTS

| JP | 2009189867 A | 8/2009 |
| KR | 1020100075011 A | 7/2010 |

(Continued)

OTHER PUBLICATIONS

Sallard et al. "Use of a priori Information for the Deconvolution of Ultrasonic Signals", Rev. of Prog. in Quantitative Nondestructive Evaluation, vol. 17 Plenum Press, New York, 1998 pp. 735-742.*
Sumi, C. ("Spatially variant regularization for tissue strain measurement and shear modulus reconstruction" J Med Ultrasonics (2007) 34:125-131, Mar. 8, 2007).*
Tai et al. "Image Denoising Using TV-Stokes Equation with an Orientation-Matching Minimization" Space and Variational Methods in Computer Vision. Lecture Notes in Computer Science, vol. 5567. 2009 pp. 1-12.*
(Continued)

*Primary Examiner* — Amanda Lauritzen Moher
*Assistant Examiner* — Farouk Bruce
(74) *Attorney, Agent, or Firm* — Lewis Roca Rothgerber Christie LLP

(57) ABSTRACT

Synthetic-aperture ultrasound tomography systems and methods using scanning arrays and algorithms configured to simultaneously acquire ultrasound transmission and reflection data, and process the data for improved ultrasound tomography imaging, wherein the tomography imaging comprises total-variation regularization, or a modified total variation regularization, particularly with edge-guided or spatially variant regularization.

12 Claims, 37 Drawing Sheets

Related U.S. Application Data

(60) Provisional application No. 61/594,865, filed on Feb. 3, 2012.

(51) Int. Cl.

| | | |
|---|---|---|
| *A61B 8/00* | (2006.01) | |
| *A61B 8/14* | (2006.01) | |
| *A61B 8/15* | (2006.01) | |
| *G01S 15/89* | (2006.01) | |
| *A61B 5/00* | (2006.01) | |
| *G06T 5/00* | (2006.01) | |
| *G06T 11/00* | (2006.01) | |

(52) U.S. Cl.
CPC ............ *A61B 8/085* (2013.01); *A61B 8/0825* (2013.01); *A61B 8/13* (2013.01); *A61B 8/14* (2013.01); *A61B 8/145* (2013.01); *A61B 8/15* (2013.01); *A61B 8/406* (2013.01); *A61B 8/4477* (2013.01); *A61B 8/4488* (2013.01); *A61B 8/4494* (2013.01); *A61B 8/483* (2013.01); *G01S 15/8915* (2013.01); *G01S 15/8929* (2013.01); *G01S 15/8997* (2013.01); *G06T 5/001* (2013.01); *G06T 11/005* (2013.01)

(56) References Cited

U.S. PATENT DOCUMENTS

| | | | |
|---|---|---|---|
| 5,465,722 A * | 11/1995 | Fort | G01H 5/00 600/437 |
| 5,908,390 A | 6/1999 | Matsushima | |
| 6,186,951 B1 | 2/2001 | Lizzi et al. | |
| 2001/0020130 A1 | 9/2001 | Gee et al. | |
| 2002/0099290 A1 | 7/2002 | Haddad | |
| 2002/0173722 A1 | 11/2002 | Hoctor | |
| 2003/0158481 A1 | 8/2003 | Stotzka | |
| 2004/0034307 A1* | 2/2004 | Johnson | A61B 5/05 600/459 |
| 2006/0009696 A1* | 1/2006 | Hanover | A61B 5/415 600/437 |
| 2006/0058678 A1 | 3/2006 | Vitek | |
| 2006/0173304 A1 | 8/2006 | Wang | |
| 2006/0184020 A1 | 8/2006 | Sumi | |
| 2006/0293597 A1 | 12/2006 | Johnson et al. | |
| 2007/0100239 A1 | 5/2007 | Nair et al. | |
| 2008/0045864 A1 | 2/2008 | Candy et al. | |
| 2008/0081993 A1 | 4/2008 | Waki | |
| 2008/0229832 A1 | 9/2008 | Huang | |
| 2008/0294043 A1 | 11/2008 | Johnson et al. | |
| 2008/0319318 A1 | 12/2008 | Johnson et al. | |
| 2009/0076389 A1 | 3/2009 | Jin et al. | |
| 2009/0099456 A1 | 4/2009 | Burcher et al. | |
| 2010/0157732 A1 | 6/2010 | Saenger et al. | |
| 2011/0118984 A1 | 5/2011 | Chevion et al. | |
| 2011/0125014 A1 | 5/2011 | Derode et al. | |
| 2011/0131020 A1* | 6/2011 | Meng | G01V 1/303 703/2 |

FOREIGN PATENT DOCUMENTS

| | | |
|---|---|---|
| WO | 2007133882 A2 | 11/2007 |
| WO | 2011103303 A2 | 8/2011 |

OTHER PUBLICATIONS

Duric et al. "Development of Ultrasound Tomography for Breast Imaging: Technical Assessment", Medical Physics 32(5):1375-86.*

Huang et al. ("MMSE Reconstruction for 3D Freehand Ultrasound Imaging", International Journal of Biomedical Imaging, vol. 2008, Article ID 274164, pp. 1-8).*

Hunstad et al. in an article titled "Seismic Waves and Sound Waves: From Earthquakes to Music" (Seismological Research Letters vol. 84 No. 3 pp. 532-535 May/Jun. 2013).*

Cuiping, Li et al., "In Vivo Breast Sound-Speed Imaging with Ultrasound Tomography", Ultrasound in Medicine & Biology, Oct. 2009, vol. 35, No. 10, pp. 1616-1628.

Korean Intellectual Property Office (KIPO), International Search Report and Written Opinion dated Jun. 2, 2013, PCT International Application No. PCT/US2013/024676, pp. 1-10, with claims searched, pp. 11-18.

Korean Intellectual Property Office (KIPO), International Search Report and Written Opinion dated May 30, 2013, PCT International Application No. PCT/US0213/024539, pp. 1-16, with claims searched, pp. 17-24.

Korean Intellectual Property Office (KIPO), International Search Report and Written Opinion dated May 30, 2013, PCT International Application No. PCT/US2013/024545, pp. 1-12, with claims searched, pp. 13-20.

Korean Intellectual Property Office (KIPO), International Search Report and Written Opinion dated May 30, 2013, PCT International Application No. PCT/US2013/024656, pp. 1-10, with claims searched, pp. 11-16.

Korean Intellectual Property Office (KIPO), International Search Report and Written Opinion dated May 30, 2013, Counterpart PCT International Application No. PCT/US2013/024662, pp. 1-10, with claims searched, pp. 11-19.

Office action dated May 9, 2017 issued in co-pending U.S. Appl. No. 14/339,780.

Office action dated May 1, 2017 issued in co-pending U.S. Appl. No. 14/339,759.

Office action dated Mar. 31, 2017 issued in co-pending U.S. Appl. No. 14/339,712.

Office action dated May 10, 2017 issued in co-pending U.S. Appl. No. 14/339,791.

Office action dated May 2, 2017 issued in co-pending U.S. Appl. No. 14/339,728.

Office action dated Apr. 19, 2017 issued in co-pending U.S. Appl. No. 14/339,770.

Anagaw et al., "Full Waveform Inversion with Total Variation Regularization," Recovery—2011 CSPG CSEG CWLS Convention, pp. 1-4.

Boonyasiriwat et al., 3D Multisource Full-Waveform Inversion using Dynamic Random Phase Encoding,: Society of Exploration Geophysics Technical Program Expanded Abstracts, 2010, pp. 1044-1049.

Cobbold, (2007), Foundations of Biomedical Ultrasound, New York: Oxford University Press, pp. 110-111.

Devaney et al. Super-resolution Processing of Multi-Static Data Using Time Reversal and Music, 2000. {Online]: http://www.ece.neu.edu/faculty/devaney/ajd/preprints.htm, pp. 4,10.

Devaney et al., Time-reversal-based imaging and inverse scattering of multiply scattering point targets, 2005, The Journal of the Acoustical Society of America, vol. 118, No. 5, p. 3132.

Fichtner et al. "Full Seismic Waveform Tomography for upper-mantle structure in the Australasian region using Adjoint Methods," Geophys, J. Int. (2009) 179, pp. 1703-1725.

Huang et al., "A Rapid and Robust Numerical Algorithm for Sensitivity Encoding with Sparsity Constraints: Self-Feeding Sparse SENSE," Magnetic Resonance in Medicine, 2010, 64:1078-1088.

Ikedo et al., Development of a fully automatic scheme for detection of masses in whole breast ultrasound images, 2007, Medical Physics, vol. 24, No. 11, pp. 4381.

Labyed et al., Ultrasound Time-Reversal Music Imaging with Diffraction and Attenuation Compensation, 2012, IEEE Transactions on Ultrasonics, Ferroelectrics, and Frequency Control, vol. 59, No. 10, p. 2188.

Lemoult et al., Time Reversal in Subwavelength-Scaled Resonant Media: Beating the Diffraction Limit, 2011, International Journal of Microwave Science and Technology, vol. 2011, Article ID 425710, p. 4.

Margrave et al., Full Waveform Inversion with Wave Equation Migration and Well Control, CREWES Research Report vol. 22, 2010, pp. 1-20.

(56) References Cited

OTHER PUBLICATIONS

Nguyen et al., The DORT solution acoustic inverse scattering problem of a small elastic scatterer, 2010, Ultrasonics, col. 50, Issue 8, pp. 831-832.
Szabo et al. 2004, "Determining the pulse-echo electromechanical characteristic of a transducer using flat plates and point targets," The Journal of the Acoustical Society of America, vol. 116, No. 1, p. 91.
Tape et al., "Finite-Frequency Tomography Using Adjoint Methods—Methodology and Examples Using Membrane Surface Waves," Geophys. J. Int. (2007) 168, pp. 1105-1129.
Waag et al., A Ring Transducer System for Medical Ultrasound Research, 2006, IEEE Transactions on Ultrasonics, Ferroelectrics, and Frequency control, vol. 53, No. 10, p. 1709.
Yao et al., "A Fast Algorithm to Calculate Ultrasound Pressure Fields from Single-Element Transducers," 1989, IEEE Transactions on Ultrasonics, Ferroelectrics and Frequency Control, vol. 36, No. 4, pp. 446.
Korean Intellectual Property Office (KIPO), International Search Report and Written Opinion dated May 30, 2013, Counterpart PCT International Application No. PCT/US2013/024512, pp. 1-10, with claims searched, pp. 11-21.
Korean Intellectual Property Office (KIPO), International Search Report and Written Opinion dated May 30, 2013, PCT International Application No. PCT/US 2013/024550, pp. 1-11, with claims searched, pp. 12-21.

\* cited by examiner

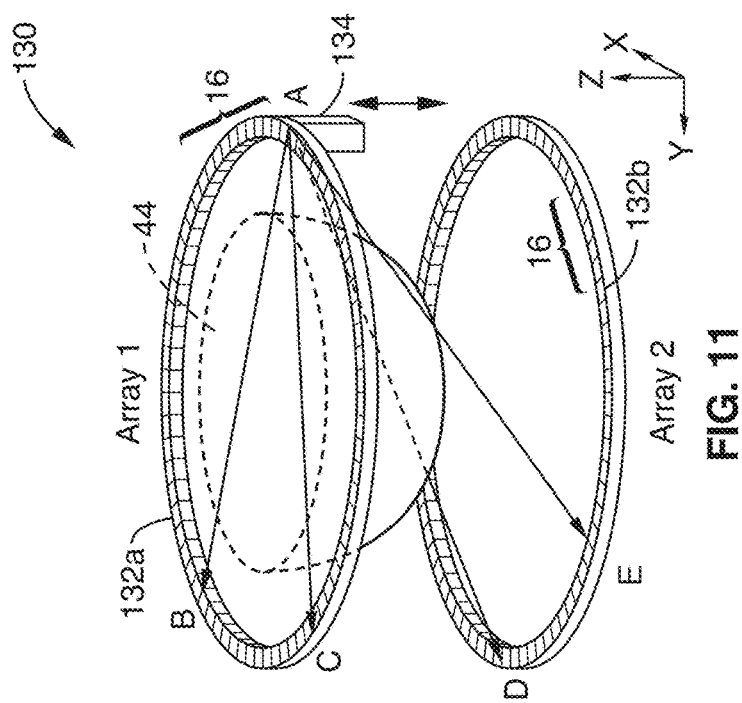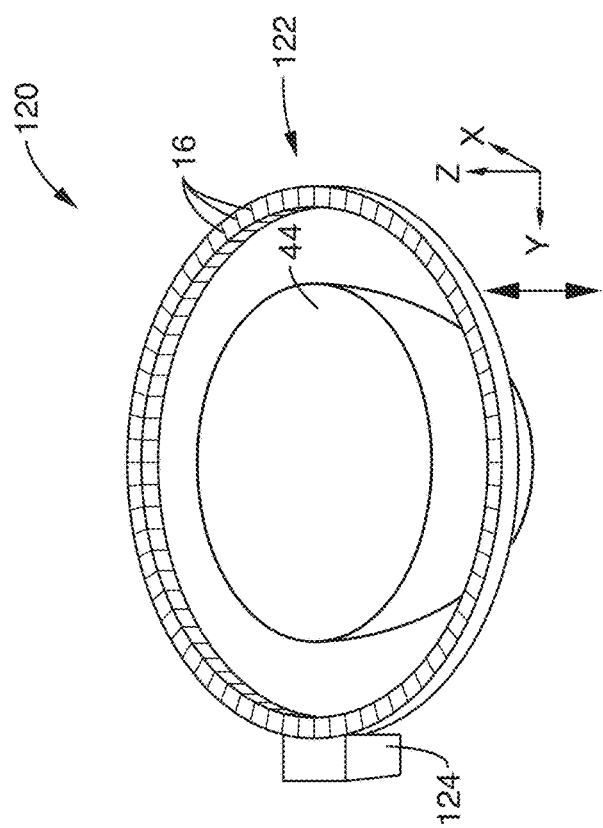

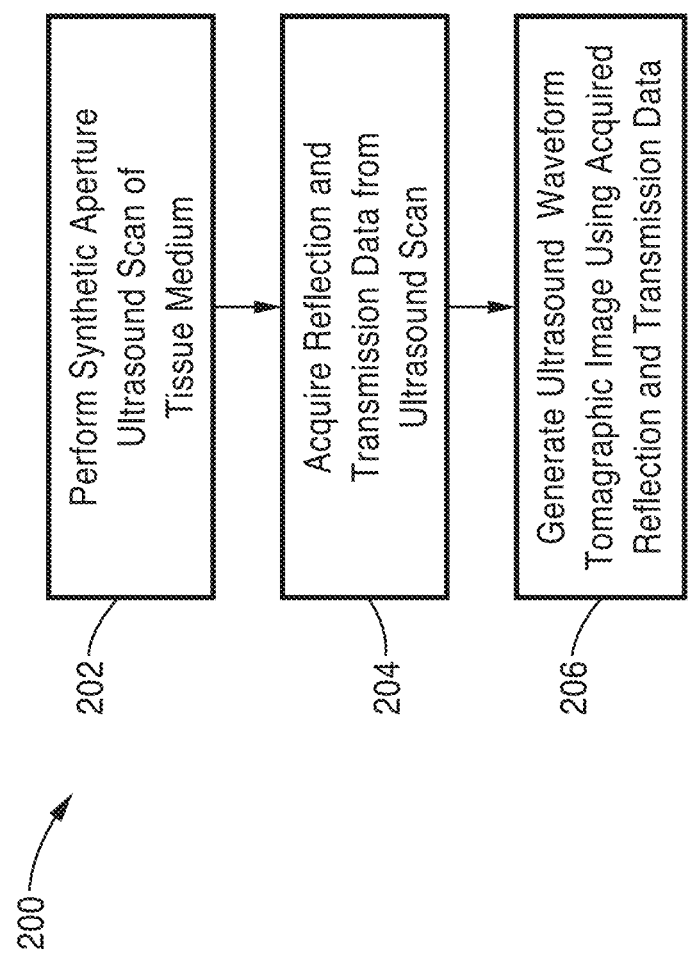

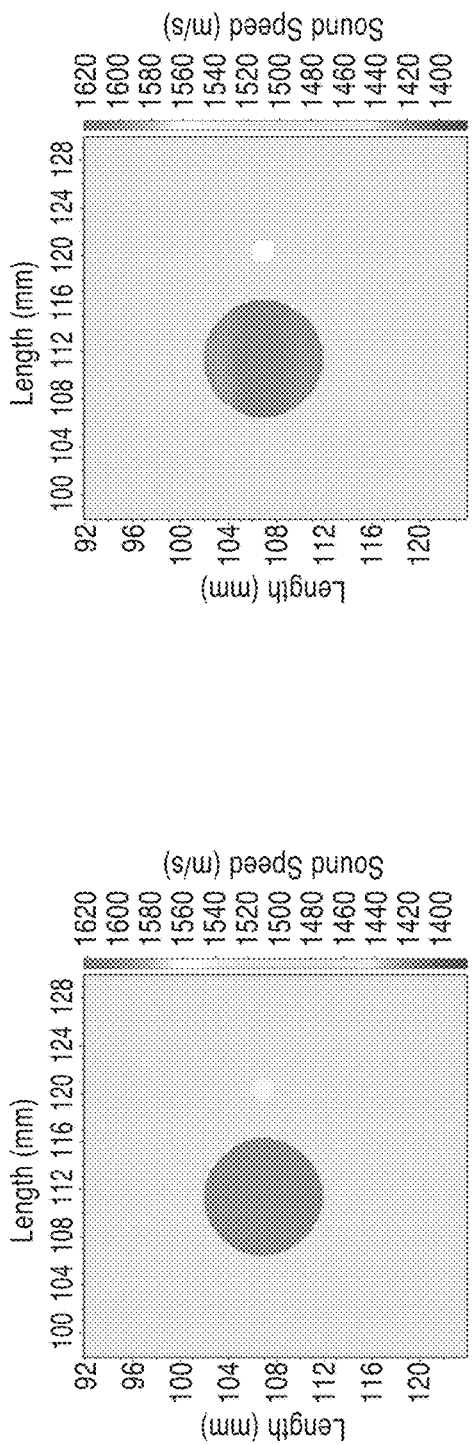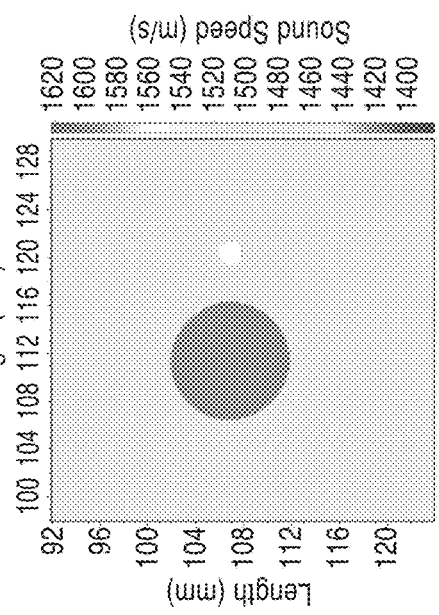
FIG. 27A
FIG. 27B
FIG. 27C

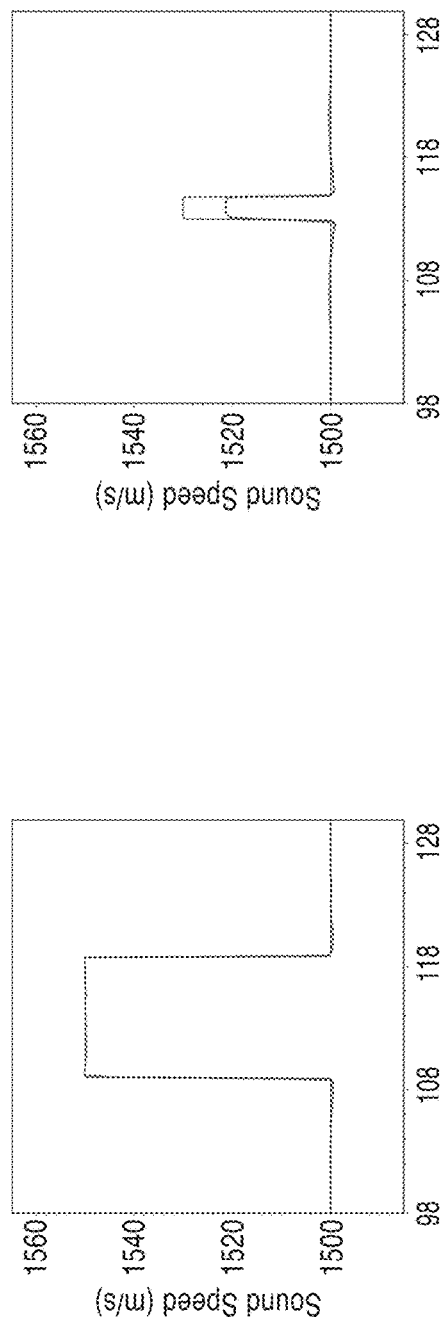
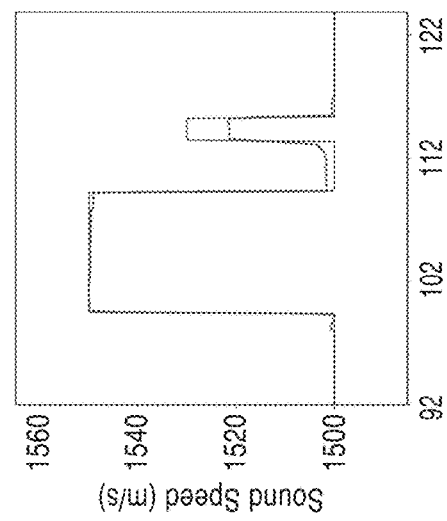
FIG. 28A
FIG. 28B
FIG. 28C

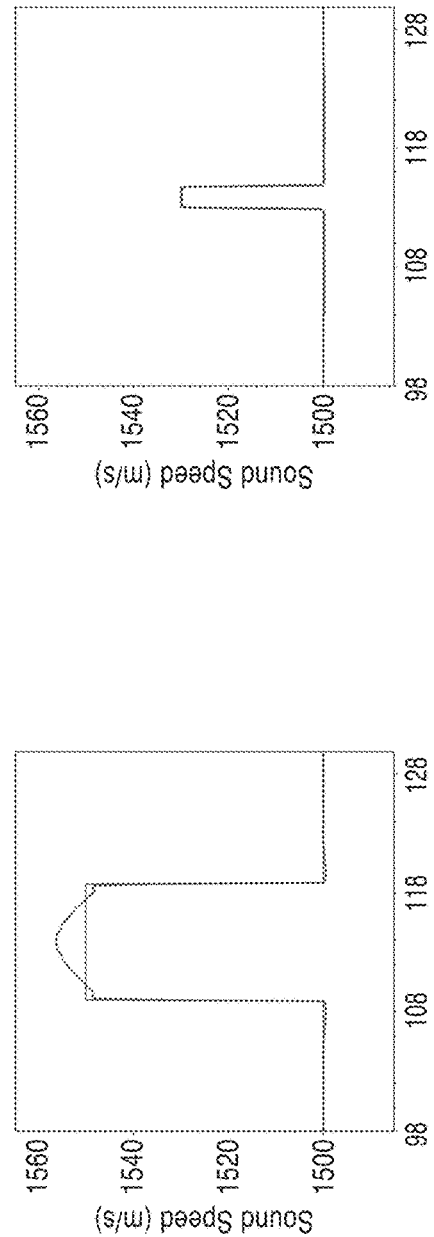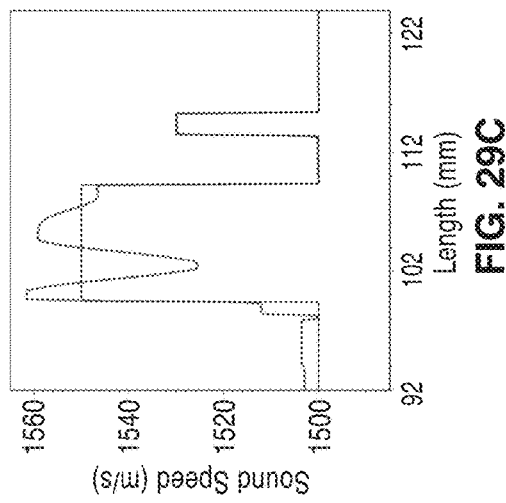
FIG. 29A
FIG. 29B
FIG. 29C

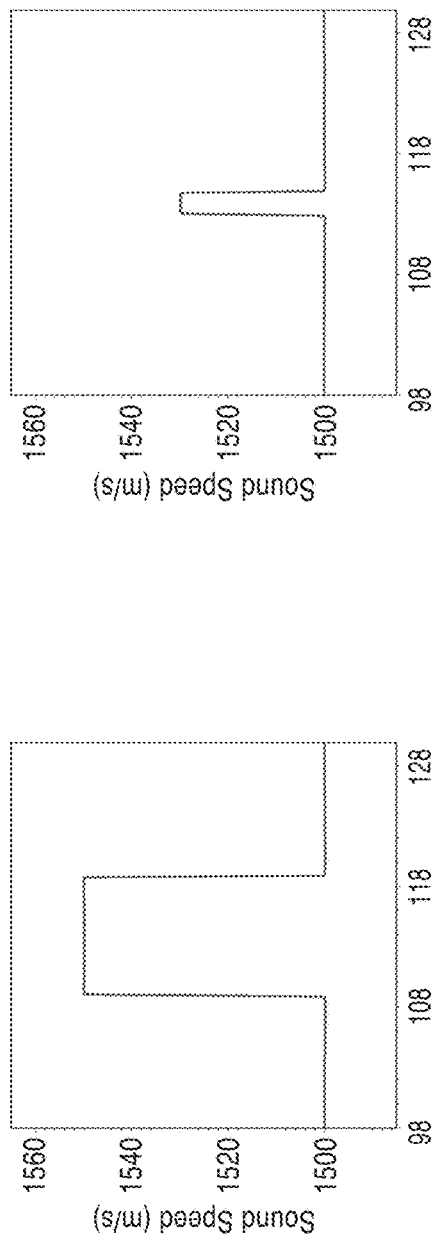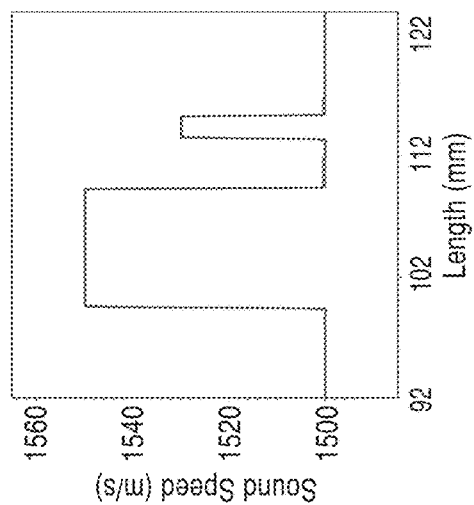
FIG. 30A
FIG. 30B
FIG. 30C

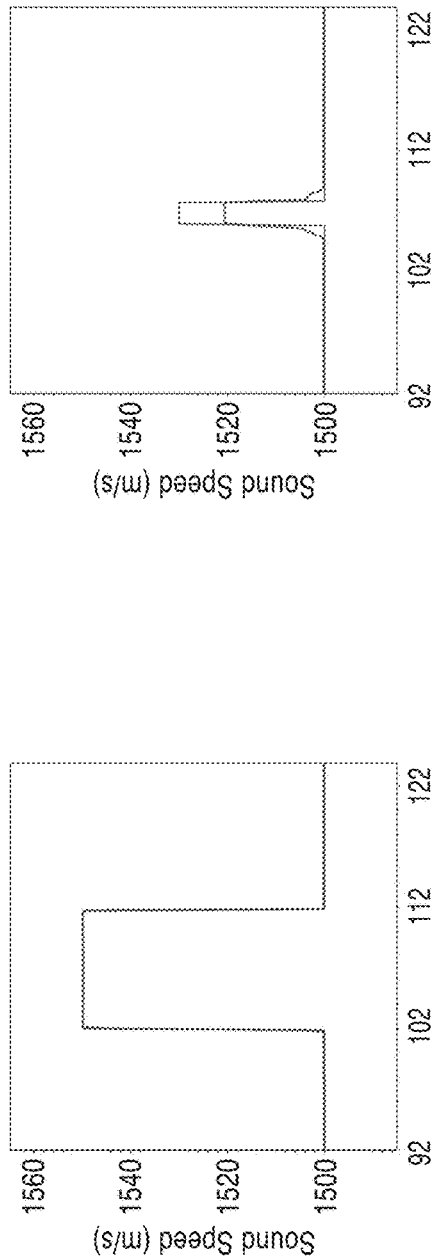
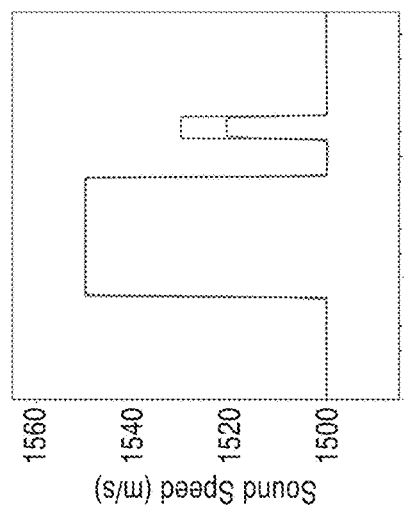
FIG. 33A
FIG. 33B
FIG. 33C

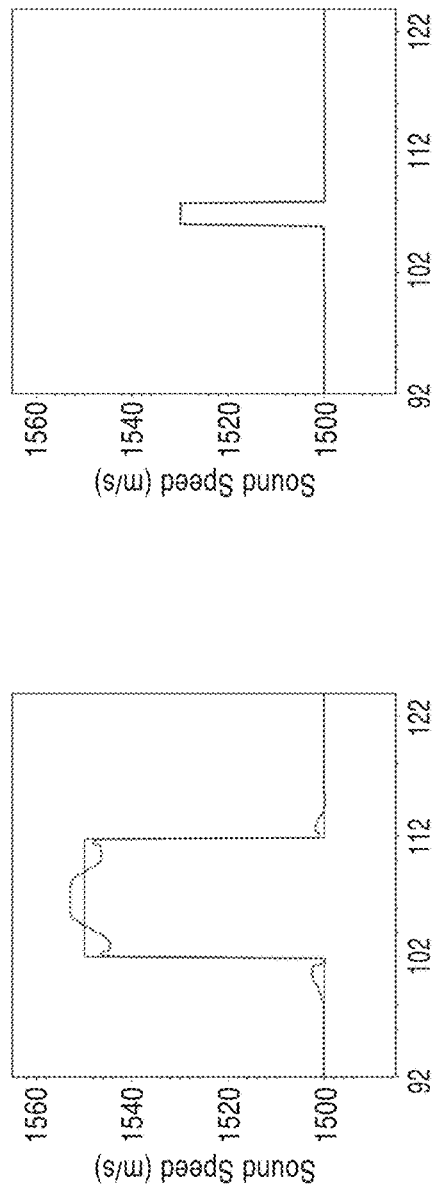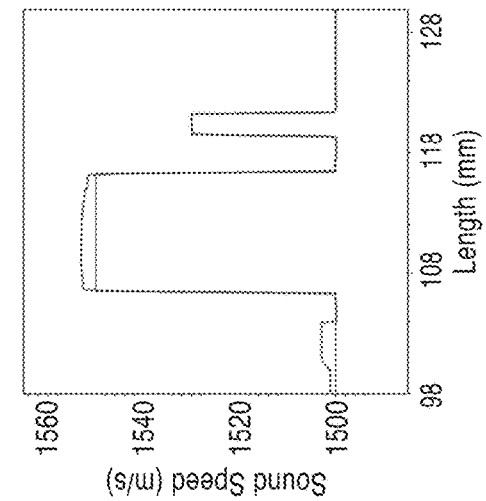
FIG. 34A  FIG. 34B  FIG. 34C

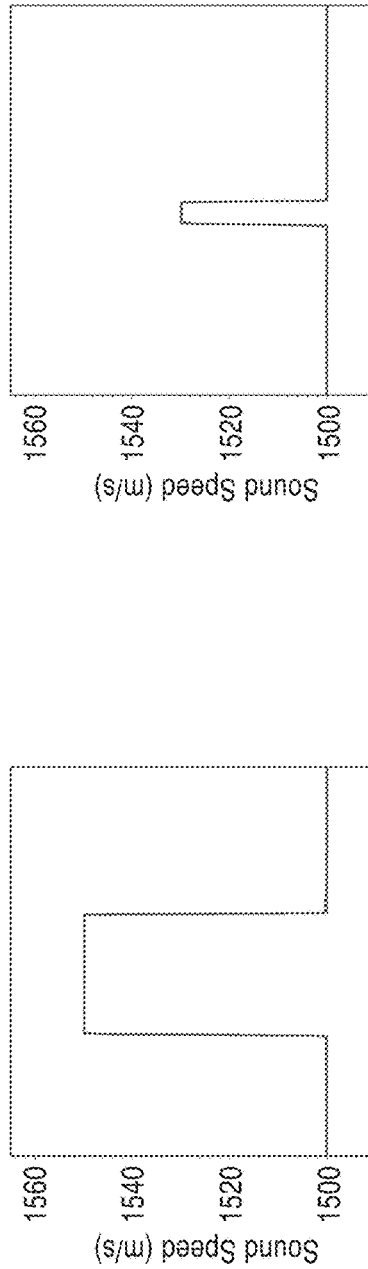
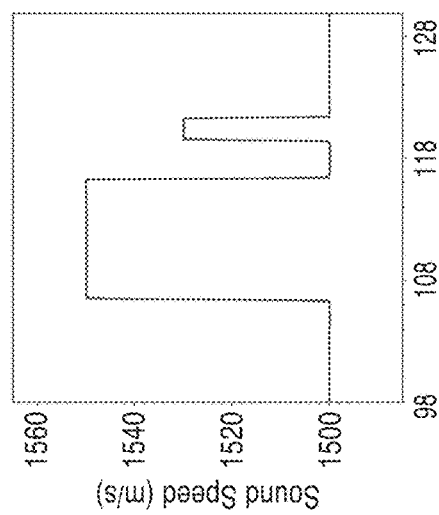
FIG. 35A
FIG. 35B
FIG. 35C

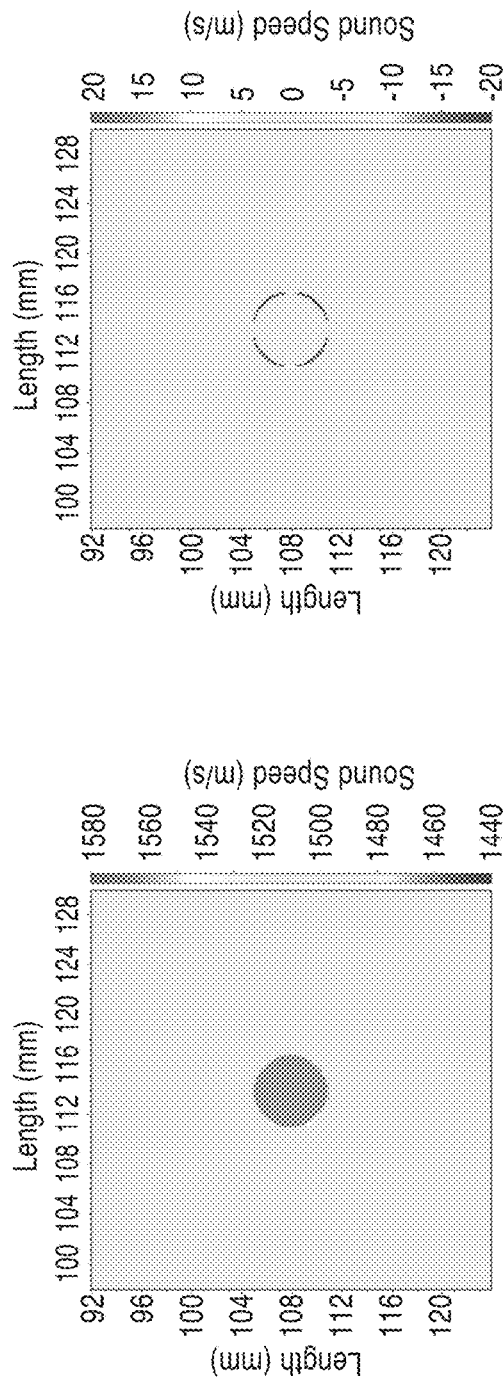
FIG. 37A
FIG. 37B
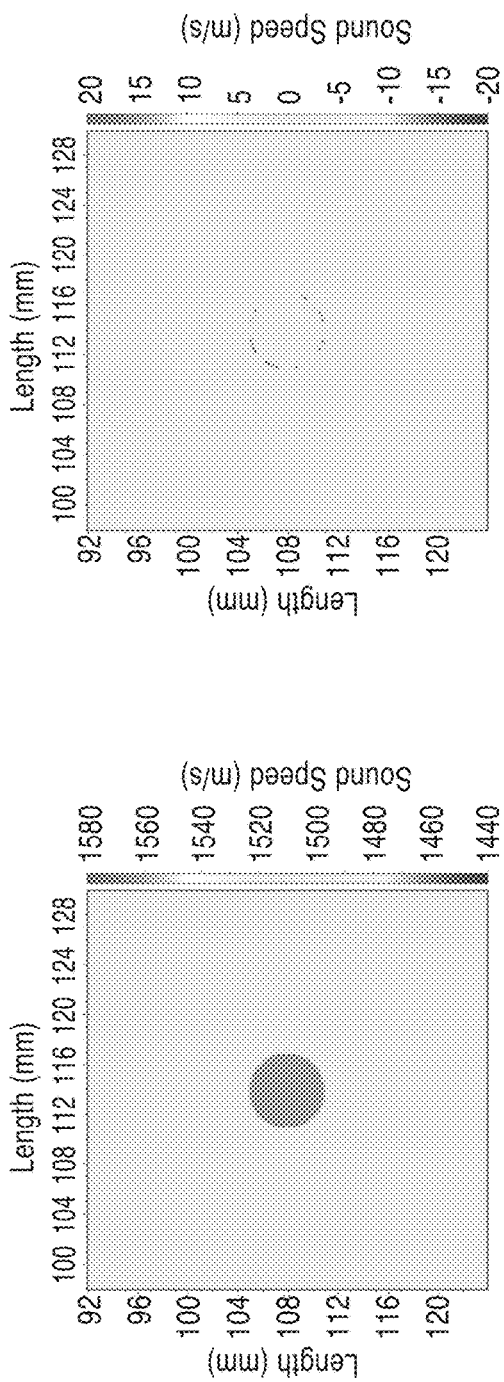
FIG. 37C
FIG. 37D

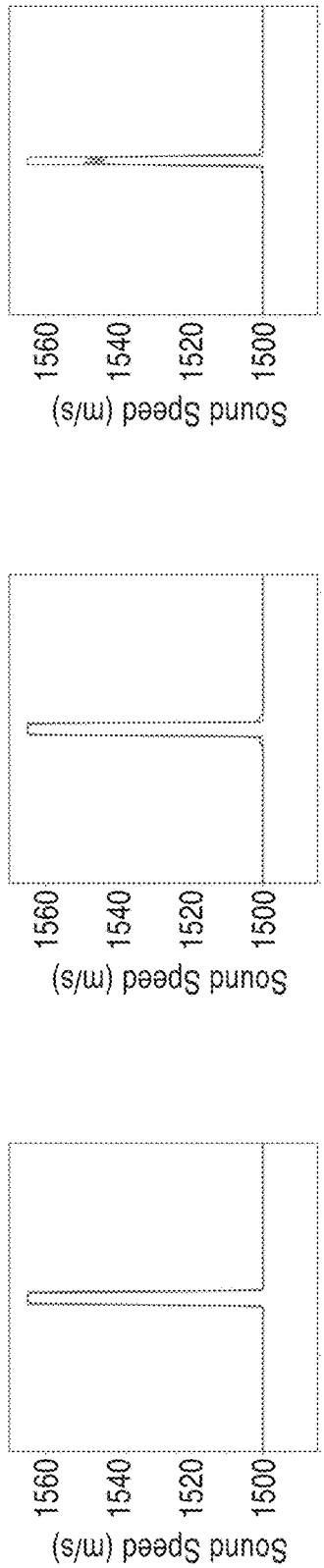
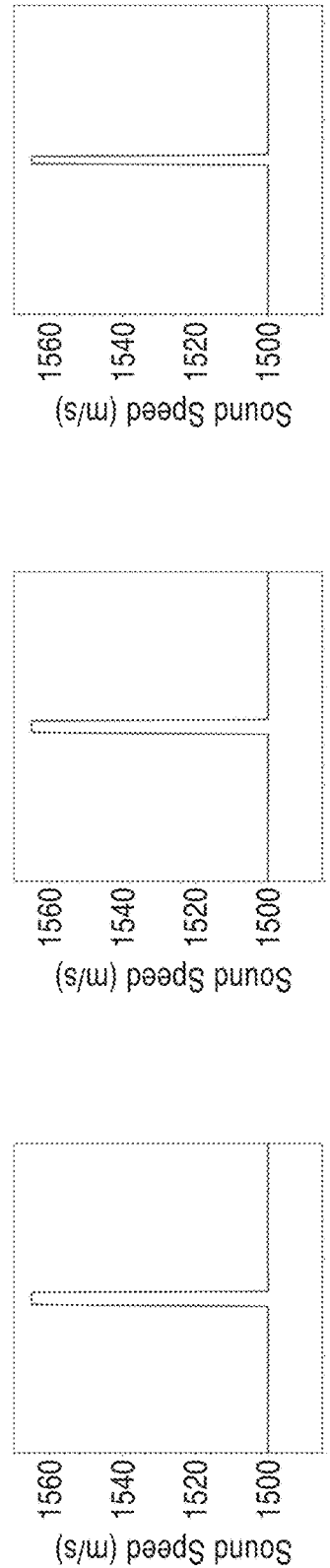
FIG. 40A  FIG. 40B  FIG. 40C
FIG. 40D  FIG. 40E  FIG. 40F

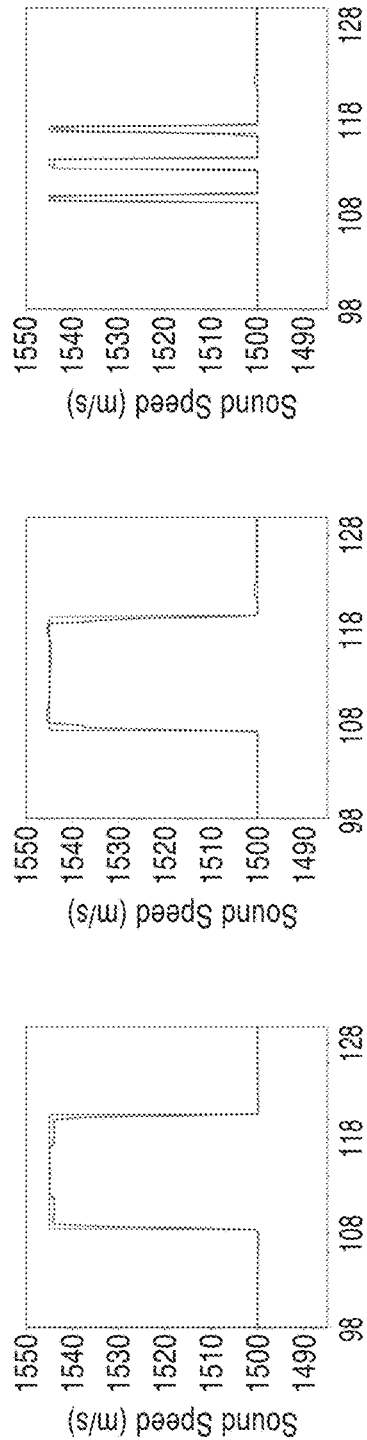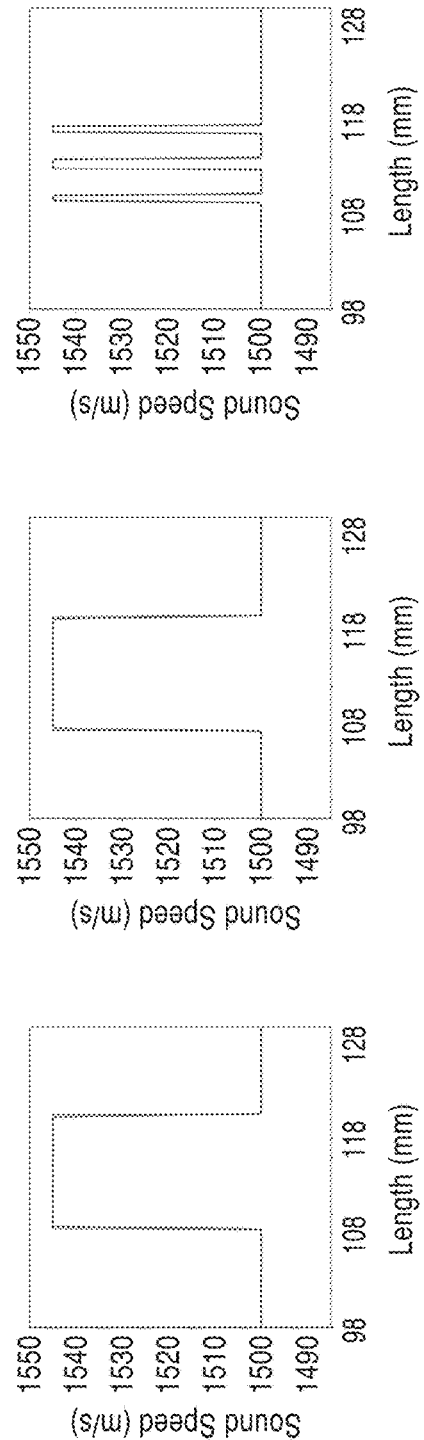

ULTRASOUND WAVEFORM TOMOGRAPHY WITH SPATIAL AND EDGE REGULARIZATION

CROSS-REFERENCE TO RELATED APPLICATIONS

This application is a 35 U.S.C. § 111(a) continuation of PCT international application number PCT/US2013/024662 filed on Feb. 4, 2013, incorporated herein by reference in its entirety, which claims priority to, and the benefit of, U.S. provisional patent application Ser. No. 61/594,865, filed on Feb. 3, 2012, incorporated herein by reference in its entirety. Priority is claimed to each of the foregoing applications.

INCORPORATION-BY-REFERENCE OF COMPUTER PROGRAM APPENDIX

This invention was made with Government support under Contract No. DE-AC52-06NA25396 awarded by the Department of Energy, and Grant No. MIPR0LDATM0144 from the Breast Cancer Research Program of DoD-Congressionally Directed Medical Research Programs. The Government has certain rights in the invention.

The above-referenced PCT international application was published as PCT International Publication No. WO 2013/116854 on Aug. 8, 2013, incorporated herein by reference in its entirety.

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to imaging, and more particularly to ultrasound imaging using a synthetic aperture ultrasound waveform tomography.

2. Description of Related Art

Breast cancer is the second-leading cause of cancer death among American women. The breast cancer mortality rate in the U.S. has been flat for many decades, and has decreased only about 20% since the 1990s. Early detection is the key to reducing breast cancer mortality. There is an urgent need to improve the efficacy of breast cancer screening. Ultrasound tomography is a promising, quantitative imaging modality for early detection and diagnosis of breast tumors.

Ultrasound waveform tomography is gaining popularity, but is computationally expensive, even for today's fastest computers. The computational cost increases linearly with the number of transmitting sources.

Synthetic-aperture ultrasound has great potential to significantly improve medical ultrasound imaging. In a synthetic aperture ultrasound system, ultrasound from each element of a transducer array propagates to the entire imaging domain, and all elements in the transducer array receive scattered signals.

Many conventional ultrasound systems record only 180° backscattered signals. Others are configured to receive only transmission data from the scanning arrays. Accordingly, these systems suffer from extensive computational costs, insufficient resolution, or both.

Waveform inversion can be implemented either in the time domain, or in the frequency domain. Because of the ill-posedness caused by the limited data coverage, multiple local-minimum solutions exist, and therefore, certain stabilization numerical techniques need to be incorporated within inversion process to obtain a global-minimum solution. In recent years, many approaches have been developed for this purpose. Regularization techniques can be employed to alleviate the instability of the original problem. Preconditioning approaches can also be used in waveform inversion to create a well-conditioned problem with lower dimensions. In addition, prior information about the model can be introduced to improve the convergence of waveform inversion.

In waveform inversion with regularization, reconstruction results depend dramatically on the strength of the regularization, which is controlled by the regularization parameter. If the regularization parameter is too large, the inversion results are over regularized, which usually leads to over-smoothed reconstructions; on the other hand, if the regularization parameter is smaller than necessary, the inversion results are under regularized, and the reconstructions tend to be degraded by image artifacts and noise. Therefore, an appropriate regularization parameter is essential for high-resolution tomographic reconstructions. The shapes, sizes and densities and tumors and breast tissue can vary significantly within a breast. The conventional approach to regularization uses a constant regularization parameter for the entire imaging domain. This approach inevitably yields over-regularization for certain regions/tumors, and under-regularization of other regions/tumors.

BRIEF SUMMARY OF THE INVENTION

The system and method of the present invention uses ultrasound data acquired using a synthetic-aperture ultrasound system. The investigational synthetic-aperture ultrasound tomography system of the present invention allows acquisition of each tomographic slice of patient ultrasound data in real time. In the system, each element of the transducer array transmits ultrasound sequentially, and elements in the transducer array simultaneously record ultrasound signals scattered from the tissue after each element is fired. The features of the system and method of the present invention provide a real-time synthetic-aperture system that can be used for patient data acquisition.

In the synthetic-aperture ultrasound tomography system of the present invention, ultrasound from each element of a transducer array or a virtual source of multiple elements propagates to the entire imaging domain, and all elements in the transducer array receive ultrasound signals reflected/scattered from the imaging region and/or transmitted/scattered through the imaging region. Therefore, the acquired synthetic-aperture ultrasound data contain information of ultrasound reflected/scattered and transmitted from all possible directions from the imaging domain to the transducer array to generate a more accurate, 3-D, high resolution image, while minimizing computational costs of the system.

One aspect of the invention is an ultrasound waveform tomography method with the spatially variant regularization to improve sound-speed reconstructions of small breast tumors. The nonlinear conjugate gradient (NCG) method is used to solve waveform inversion with the spatially variant regularization. The gradient of the misfit function is obtained using an adjoint state method.

Another aspect of the invention is a novel ultrasound waveform tomography method with a spatially variant modified total-variation regularization scheme, such that the edge-preserving can be more effective without adding too much extra computational cost.

Another aspect of the invention is an ultrasound waveform tomography method with an edge-guided regularization to improve sound-speed reconstructions of small breast tumors. The nonlinear conjugate gradient (NCG) method is used to solve waveform inversion with the edge-guided regularization. The gradient of the misfit function is obtained using an adjoint state method.

Another aspect of the invention is a novel ultrasound waveform tomography method with an edge-guided modified total-variation (TV) regularization scheme, in which a separate regularization term is added, such that the edge-preserving can be more effective without adding too much extra computational cost.

In one aspect, the misfit function using an alternating minimization algorithm. The cost function is decomposed with the modified TV regularization into two regularization problems, a $L_2$-norm-based Tikhonov regularization problem and a $L_1$-norm-based TV regularization problem. The nonlinear conjugate gradient (NCG) approach is used to solve for the first Tikhonov regularization problem. Then, an adjoint state method is used to compute the gradient of the misfit function. The split-Bregman method to is used to solve the second regularization problems. In one embodiment, the use of the split-Bregman method allows for computations that are (a) it is computationally efficient; and (b) the selection of the smoothing parameter in the TV regularization term can be avoided.

The methods of the present invention are directed to performing ultrasound waveform tomography of acquired reflection and transmission signals with use of a regularization scheme. In particular, transmission and reflection data are used for ultrasound waveform tomography with an edge-guided regularization scheme and spatially-variant regularization scheme.

The present invention includes a spatially-variant regularization scheme for ultrasound waveform tomography to improve tomographic reconstructions for the entire imaging domain. The spatially-variation regularization of the present invention is independent of the selection of the specific regularization techniques. The edge-guided regularization of the present invention is also independent of the selection of the specific regularization techniques.

However, the modified total-variation regularization scheme with the spatially-variation regularization or with an edge-guided regularization for ultrasound waveform tomography produces the most accurate reconstruction results. Therefore, a combination of the spatially-variant regularization with the modified total-variation regularization or a combination of the edge-guided regularization with the modified total-variation regularization yields the best results in numerical examples.

In another aspect, the method of the present invention specifies different regularization parameter values in different regions according to the approximate locations and sizes of breast tumors provided by ray tomography. For example, a large regularization parameter value was selected for a region with a large tumor, while a smaller value in the other regions or the region with a small tumor.

To solve ultrasound waveform tomography with spatially-variant regularization or with edge-guided regularization, computational methods used for solving ultrasound waveform tomography with the modified total-variation regularization are implemented via incorporation of an alternating minimization algorithm. The misfit function is decomposed into two subproblems: 1) a $L_2$-norm-based Tikhonov regularization problem, and 2) a $L_1$-norm-based TV regularization problem.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 10 shows a schematic view of a torroidal array scanner having a a circular array of transducers.

FIG. 11 shows a schematic view of a synthetic-aperture ultrasound breast tomography scanner that incorporates use of two circular transducer arrays.

FIG. 14 is a flow diagram of a synthetic aperture ultrasound tomography method in accordance with the present invention.

FIG. 27A through FIG. 27C show images of sound-speed reconstructions obtained using ultrasound waveform tomography with the modified TV regularization using a global regularization parameter appropriate for the large tumor (FIG. 27A), with the modified TV regularization using a global regularization parameter appropriate for the small tumor (FIG. 27B), and with the spatially-variant modified TV regularization (FIG. 27C).

FIG. 28A through FIG. 28C vertical and horizontal profiles of the ultrasound waveform reconstructions through the center of both tumors.

FIG. 29A through FIG. 29C show vertical and horizontal profiles of the ultrasound waveform reconstructions through the center of both tumors.

FIG. 30A through FIG. 30C show vertical and horizontal profiles of the ultrasound waveform reconstructions through the center of both tumors.

Figure 31B:
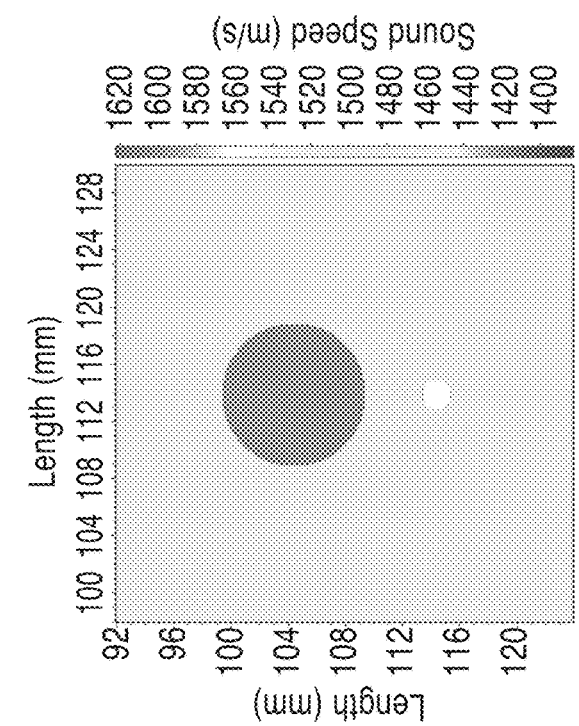
Figure 31A:
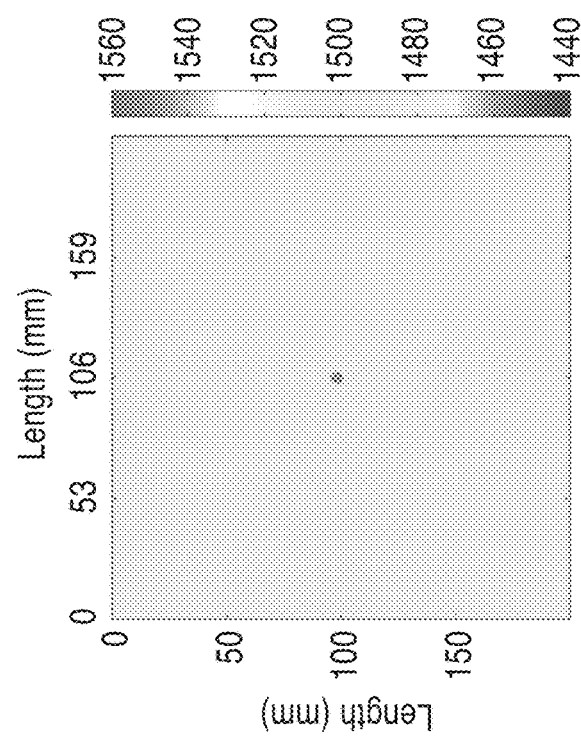

FIG. 31A and FIG. 31B are images of a numerical breast phantom that contains two breast tumors. The diameter of the smaller one is 2.0 mm, which is approximately 1.3 wavelengths; the diameter of the large tumor is 10.0 mm, or about 6.6 wavelengths.

Figure 32B:
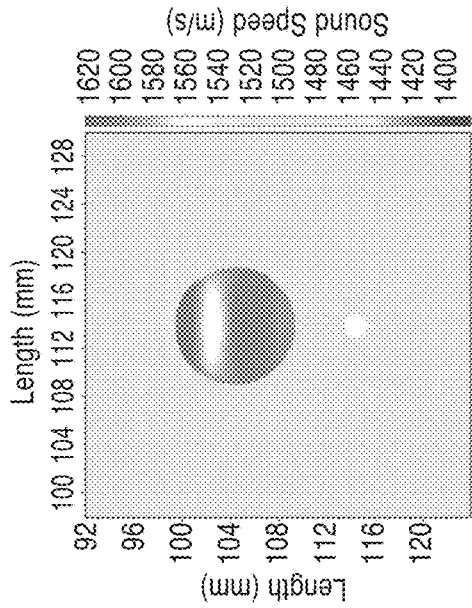
Figure 32A:
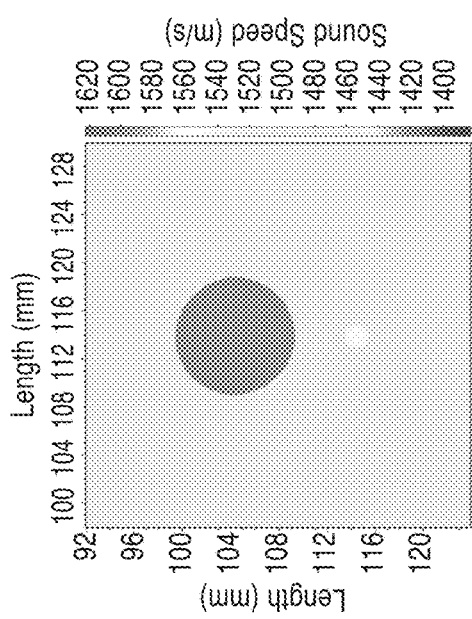
Figure 32C:
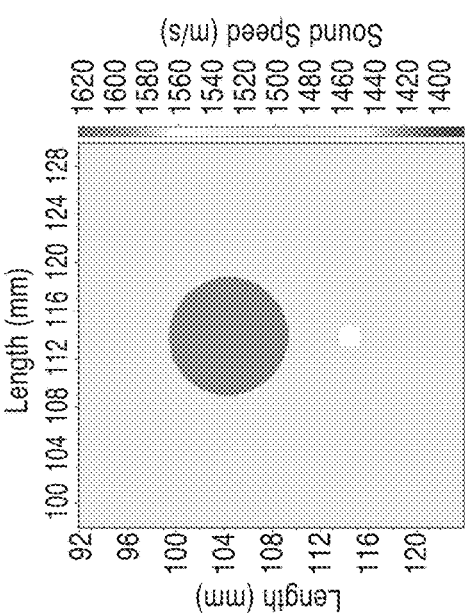

FIG. 32A through FIG. 32C are images showing sound-speed reconstructions obtained using ultrasound waveform tomography with the modified TV regularization using a global regularization parameter appropriate for the large tumor (FIG. 32A) and a global regularization parameter appropriate for the small tumor (FIG. 32B), and with the spatially-variant modified TV regularization (FIG. 32C).

FIG. 33A through FIG. 33C show images of vertical and horizontal profiles of ultrasound waveform reconstructions through the center of both tumors.

FIG. 34A through FIG. 34C are images showing vertical and horizontal profiles of ultrasound waveform tomography reconstructions through the center of both tumors.

FIG. 35A through FIG. 35C show images of vertical and horizontal profiles of ultrasound waveform tomography reconstructions through the center of both tumors.

Figure 36B:
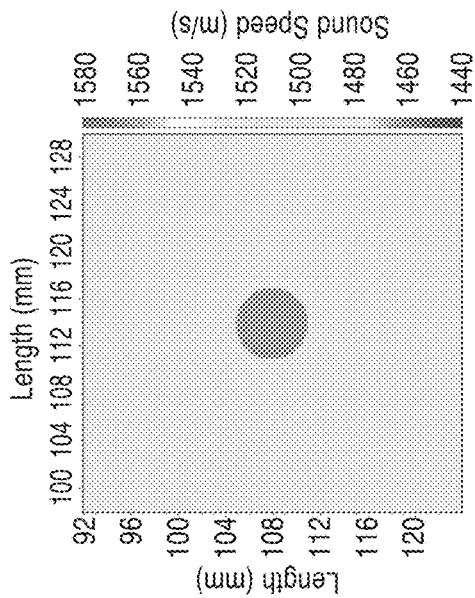
Figure 36D:
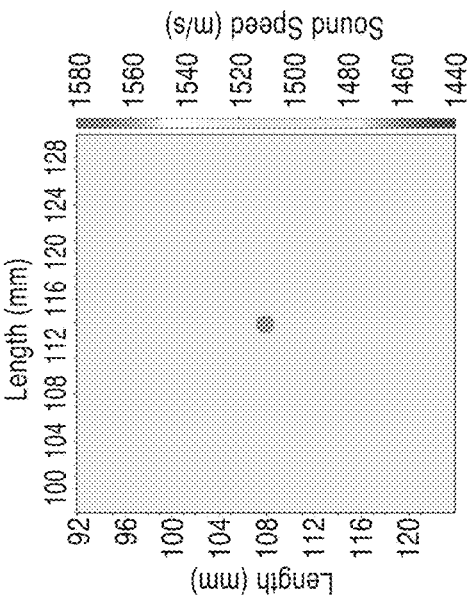
Figure 36A:
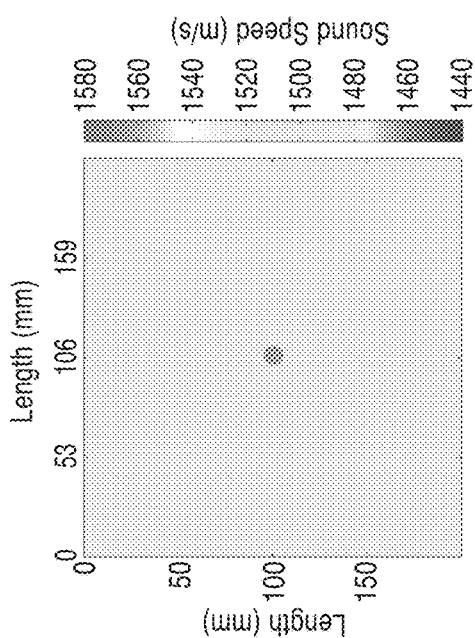
Figure 36C:
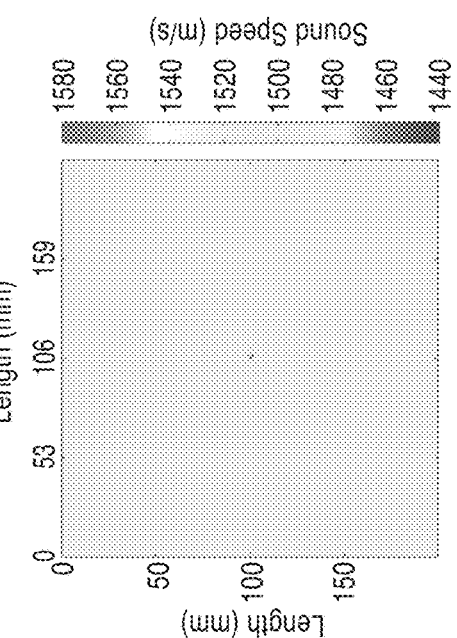

FIG. 36A through FIG. 36D are images showing a numerical breast phantom that contains one breast tumor. The diameter of the tumor in FIG. 36A and FIG. 36B is 6 mm, which is approximately four wavelengths of ultrasound. The diameter of the tumor in FIGS. 36C and 36D is 1.5 mm, which is approximately one wavelength.

FIG. 37A through FIG. 37D show images of sound-speed reconstructions obtained using ultrasound waveform tomography with the regular modified TV regularization (FIG. 37A) and its difference from the true numerical phantom with a 6-mm tumor (FIG. 37B); with the edge-guided modified TV regularization (FIG. 37C) and its difference from the true numerical phantom (FIG. 37D).

FIG. 38A through FIG. 38F are images showing profiles of the sound-speed reconstructions obtained using ultrasound waveform tomography with the regular modified TV regularization (FIG. 38A through FIG. 38C), and with the edge-guided modified TV regularization (FIG. 38D through FIG. 38F), for the numerical phantom with a 6-mm tumor.

Figure 39B:
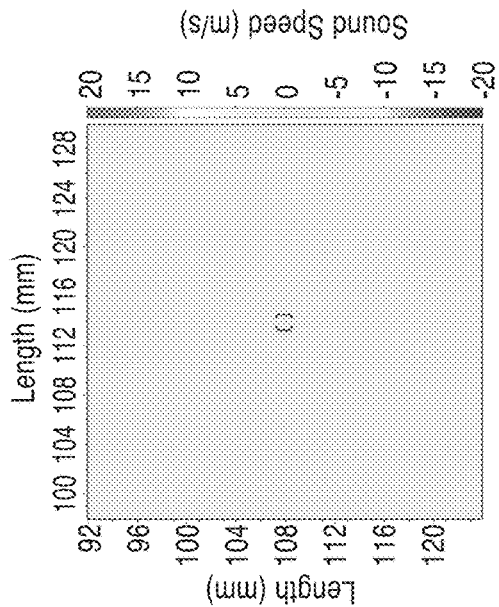
Figure 39D:
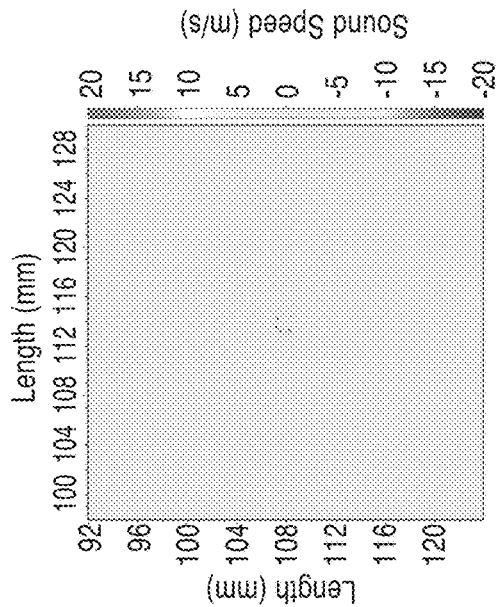
Figure 39A:
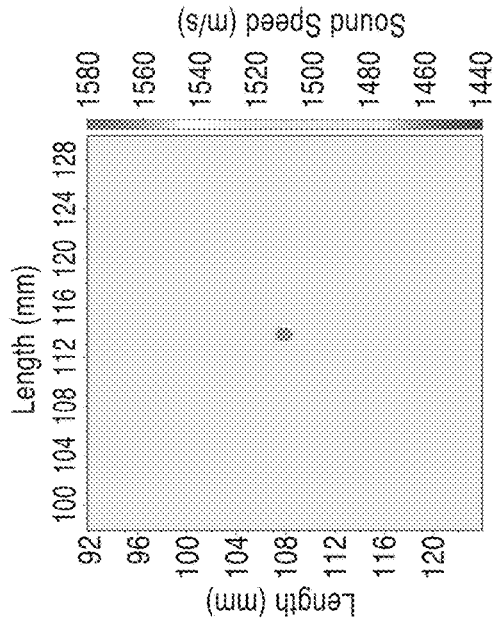
Figure 39C:
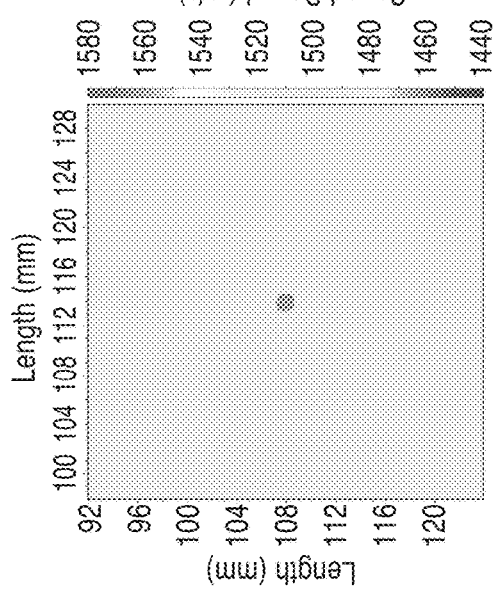

FIG. 39A through FIG. 39D are images showing Sound-speed reconstructions obtained using ultrasound waveform tomography with the regular modified TV regularization (FIG. 39A) and its difference from the true numerical phantom with a 1.5-mm tumor (FIG. 39B); with the edge-guided modified TV regularization (FIG. 39C) and its difference from the true numerical phantom (FIG. 39D).

FIG. 40A through FIG. 40F show profiles of the sound-speed reconstructions obtained using ultrasound waveform tomography with the regular modified TV regularization (FIG. 40A through FIG. 40C); with the edge-guided modified TV regularization (FIG. 40D through FIG. 40F); for the numerical phantom with a 1.5-mm tumor.

Figure 41B:
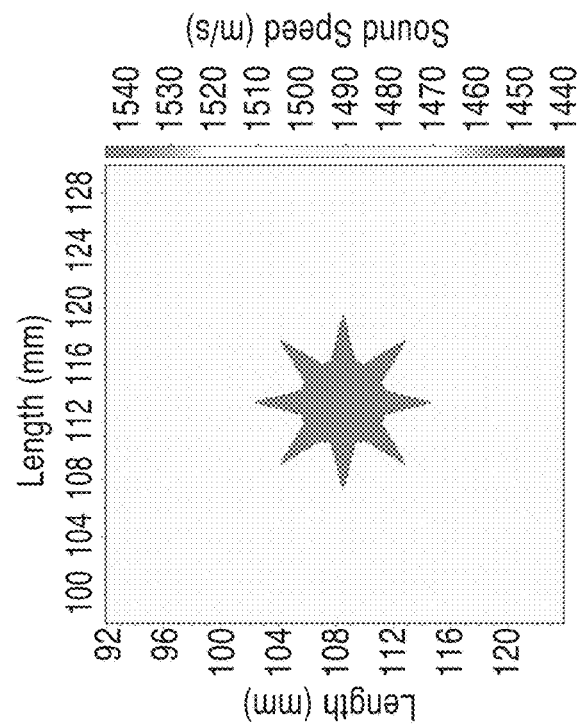
Figure 41A:
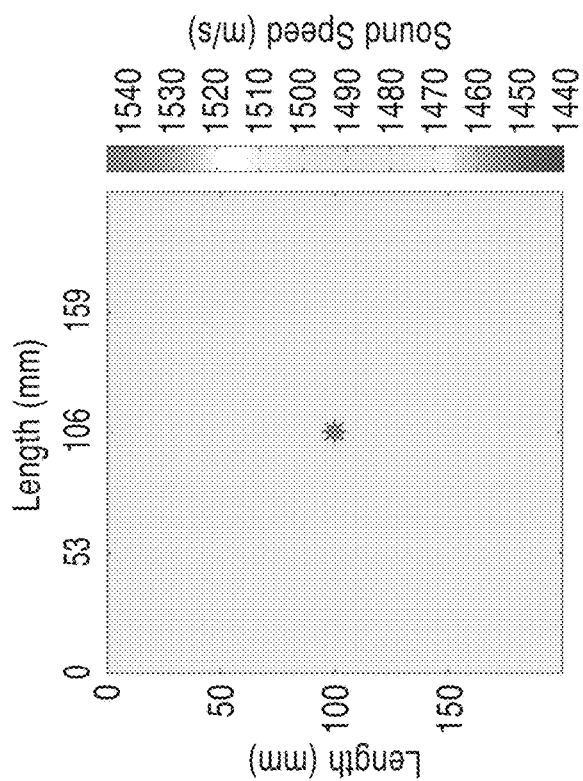
Figure 42A:
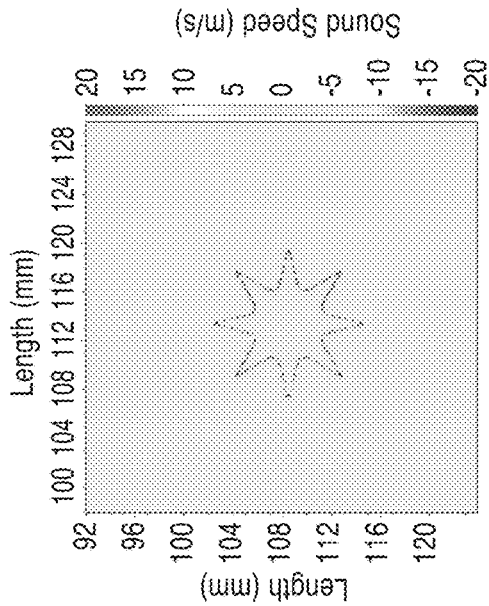
Figure 42B:
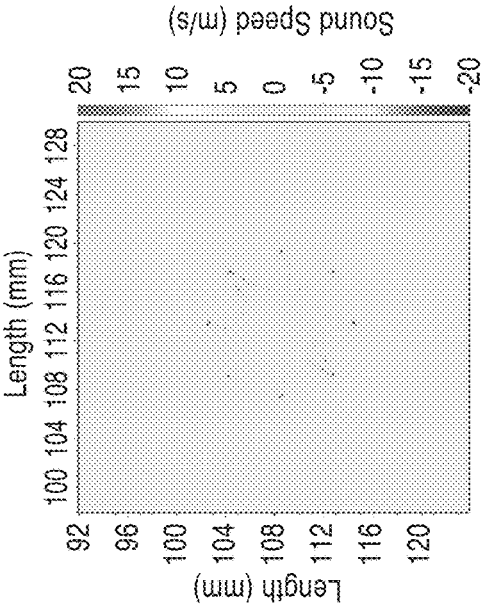
Figure 42C:
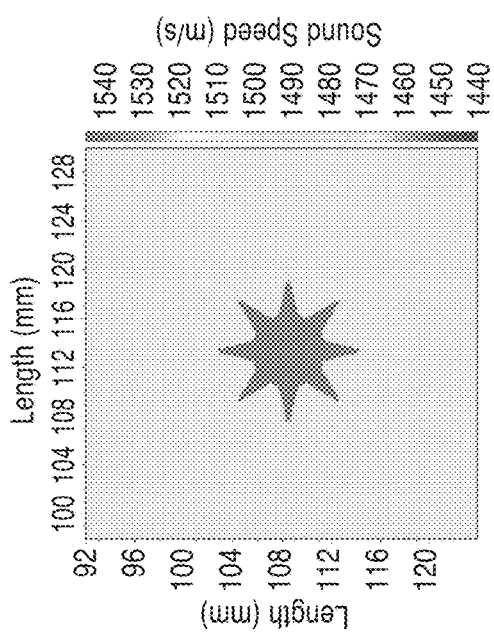
Figure 42D:
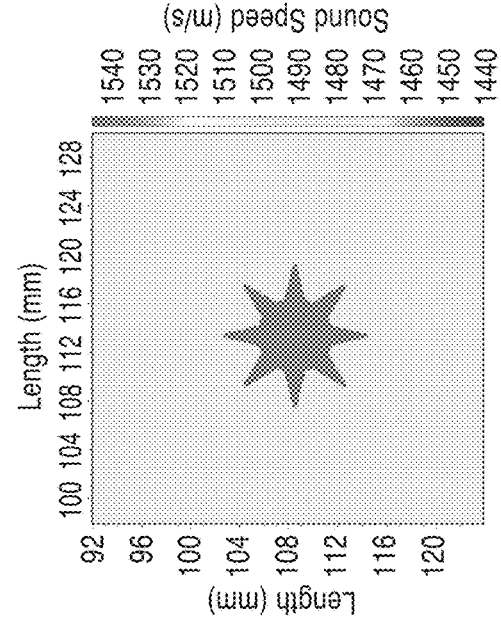

FIG. 41A and FIG. 41B show images of a numerical breast phantom contains a spiculated breast tumor. The diameter of the tumor is 6 mm, which is approximately 4 wavelengths. The maximum distance between the ends of the spiculated features is 12 mm FIG. 42A through FIG. 42D show sound-speed reconstructions obtained using ultrasound waveform tomography with the regular modified TV regularization (FIG. 42A) and its difference to the true model (FIG. 42B); with the edge-guided modified TV regularization (FIG. 42C) and its difference from the true numerical phantom (FIG. 42D).

FIG. 43A through FIG. 43F show Profiles of the sound-speed reconstructions obtained using the regular modified TV regularization (FIG. 43A through FIG. 43C); using the edge-guided modified TV regularization (FIG. 43D through FIG. 43F).

DETAILED DESCRIPTION OF THE INVENTION

The description below is directed to synthetic aperture ultrasound tomography systems for imaging a medium such as patient tissue, along with ultrasound waveform tomography methods for acquiring and processing data acquired from these systems, or other systems that may or may not be available in the art.

The synthetic-aperture breast ultrasound tomography system of the present invention uses synthetic-aperture ultrasound to obtain quantitative values of mechanical properties of breast tissues. In this system, each transducer element transmits ultrasound waves sequentially, and when an ultrasound transducer element transmits ultrasound waves propagating through the breast, all ultrasound transducer elements (at least within a portion of an array) simultaneously receive ultrasound reflection/transmission, or forward and backward scattering signals. The ultrasound reflection/transmission signals are used to obtain quantitative values of mechanical properties of tissue features (and in particular breast tumors), including the sound speed, density, and attenuation.

While the systems and methods described below are particularly directed and illustrated for imaging of breast tissues, it is appreciated that the systems and methods may also be employed for waveform tomography on other tissues or scanning mediums.

I. Synthetic Aperture Ultrasound Tomography System

Figure 1:
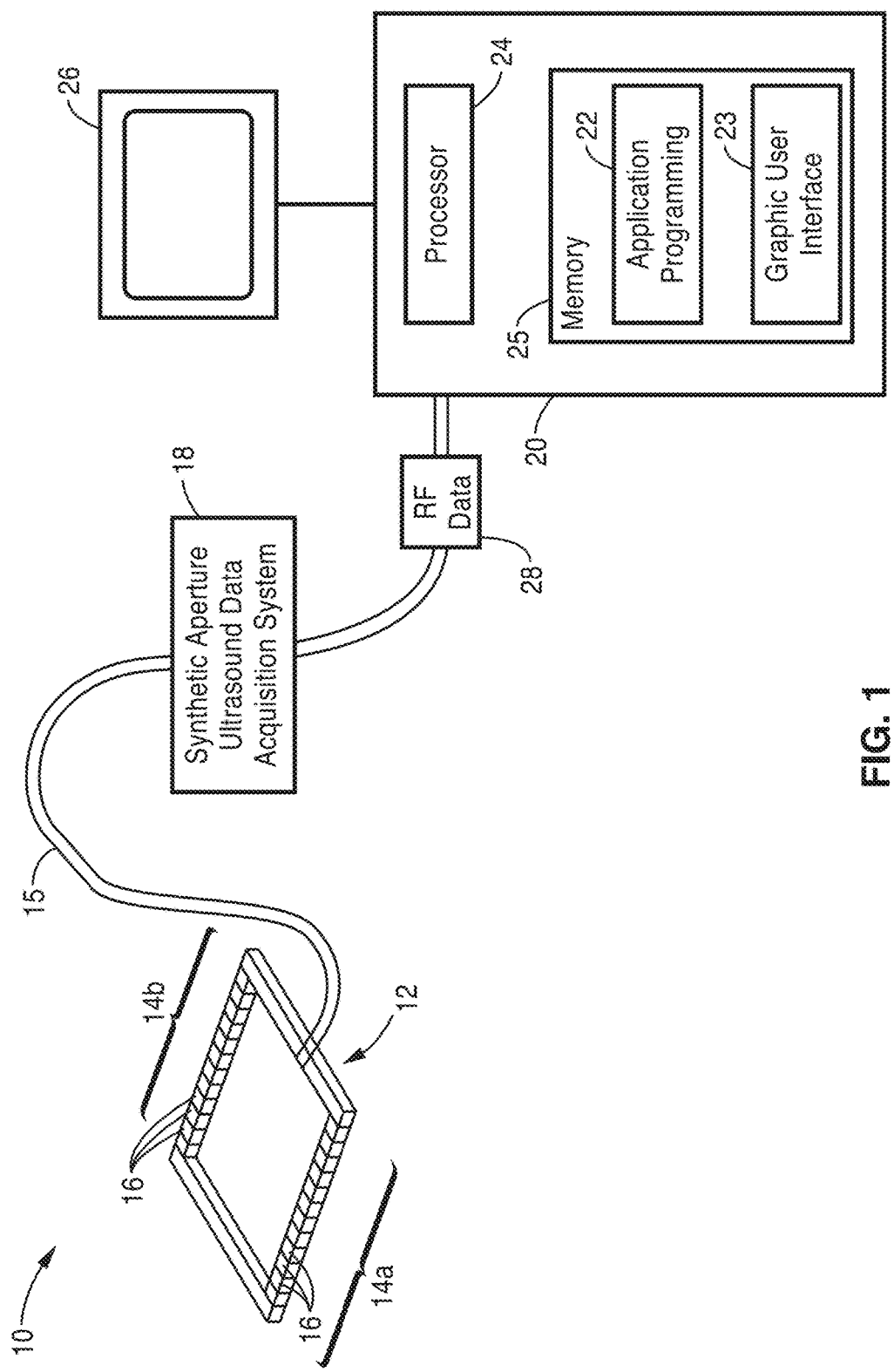
FIG. 1 is a schematic diagram of a synthetic-aperture ultrasound system in accordance with the present invention.

FIG. 1 is a schematic diagram of a synthetic-aperture ultrasound system 10 in accordance with the present invention. The system 10 includes a scanner 12 comprising a plurality of individual transducer elements 16 disposed within one or more arrays (e.g. the opposing parallel arrays 14a and 14b shown in FIG. 1). The scanner 12 is coupled to a server or like computing apparatus 20 (e.g. with a cable 15 or other connection means such as, but not limited to, a wireless connections means) and synthetic aperture ultrasound data acquisition system 18 that outputs RF data 28 corresponding to readings acquired by the scanner 12.

The computer 20 comprises a processor 24 configured to operate one or more application programs 22 located within memory 25, wherein the application programs 22 may contain one or more algorithms or methods of the present invention for imaging a tissue medium for display via a graphical user interface 23 on monitor 26, or other means. For example, the application programming 22 may comprise the programming configured for operating the sequential excitation method 50 shown in FIG. 4 or ultrasound waveform tomography imaging method 200 shown in FIG. 14. The computer 20 controls ultrasound tomography data acquisition, and the process is completed automatically. The whole-breast scanning time with approximately 100 slides takes approximately 2 minutes.

Figure 2:
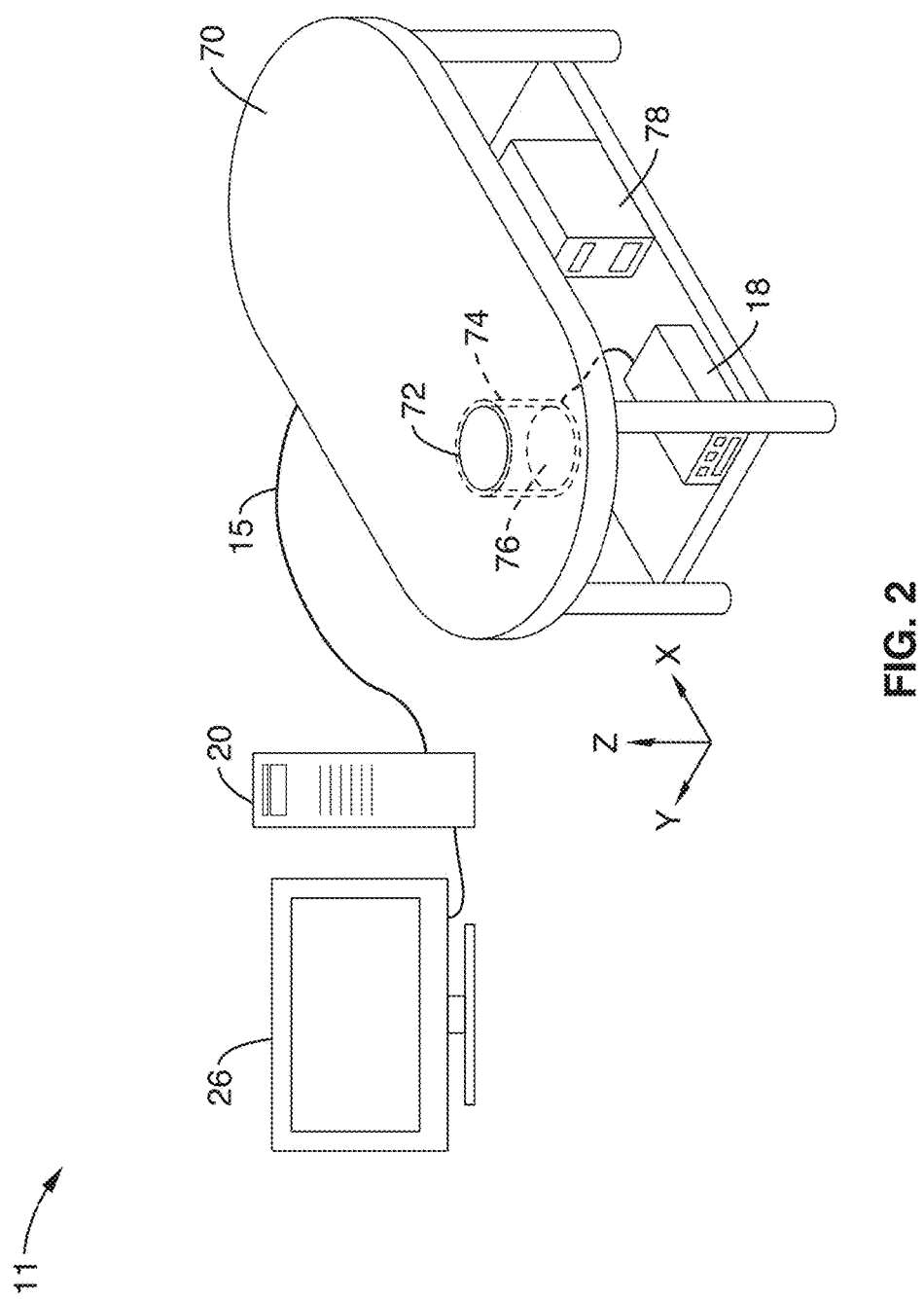
FIG. 2 is a schematic diagram of a synthetic-aperture ultrasound tomography system for scanning breast tissue in accordance with the present invention

FIG. 2 is a schematic view of a breast ultrasound tomography system 11 in accordance with the present invention. System 11 includes a table 70 having a water tank 76 with an open aperture at the top of the table 70 for insertion of the patient's breast tissue (which ideally hangs pendant within water tank 76 during imaging). Tank 76 includes one or more synthetic-aperture ultrasound transducer arrays 74 located within one or more surfaces of the tank. The transducer array(s) 74 are immersed within the water tank 76 configured for receiving the patients breast 44 through aperture 72, and scanning the breast 44 while the patient is lying down on the table 70 in the prone position. As described in further detail below, transducer array(s) 74 may comprise a number of different configurations, with the water tank housing 76 shaped accordingly to house the array(s) 74. The water tank housing 76 material preferably comprises a light, non-conductive material that conforms to the shape of the array(s) 74 (e.g. rectangular for 2-parallel bar array scanner 12 of FIG. 1, or cylindrical for the scanners 110, 120 and 130 shown in FIG. 7, FIG. 10 and FIG. 11, respectively).

Positioning of the active areas of all array(s) 74 relative to the water tank housing 76 is preferably aligned such that the ultrasound energy for the transducer elements 16 (FIG. 1) is focused onto the same plane perpendicular to the housing (for parallel bar scanner 12 (FIG. 5) or planar 100 (FIG. 6) arrays). The arrays (e.g. arrays 14a and 14b, FIG. 1) are preferably electrically isolated and grounded.

The system 11 includes a data acquisition system 18 that may be coupled to a computer system or electronics 78 that control scanning. The data acquisition system 18 may also be coupled to a computer 20 for running application programming 22 (FIG. 1) to perform tomography reconstructions.

During the ultrasound data acquisition in the synthetic-aperture ultrasound tomography system 10, the raw ultrasound data 28 (radio-frequency data) may be first stored within computer memory 25 (FIG. 1) (which may comprise solid state drives or other storage means available in the art), allowing real-time patient data acquisition for clinical applications.

Figure 3:
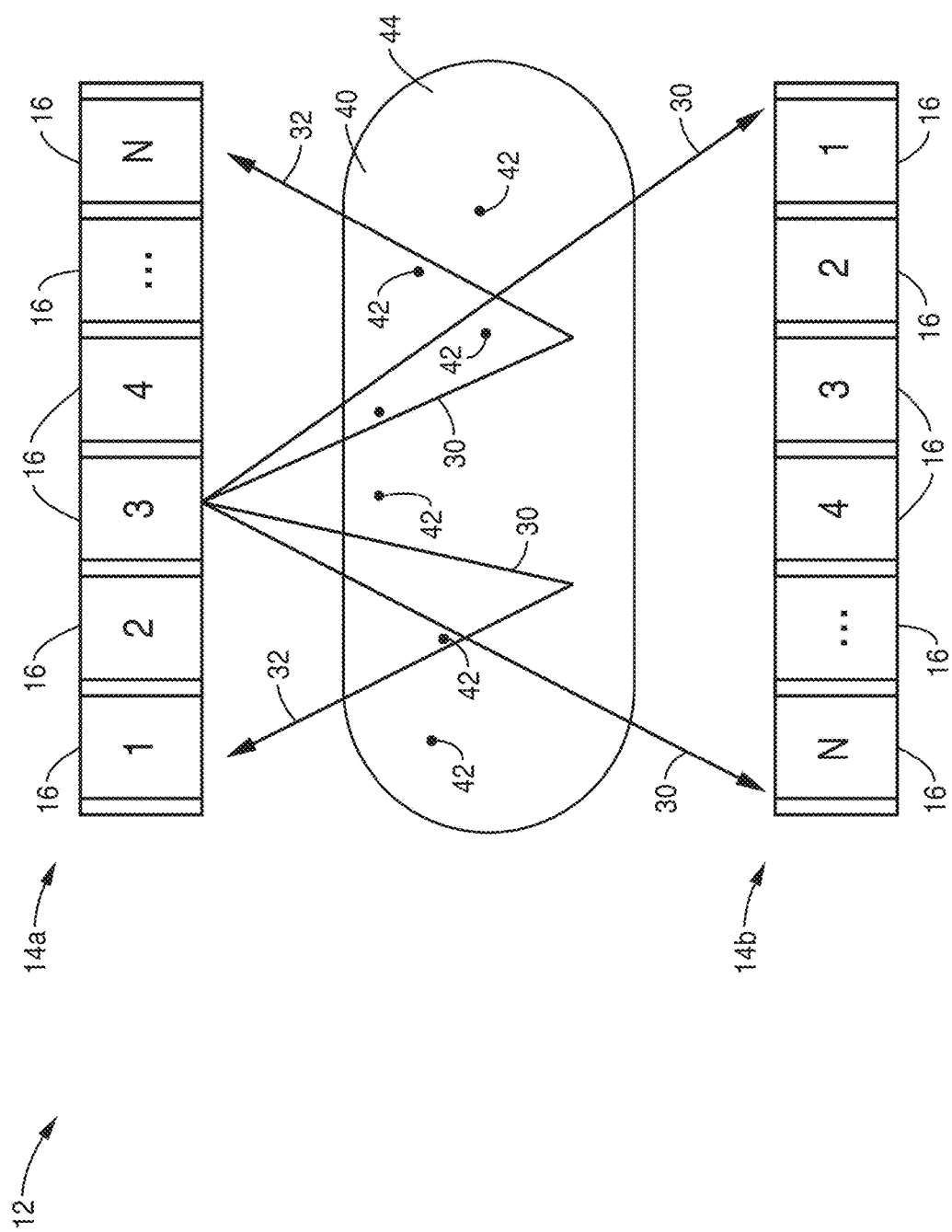
FIG. 3 is a schematic diagram of the scanner of the ultrasound tomography system of FIG. 1 interrogating a region of tissue.

FIG. 3 is a schematic diagram of the two parallel bar arrays 14a and 14b of scanner 12 of FIG. 1 shown interrogating a region of tissue 44 (e.g. breast tissue for mammography) in accordance with a preferred method of the present invention. The ultrasound imaging system 10 focuses an array 14a and 14b of N transducers 16 acting in a transmit-receive mode. Each element of the array 14a 14b is excited sequentially (e.g. transducer 3 of array 14a is shown in excitation mode) to generate an ultrasound field or signal 30 through the tissue surface 40 and into tissue medium 44 having a plurality of point scatterers 42. The backscattered signals 32 are measured in parallel by all N elements 16. In addition, opposing array 14b transducers are positioned facing array 14a such that one or more elements of the array 14b receive direct transmission signals 30 simultaneously with reception of backscatter or reflection signals 32 being received by array 14a.

Figure 4:
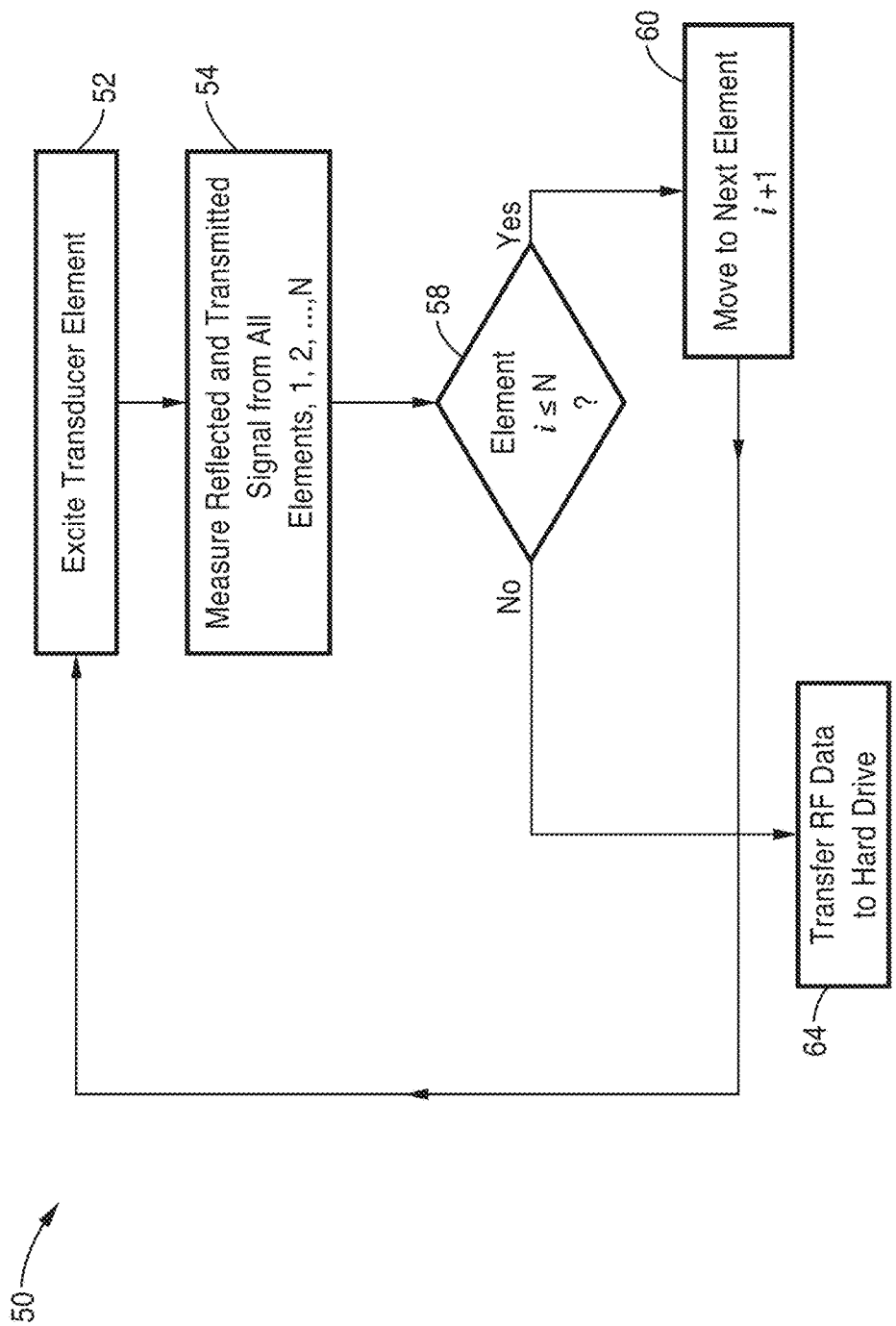
FIG. 4 shows flow diagram of a method for sequentially exciting a region of tissue and acquiring reflection and transmission data in accordance with the present invention.

FIG. 4 shows flow diagram of a method 50 for sequentially exciting a region of tissue 44 in accordance with the present invention. At step 52, a first element (e.g. element 1 or i) of array 14a 14b of N ultrasound transducer elements 16 is excited for interrogating an inhomogeneous medium 44. At step 54, the backscattered/reflected signals 32 are received/measured by all elements 16 (of at least 14a), while transmission signals 30 are received/measured by one or more elements 16 of array 14b. At step 58, the method evaluates whether all the elements 16 in the arrays 14a and 14b have been excited (and imaged). If the last element in the arrays 14a, 14b has not been reached, the method moves to the next element 16 in the array (14a or 14b) at step 60, and repeats the process sequentially until the $N^{th}$ element is reached. At this point, the individual reflection/transmission data are RF data, and the process 50 transfers the RF data to memory or solid state drives 25 at step 64.

In the phased transducer arrays for synthetic-aperture breast ultrasound tomography, a plurality of transducer elements 16 are fired with different delayed times to simulate ultrasound waves emerging from a virtual point source. The systems and methods of the present invention preferably use the virtual point sources of the synthetic-aperture breast ultrasound tomography system to improve signal-to-noise ratios of breast ultrasound data.

The various scanning arrays invention, described below with reference to FIG. 5 through FIG. 7 and FIG. 10 through FIG. 13, are shown to illustrate that the systems 10, 11 and methods 50, 200 may be achieved in various configurations. Yet, the scanning arrays of FIG. 5 through FIG. 7 and FIG. 10 through FIG. 13 all share at least one common characteristic in that at a plurality of transducers 16 of an array, or portion of an array, oppose (at a spaced-apart distance across the target scanning medium 44) a plurality of transducers 16 of either another portion of the array, or a separate array, so that reflection and transmission data may be acquired with each successive transducer excitation. The following are specific examples of arrays that may be used in the systems 10, 11 and methods 50, 200 of the present invention. However, other configurations are contemplated. In each of these configurations, the scanner 74 is shown without table 70 or housing 76 for clarity.

A. Dual Parallel-Bar Array Scanner

Figure 5:
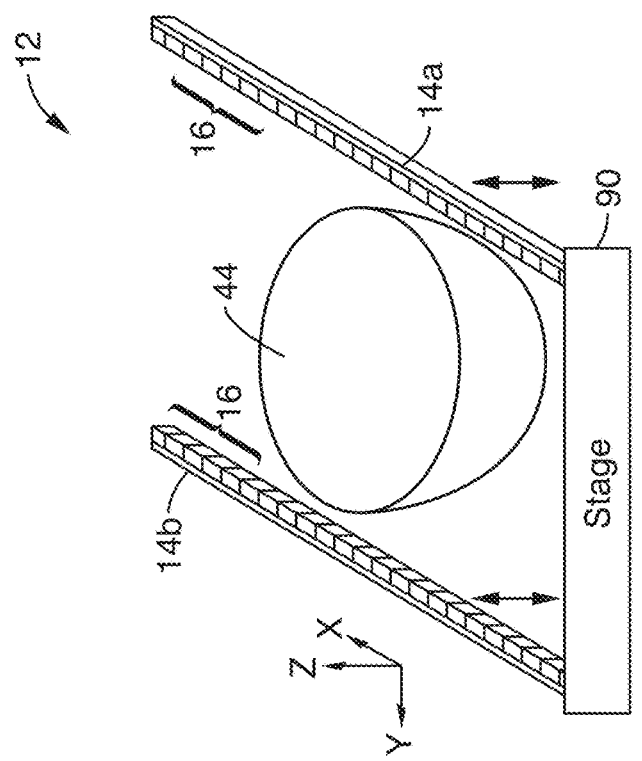
FIG. 5 illustrates a schematic view of a two parallel-bar ultrasound transducer array scanner.

FIG. 5 illustrates a two parallel-bar ultrasound transducer array scanner 12, which is illustrated in reference to implementation within system 10 in FIG. 1, and schematically in operation as a synthetic-aperture scanner in FIG. 3.

As shown in FIG. 5, the two arrays 14a and 14b are shown in opposing orientation (e.g facing each other and matching in location along x-axis in FIG. 5), and positioned in the x-y plane (preferably parallel to table 70 in FIG. 2, such that they are spaced-apart across the scanning region 44. Each of the 14a and 14b comprises a plurality of N transducers 16 (e.g. count of 128) linearly aligned in series (shown in along the x-axis for reference) as parallel-phased arrays firing toward each other in operation (see FIG. 3).

A robotic stage 90 is provided so that the arrays can move in unison vertically along the z-axis to scan the tissue 44. The transducer arrays 14a and 14b are configured to scan the breast 44 from the chest wall to the nipple region, slice by slice. To image the axillary region (region of breast closest to the armpit of the patient, not shown), the two transducer arrays 14a and 14b can be steered toward the axillary region, with one of the transducer arrays placed near the axillary region. The axillary region, or basin, is important to oncologic surgeons, as it represents the principal lymphatic drainage region of the breast. Lymphatic metastasis from a malignant breast lesion will most often occur in this region.

Arrays 14a and 14b may also be translated (either in concert, or with respect to each other) in the x and y axes to closely conform to varying patient anatomy.

Figure 8:
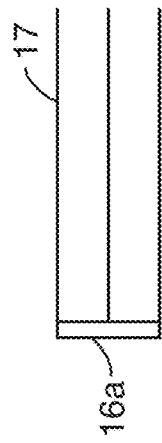
FIG. 8 shows a flat transducer configured to generate a collimated beam.
Figure 9:
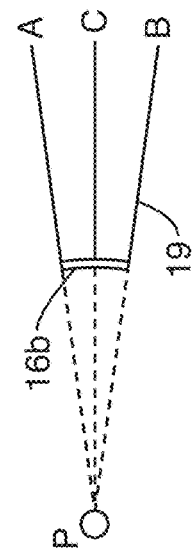
FIG. 9 shows an arcuate transducer configured to generate a diverging beam.

Referring to FIG. 8 and FIG. 9, the transducer 16 may either be flat or circular, and the surface of the transducer element 16 may either be flat, as in transducer 16a in FIG. 8, or arcuate in shape, as shown in transducer 16b of FIG. 9. The flat transducer 16a of FIG. 8 generates a collimated beam 17, whereas the curvilinear transducer 16b of FIG. 9 has a focal point P that is behind the emitting surface to generate a diverging beam 19 (defocused or lens configuration preferably in the y-z plane) across a field of view from A to B (centered on C). The curvilinear transducer 16b of FIG. 9 helps get a 3-D volume while scanning, and is particularly useful with line arrays such as those in FIG. 5, FIG. 10, FIG. 11, and FIG. 13.

In one embodiment, exemplary dimensions for the arrays 14a and 14b and transducers 16 are as follows: a length inside the water tank along X-axis (the horizontal direction) of 16 inches, with 19.2 inches along Y-axis (the horizontal direction) and 16 inches in height along Z-axis (the vertical direction). The distances from the ends of the ultrasound phased transducer arrays 14a and 14b to the inside walls of the water tank along X-axis are approximately 3.8425 inches. In one embodiment, the horizontal distance between the front surfaces of the two parallel phased ultrasound transducer arrays can be adjusted from 12 cm to 25 cm, with a 1 cm increment utilizing 14 different sets of spacer blocks. The accuracy and precision of the horizontal position is ideally 5 microns or better. The vertical travel (Z axis) of the two parallel ultrasound phased transducer arrays 14a and 14b is 10 inches from the top surface of the water level. The vertical travel step interval can be adjusted to any value, such as 0.25 mm, 0.5 mm, 1 mm, and 2 mm.

In one embodiment, array 14a, 14b parameters are as follows: center frequency of 1.5 MHz, bandwidth of ~80% bandwidth (−6 dB) (measured for two-way sound propagation energy), the open angle of ultrasound waves emitting from a single element at ~80°, with uniform transducer elements 16 (<1 dB variation, and uniform bandwidth for one-way sound propagation energy).

In one embodiment, the arrays 14a, 14b comprise 1.5 MHz arrays with 384 elements each, equally spaced along the array. In one example, the dimensions/characteristics of the transducer elements are as follows: elevation aperture: 15 mm, element width: 0.4 mm for 1.5 MHz arrays, elevation focus: 10 cm away from the transducer element, with all transducers configured to be aligned along the array and perpendicular to the elevation plane.

It is appreciated that the above dimensions and configuration details are for reference purposes only, and such characteristics may be varied accordingly.

Figure 6:
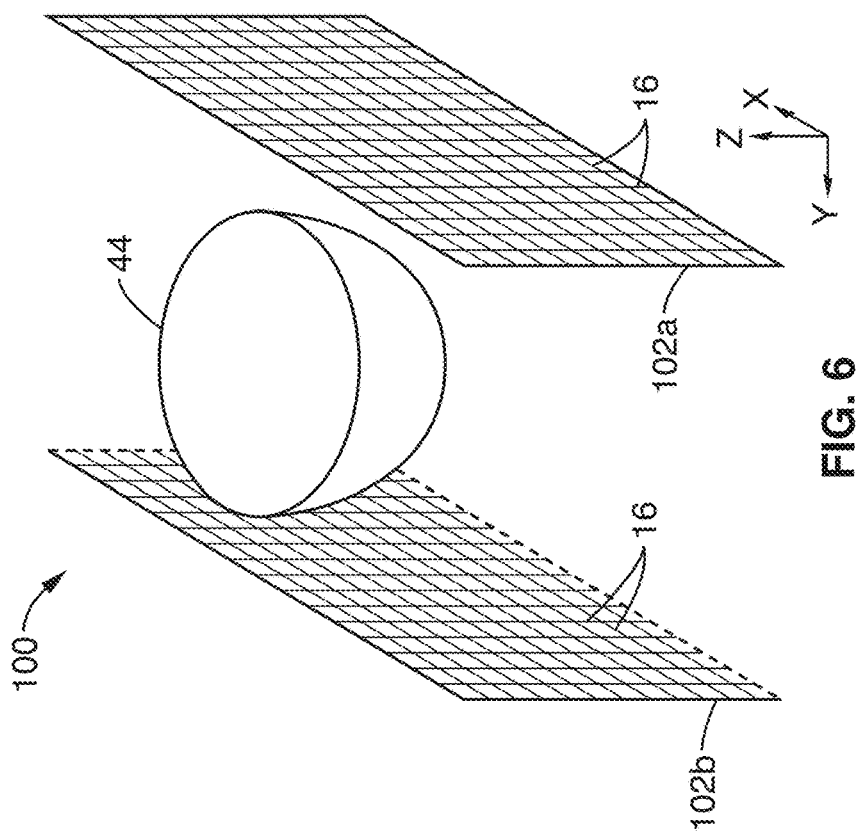
FIG. 6 illustrates a schematic view of a scanner comprising two parallel planar arrays.

The advantage of the configuration of scanner 12, over, e.g. the planar arrays of FIG. 6, is that the system 10 is using a fewer number of transducer elements.

B. Dual Parallel Planar Array Scanner

FIG. 6 illustrates a scanner 100 comprising two parallel planar arrays 102a and 102b aligned opposing each other across the scanning medium 44. Arrays 102a and 102b each comprise matching grids of 2-D arrays of transducers 16 (e.g. transducers 16 share the same locations in their respective x-z planes shown in FIG. 6). With the planar arrays the scanner 100 generally does not need to be translated in the z (vertical) direction.

There are generally two limitations for the synthetic-aperture breast ultrasound tomography with the cylindrical or circular transducer arrays: (a) it is difficult to image the axillary region of the tissue 44; and (b) one size of the cylindrical or circular transducer array will either be undersized or oversized for most sizes of the breast.

Synthetic-aperture breast ultrasound tomography with two parallel planar ultrasound transducer arrays 102a and 102b can overcome these two limitations. As shown in FIG. 6, one planar/2D transducer array 102b can be placed close to the axillary region of the tissue 44. In addition, the distance between the two planar ultrasound transducer arrays 102a and 102b can be adjusted with respect to each other (either manually or with robotic stage 90 as shown in FIG. 5) to fit different sizes of the breast. The ultrasound transducer elements 16 can be in circular or rectangular shape, and the surface of the transducer element can be either flat or arc-shaped, as shown in FIG. 8 and FIG. 9.

C. Cylindrical Array Scanner

Figure 7:
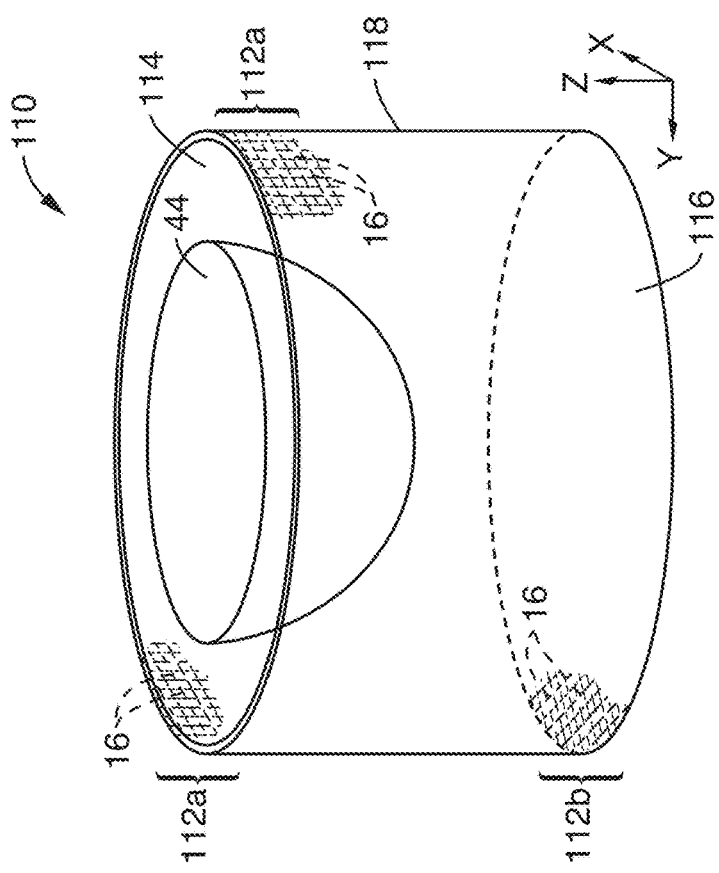
FIG. 7 shows a schematic view of a cylindrical array scanner having a cylindrical 2-D array of transducers and a 2-D planner array at the bottom of the cylinder.

FIG. 7 shows a cylindrical array scanner 110 having a cylindrical 2-D array 112a of transducers 16 in the inside surface of the cylinder wall 118 of the ultrasound transducer array. A planar array of elements 112b may also be positioned on the bottom surface 116 of the cylinder, which would primarily capture backscattered signals.

With the singular cylindrical array scanner 110, a first half of the semi-cylinder elements 16 will be opposed to or facing the second half of the semi-cylinder elements 16, and thus be positioned to receive direct transmission signals 30 (see FIG. 3) at least at varying degrees of angles of incidence. Thus depending on the amount of defocusing within each transducer, a plurality, or all, of the non-emitting transducers 16 will be able to receive a direct transmission signal 30 (FIG. 3) (at varying degrees) from the emitting transducer 16, leading to a full 3D ultrasound tomography image of the breast.

The top end 114 of the cylinder is open, such that the breast tissue 44 is immersed into the cylindrical array scanner 110 with 2D ultrasound transducer elements 16 surrounding the tissue 44. As with previous embodiments, the ultrasound transducer elements 16 can be in circular or rectangular shape, and the surface of the transducer element can be either flat or arc-shaped, as shown in FIG. 8 and FIG. 9.

D. Torroidal (Circular) Array Scanner

FIG. 10 shows a torroidal array scanner 120 having a circular array 122 of transducers 16 aligned in a ring that is configured to encircle the breast 44. A robotic stage 124 may be provided to allow for translation of the array 122 to and scan the breast 44 from the chest wall to the nipple region, slice by slice.

With the singular torroidal array scanner 120, a first half of the semi-circle elements 16 will be opposed to or facing the second half of the semi-circle elements 16, and thus be positioned to receive direct transmission signals 30 (see FIG. 3) at least at varying degrees of angles of incidence. Thus, depending on the amount of defocusing within each transducer, a plurality, or all, of the non-emitting transducers 16 will be able to receive a direct transmission signal 30 (at varying degrees) from the emitting transducer 16.

The circular array 122 preferably comprises defocused lens-transducer elements 16b as shown in FIG. 9, enabling 3-D breast ultrasound tomography. One advantage of the torroidal configuration 120 is using a fewer number of transducer elements compared to the cylindrical transducer array 110.

E. Dual Torroidal (Circular) Array Scanner

FIG. 11. shows another synthetic-aperture ultrasound breast tomography scanner 130 that incorporates use of two circular transducer arrays (upper circular array 132a and lower circular array 132b).

Image resolution depends, at least in part, on ultrasound illumination of the target medium 44. To increase the ultrasound out-of-plane illumination angle, an acoustic diverging lens 16b, as shown in FIG. 9, may be used to widen the elevation beam to the desired level (e.g. between points B and C in the upper circular array 132a and D and E in the lower circular array 132b (conically diverging beam)). Thus, the defocused ultrasound transducer elements 16b transmit ultrasound waves propagating not only to the transducer elements within the same circular array, e.g. between B and C in the upper ring 132a, but also to the other circular transducer array, e.g. between D and E in the lower ring 132b. The upper transducer array 132a may be configured to scan the breast 44 from the chest wall position to the nipple region. At each position, the lower transducer array 132b may move to different vertical position in the z-axis to acquire ultrasound data. This configuration leads to improved vertical resolution of breast ultrasound tomography images compared that obtained using one circular transducer array as shown in FIG. 10.

In practice, the two circular ultrasound transducer arrays 132a and 132b are immersed into the water tank 76 and both encircle the breast 44. One or both arrays 132a and 132b may be configured to translate vertically via a motorized stage 134. For example, during an ultrasound scan, the upper circular array 132a can be positioned against the chest wall, while the lower circular array 132b moves upward from below the nipple region, or vice versa.

As with previous embodiments, each element of one transducer array is fired sequentially, and all elements of both transducer arrays receive ultrasound scattering data 32. The scanner 130 acquires not only ultrasound propagating from one element to all elements within the same transducer array, but also those ultrasound waves propagating from the emitting element to all elements of the other transducer array, leading to a full 3D ultrasound tomography image of the breast.

Such a UST system 130 allows recording of volumetric ultrasound data, and the image resolution limited by slice thickness will be alleviated. In one exemplary design, the data acquisition electronics 18 allow a maximum of 768 parallel channels, so the number of transducers may be halved per array 132a and 132b. The coarser sampling in the plane of the array will be compensated by the cross illuminations The scanner 130 of FIG. 11 can significantly improve image resolution and quality compared to those obtained from an ultrasound tomography system with one circular transducer array. A 3D ultrasound tomography system 10 of this configuration will be operator independent, which is critical for cancer screening, and will be more cost-effective than an ultrasound tomography system with a cylindrical transducer array.

F. Combination 2D Planar and 2D-Arc Array Scanner

Figure 12:
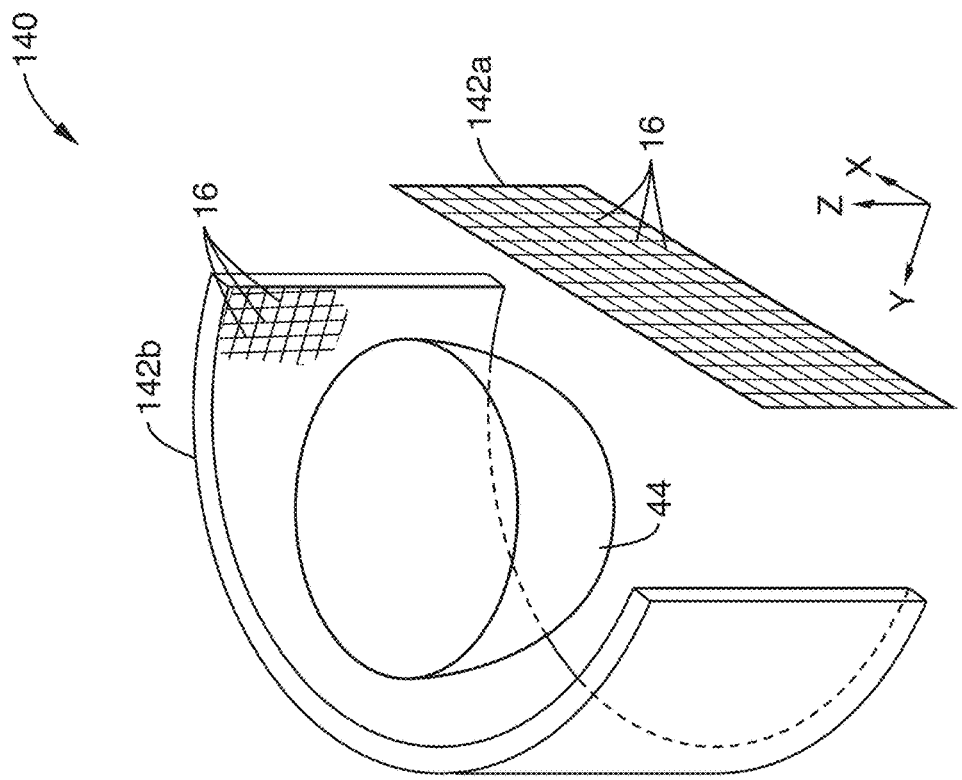
FIG. 12 shows a schematic view of a scanner comprising a semicircular or arcuate array having transducers in an opposing or facing orientation with planar array.

FIG. 12 shows a scanner 140 comprising a semicircular or arcuate array 142b having transducers 16 in an opposing or facing orientation with planar array 142a, with target tissue 44 disposed between the two. The scanner 140 provides a combination of the advantages of the cylindrical transducer array 110 with those of the 2D planner array 100. An ultrasound tomography system 10 with such combination of transducer arrays improves the range of spatial coverage for data acquisition, and the planar array 142 can still be placed near the axillary region.

G. Combination 1D Beam and Arc Array Scanner

Figure 13:
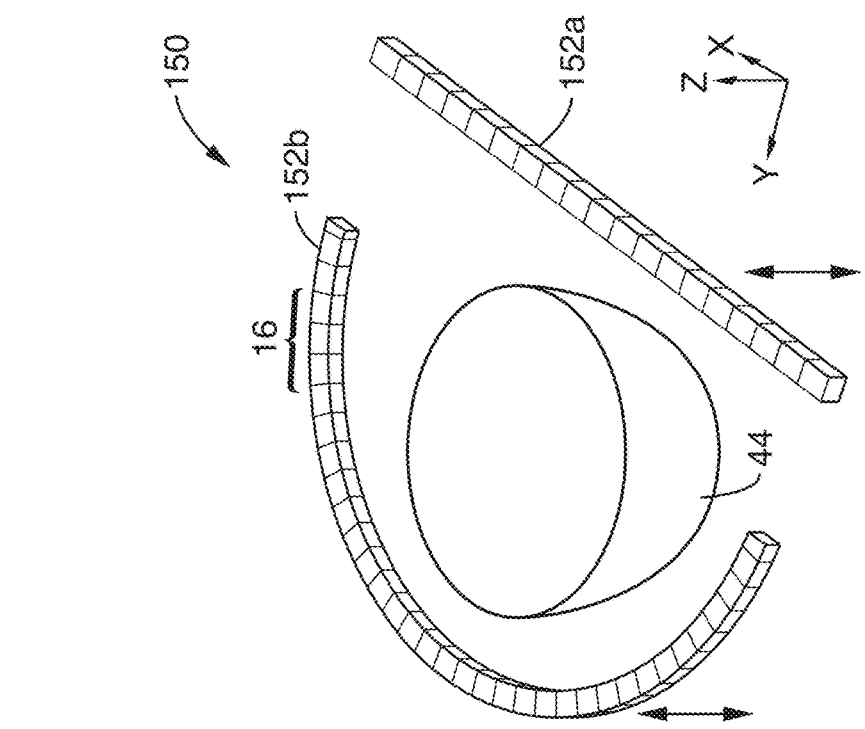
FIG. 13 illustrates a scanner that reduces the 2D arrays in FIG. 12 to 1D arrays.

FIG. 13 illustrates a scanner 150 that reduces the 2D arrays in FIG. 12 to 1D arrays (arcuate line array 152b and linear beam array 152a). This configuration, using a one-dimensional, straight-phased array 152a and a 1D arc-shaped array, 152 reduces the number transducers 16, and thus the number of channels required for data acquisition electronics 18, while improving the spatial coverage of data acquisition compared to when using a two parallel phased transducer array scanner 12 in FIG. 5.

II. Synthetic Aperture Ultrasound Tomography Methods

Referring now to FIG. 14, a flow chart of a synthetic aperture ultrasound tomography method 200 is shown. This method is preferably used with any of the systems and scanners shown in FIG. 1 through FIG. 14, although other scanning systems are contemplated. Ideally, the method is used in conjunction with a scanner that has one or more arrays configured so that a plurality of transducers 16 of an array, or portion of an array, oppose (at a spaced-apart distance across the target scanning medium 44) a plurality of transducers 16 of either another portion of the array, or a separate array, so that reflection and transmission data may be acquired with each successive transducer excitation.

At step 202, the method performs a synthetic aperture ultrasound scan of the tissue medium in accordance with the schematic illustration of scanner 12 FIG. 3. At step 204, reflection and transmission data are simultaneously acquired, as shown in the method 50 of FIG. 4. At step 206, ultrasound waveform tomographic imaging is performed on the acquired reflection and transmission data to generate a high-resolution ultrasound reconstruction image of the target medium 44.

As mentioned previously, a particular shortcoming of existing ultrasound tomographic imaging is that they either use only transmission data, or reflection data only, for image reconstructions. In contrast, the synthetic-aperture ultrasound tomography method 200 of the present invention acquired both ultrasound transmission and reflection data at the same time, and use both ultrasound transmission and reflection data for tomographic reconstructions to greatly improve the shapes and quantitative values of mechanical properties of abnormalities.

FIGS. 15 through 18B demonstrate that using numerical breast-phantom data from ultrasound waveform tomography using both transmission and reflection data simultaneously significantly improves the accuracy of tomographic reconstructions, compared to those obtained using only ultrasound transmission data or only ultrasound reflection data.

Numerical phantom data was generated for a synthetic-aperture ultrasound tomography system with a two parallel phased transducer array scanner 12 as shown in FIG. 5. Each transducer array 14a, 15b is comprised of 384 evenly distributed ultrasound transducer elements, with a pitch size of 0.55 mm. The two transducer arrays were separated by 20 cm. The ultrasound source function used is a Ricker wavelet with a central frequency of 1.0 MHz.

Figure 15:
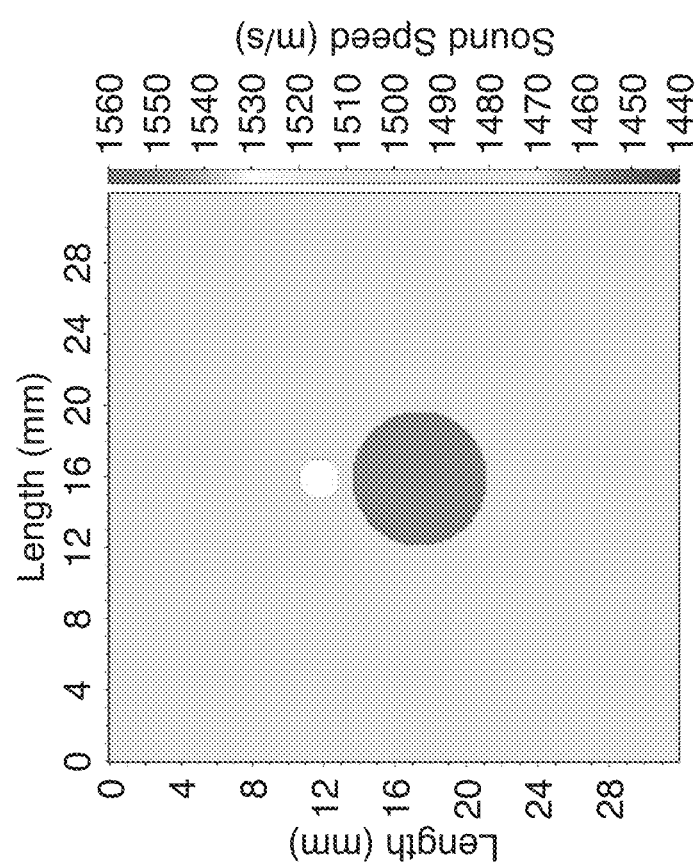
FIG. 15 shows an image of a numerical breast phantom containing two different tumors.

FIG. 15 shows an image of a numerical breast phantom containing two different tumors (small, light tumor, and larger dark tumor). The background sound-speed of the phantom was 1500 m/s, and those of the two tumor speeds were 1530 m/s and 1550 m/s, respectively. The diameters of the tumors were 2.0 mm and 7.0 mm, and approximately 1.3 wavelengths and 4.6 wavelengths. The two tumors were positioned along the longitudinal direction relative to the ultrasound transducer arrays. A high-order finite-difference time-domain wave-equation algorithm in accordance with step 206 was used to compute ultrasound transmission and reflection data.

Figure 16B:
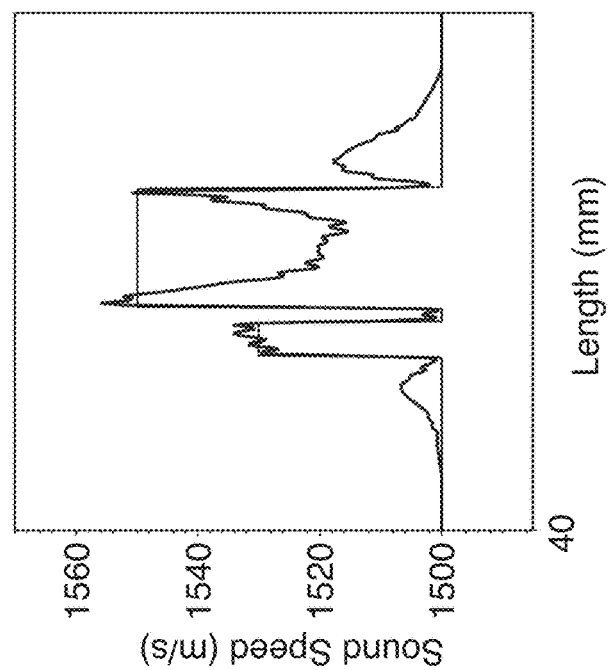
FIG. 16A and FIG. 16B show imaging results (tomographic reconstruction in FIG. 16A, and vertical profile along the center of the tumors in FIG. 16B) obtained using only the reflection data.
Figure 16A:
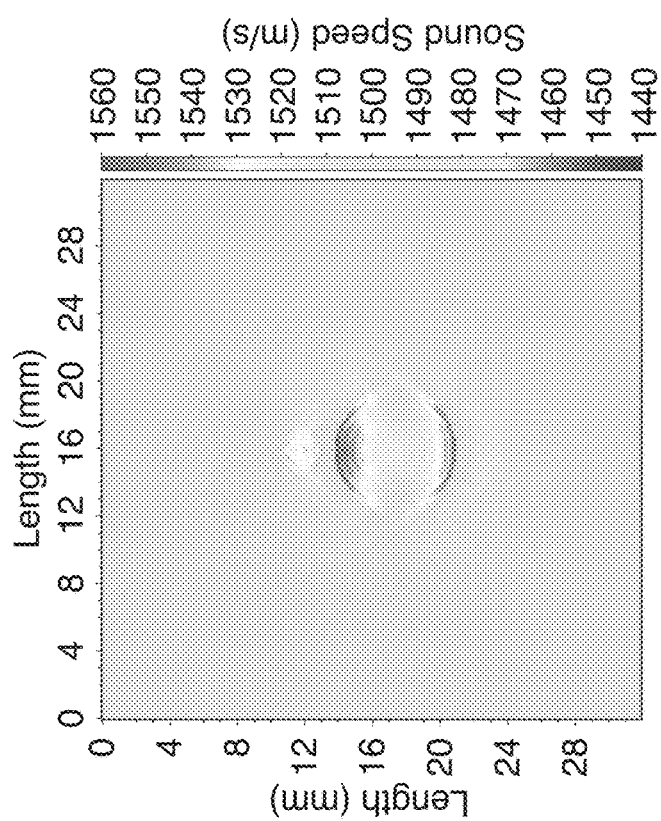
Figure 17B:
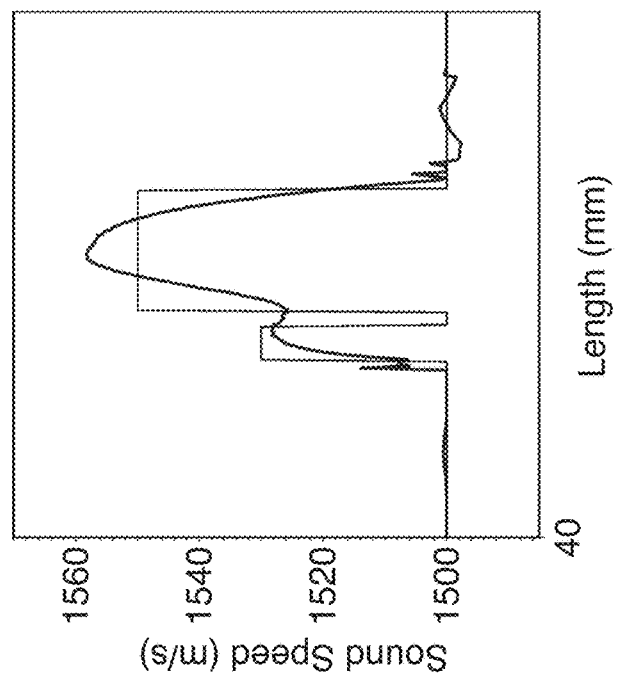
FIG. 17A and FIG. 17B show imaging results (tomographic reconstruction in FIG. 17A, and vertical profile along the center of the tumors in FIG. 17B) obtained using only the transmission data.
Figure 17A:
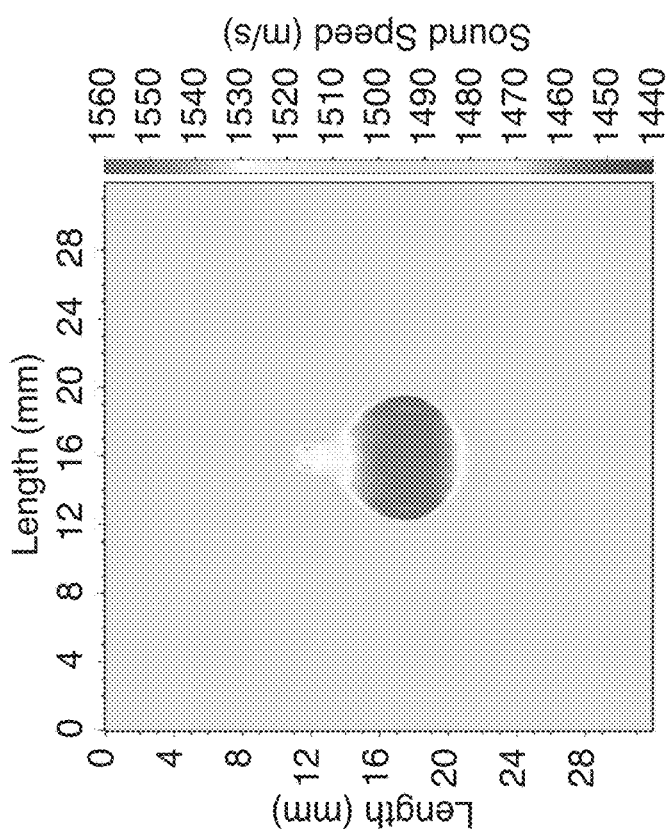
Figure 18B:
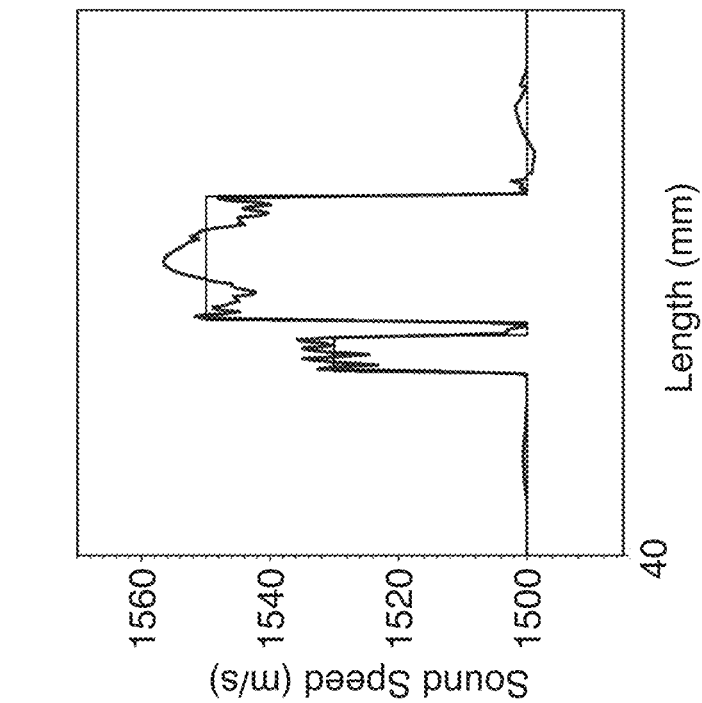
FIG. 18A and FIG. 18B show imaging results (tomographic reconstruction in FIG. 18A, and vertical profile along the center of the tumors in FIG. 18B) obtained using both transmission and reflection data simultaneously in accordance with method of the present invention.
Figure 18A:
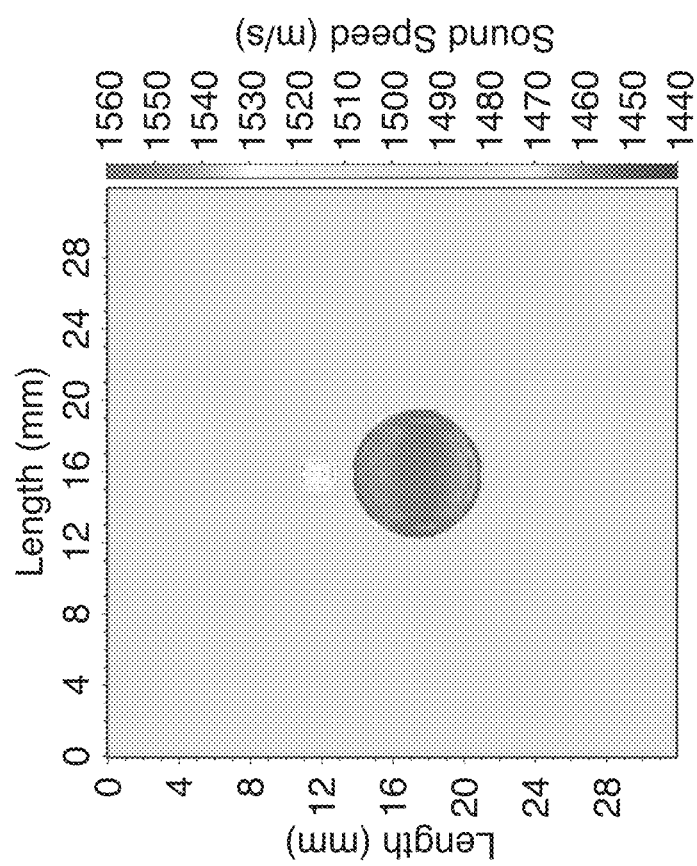

FIG. 16A and FIG. 16B show imaging results (tomographic reconstruction in FIG. 16A, and vertical profile along the center of the tumors in FIG. 16B) obtained using only the reflection data. FIG. 17A and FIG. 17B show imaging results (tomographic reconstruction in FIG. 17A, and vertical profile along the center of the tumors in FIG. 17B) obtained using only the transmission data. FIG. 18A and FIG. 18B show imaging results (tomographic reconstruction in FIG. 18A, and vertical profile along the center of the tumors in FIG. 18B) obtained using both transmission and reflection data simultaneously in accordance with method 200.

The waveform tomographic reconstruction using only the reflection data (FIG. 16A and FIG. 16B) provides mostly the edge information of the tumors, and can distinguish the two tumors.

On the other hand, the waveform tomographic reconstruction (FIG. 17A and FIG. 17B) using only the transmission data gives mostly low spatial-wavenumber components of the tumors, and it is almost impossible to separate the two tumors.

By contrast, the waveform tomographic reconstruction using both the transmission and reflection data simultaneously (FIG. 18A and FIG. 18B) takes the advantages of the above two kinds of tomographic reconstructions, and produces an image with much improved tumor edges and sound-speed reconstructions.

A. Synthetic Aperture Ultrasound Waveform Tomography

Figure 19:
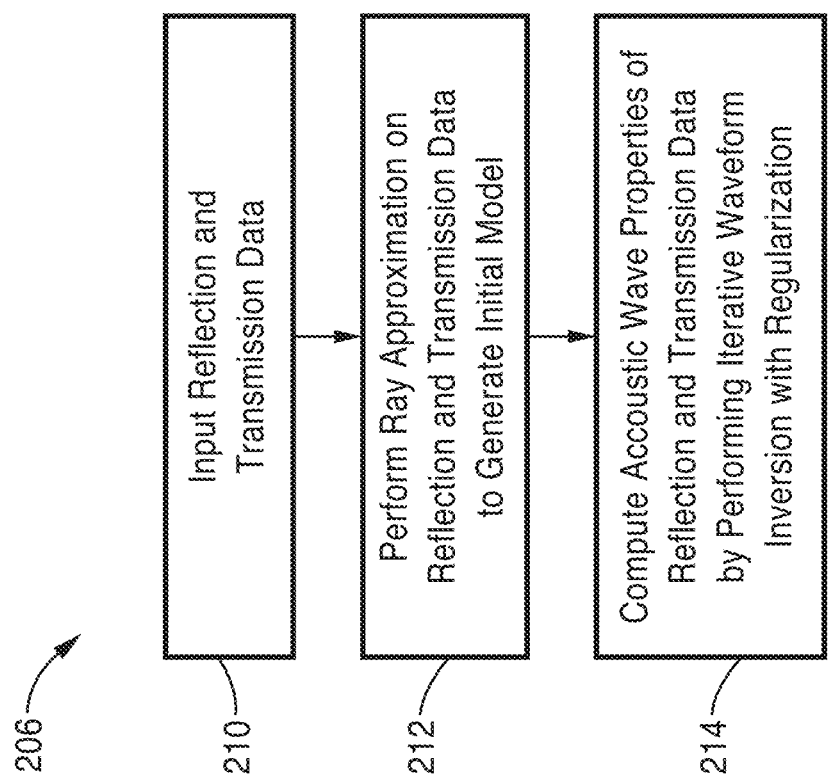
FIG. 19 illustrates a method for generating the ultrasound waveform with regularization using both transmission and reflection data for ultrasound waveform tomography.

FIG. 19 illustrates a preferred method 206 for generating the ultrasound waveform step of method 200 (FIG. 14) using both transmission and reflection data for ultrasound waveform tomography. As shown in FIG. 19, reflection and transmission data are input at step 210, and ray approximation is performed at step 212 to generate an initial model.

Next at step 214, image reconstruction is performed by computing the wave acoustic wave properties of the data by calculating the mean square difference between the observed and synthetic waveforms. In particular, step 214 is performed by performing iterative waveform inversion with regularization.

Two novel approaches to regularization that are highlighted within the system and method of the present invention are spatially variant regularization, and edge-guided regularization, both of which will be explained in further detail below.

From a more basic level, performing step 214 is achieved by solving the acoustic wave equation of Eq. 1 with the minimization model of Eq. 5.

The acoustic-wave equation in the time-domain is given by:

$$\left[\frac{1}{K(r)}\frac{\partial^2}{\partial t^2} - \nabla \cdot \left(\frac{1}{\rho(r)}\nabla\right)\right]p(r,t) = s(r,t), \quad \text{Eq. 1}$$

where $\rho(r)$ is the density, $K(r)$ is the bulk modulus, $s(t)$ is the source term, and $p(r,t)$ is the pressure field.

The solution to Eq. 1 can be written as:

$$p = f(K,s), \quad \text{Eq. 2}$$

where the function of $f$ is the forward modeling operator. Numerical techniques, such as finite-difference and spectral-element methods, can be used to solve Eq. 2. Let the model parameter be:

$$m = \begin{bmatrix} K \\ s \end{bmatrix}.$$

We can rewrite Eq. 2 as:

$$p = f(m). \quad \text{Eq. 3}$$

For the case of constant density, Eq. 1 becomes:

$$\left(\frac{1}{C^2(r)}\frac{\partial^2}{\partial t^2} - \nabla^2\right)p(r,t) = s(r,t), \quad \text{Eq. 4}$$

where $C(r) = \sqrt{K(r)/\rho(r)}$ is the sound speed, and the model parameter is $m = C(r)$.

The inverse problem of Eq. 3 is posed as a minimization problem such that:

$$E(m) = \min_m \{\|d - f(m)\|_2^2\}, \quad \text{Eq. 5}$$

where $\|d-f(m)\|_2^2$ is the misfit function, d can be either ultrasound reflection data, or ultrasound transmission data, or combined ultrasound reflection and transmission data, and $\|\cdot\|_2$ stands for the $L_2$ norm. The minimization of Eq. 5 comprises solving for a model m that yields the minimum mean square difference between measured and synthetic waveforms.

However, because the measurements have limited coverage, solving Eq. 5 is ill-posed. Moreover, because of the nonlinearity of the function $f$, the solution can be trapped in the neighborhood of a local minimum of the misfit function.

Therefore, a regularization technique is preferably applied to Eq. 5 to alleviate the ill-posedness of the inversion.

I. Synthetic Aperture Ultrasound Waveform Tomography with Spatially Variant Regularization.

Figure 20:
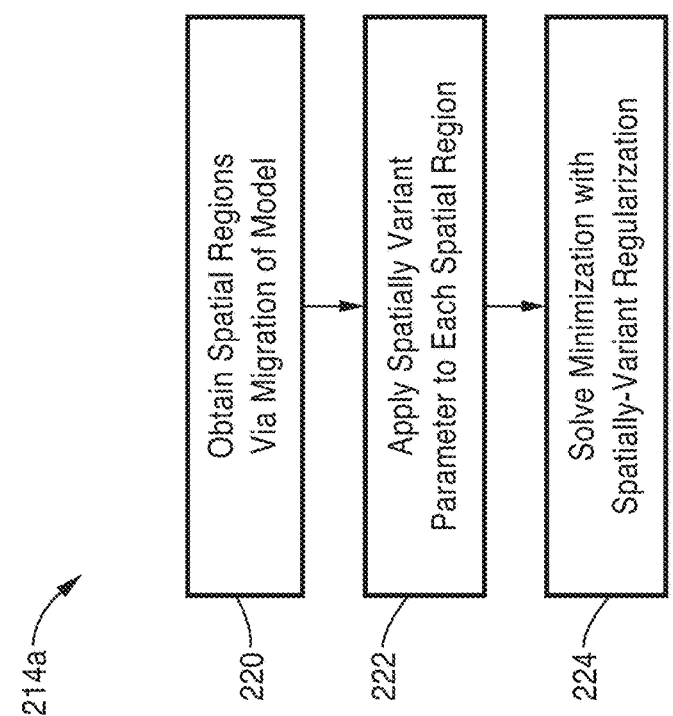
FIG. 20 shows a flow diagram of a method step that is used to apply spatially-variant regularization to perform the computation step of FIG. 19.

FIG. 20 shows a flow diagram of a method step 214a that is used to apply spatially-variant regularization to perform the computation step 214 of FIG. 19.

First, the method 214a obtains spatial regions at step 220. Ray tomography may be performed such that migration results can provide the information about the spatial regions $\Omega_i$ in step 220. Once the approximate locations (and/or approximate size) of the spatial regions $\Omega_i$ are obtained in step 220, a spatially variant parameter $\epsilon_i$ is applied to each of the regions at step 222. Next, at step 224, the minimization equation is solved with the spatially-variant regularization.

It is important to show a general form of spatially-variant regularization derived without specifying the particular regularization term.

A form of regularization is often written as:

$$E(m) = \min_m \{\|d - f(m)\|_2^2 + \lambda R(m)\}, \quad \text{Eq. 6}$$

where R(m) is the regularization term, whose form depends on the type of the regularization invoked. The Tikhonov regularization and the TV regularization are the most commonly used. An equivalent form of regularization can be given as a constrained minimization problem, that is, $$\min_m \{\|d - f(m)\|_2^2\} \quad \text{Eq. 7}$$

subject to $R(m) \leq \epsilon$, where the parameter $\epsilon$ plays the same role as $\lambda$ in Eq. 6 to control the degree of regularization of the desired solution.

To incorporate spatial information into Eq. 7, we modify it as $$\min_m \{\|d - f(m)\|_2^2\} \quad \text{Eq. 8}$$

subject to $R(m_i) \leq \epsilon_i$, $m_i \in \Omega_i$, where $\Omega_i$ is a spatial region, and $\epsilon_i$ is a spatially-variant parameter.

For numerical implementation, Eq. 8 can be written as:

$$E(m) = \min_m \{\|d - f(m)\|_2^2 + \lambda_i R(m_i)\}. \quad \text{Eq. 9}$$

the spatially-variant regularization can also be applied to generate a modified total-variation regularization scheme for ultrasound waveform tomography.

The modified TV regularization is given by:

$$E(m, u) = \min_{m,u} \{\|d - f(m)\|_2^2 + \lambda_1 \|m - u\|_2^2 + \lambda_2 \|\nabla u\|_1\}, \quad \text{Eq. 10}$$

where $\lambda_1$ and $\lambda_2$ are both positive regularization parameters, and u is an auxiliary vector with a dimension equal to m.

Equivalently, the modified TV regularization in Eq. 10 can be written as:

$$E(m, u) = \min_u \{\min_m \{\|d - f(m)\|_2^2 + \lambda_1 \|m - u\|_2^2\} + \lambda_2 \|\nabla u\|_1\}. \quad \text{Eq. 11}$$

An alternating-minimization algorithm is employed for solving the double minimization problem in Eq. 11. Beginning with a starting model $u^{(0)}$, solving for Eq. 11 leads to the solutions of two minimization problems:

$$\begin{cases} m^{(k)} = \underset{m}{\operatorname{argmin}} \|d - f(m)\|_2^2 + \lambda_1 \|m - u^{(k-1)}\|_2^2 \\ u^{(k)} = \underset{u}{\operatorname{argmin}} \|m^{(k)} - u\|_2^2 + \lambda_2 \|\nabla u\|_1 \end{cases} \quad \text{Eq. 12}$$

for $i = 1, 2, \ldots$.

Let $R(m) = \|m - u^{(k-1)}\|_2^2$, following the derivation in the previous section, we therefore obtain the spatially-variant expression of the first minimization in Eq. 12 as:

$$m^{(k)} = \underset{m}{\operatorname{argmin}} \|d - f(m)\|_2^2 + \sum_i \lambda_{1,i} \|m_i - u_i^{(k-1)}\|_2^2. \quad \text{Eq. 13}$$

Similarly, if $R(m) = \|\nabla u\|_1$, we obtain the spatially-variant regularization form for the other minimization problem in Eq. 12 as:

$$u^{(k)} = \underset{u}{\operatorname{argmin}} \|m^{(k)} - u\|_2^2 + \sum_i \lambda_{2,i} \|\nabla u_i\|_1. \quad \text{Eq. 14}$$

A priori information plays an important role in solving inverse problems. The usage of a priori information is usually to avoid the instability during the inversion of data. The a priori information can be some reasonable initial guess of the solution, the smoothness of the desired reconstruction or the spatial information on the solution. In general, the a priori information is functioning as a guide to the true solution.

Spatial information is one type of a priori information. There are different methods to incorporate the a prior information into inversion algorithms. Specifically, we use regularization techniques to incorporate the spatial prior.

For the minimization problems based on Eqs. 13 and 14, both the initial model $m_0$ and spatial regions $\Omega_i$ are needed. The starting model $m_0$ may be obtained from ray tomography. Waveform tomography generally consists of two parts: migration and tomography. Migration yields the shapes (or edges) of the anomalies, and can be obtained in the first few iterations during inversion. Therefore, migration results can provide the information about the spatial regions $\Omega_i$ in step 220.

In a preferred embodiment, the computational methods for solving the modified TV regularization problem are adapted to account for the spatially-variant regularization terms in Eqs. 13 and 14. However, it is appreciated that the spatially variant regularization method 214a may be applied to a more general form of regularization.

From the spatially-variant Tikhonov regularization given in Eq. 13, it is apparent that the gradient of the first term does not change with respect to the spatial information. On the other hand, the second term varies spatially. Therefore, Nonlinear Conjugate Gradient (NCG) is chosen for optimization. The gradient of the first term is obtained using the adjoint-state method given by:

$$\nabla_m \|d - f(m)\|_2^2 = 2\rho(C^{(k)}(r))^2 \sum_{shots} \sum_t \nabla \cdot \vec{u}^{(k)}(r, t) \nabla \cdot \vec{b}^{(k)}(r, t), \quad \text{Eq. 15}$$

where $\vec{u}^{(k)}$ is the forward propagated wavefield, and $\vec{b}^{(k)}$ is the backward propagated residual at iteration k, which is further defined as $r^{(k)} = d^{obs} - f(m^{(k)})$. Therefore, the gradient of the cost function E(m) is:

$$\nabla_m E(m) = 2\rho(C^{(k)}(r))^2 \sum_{shots} \sum_t \nabla \cdot \vec{u}^{(k)}(r, t) \nabla \cdot \vec{b}^{(k)}(r, t) + \quad \text{Eq. 16}$$
$$2 \sum_i \lambda_{1,i}(m_i - u_i^{(k-1)}).$$

The search direction $q^{(k)}$ at iteration k is then defined to be the conjugate to the gradient at the current iteration step. Once the search direction $q^{(k)}$ at iteration k is obtained, the line search with the following Armijo criteria is further used for the optimal step size $\beta^{(k)}$:

$$\begin{cases} E(m^{(k)} + \beta^{(k)} q^{(k)}) & \leq E(m^{(k)}) + c_1 \beta^{(k)} (q^{(k)})^T \nabla E(m^{(k)}), \\ (q^{(k)})^T \nabla E(m^{(k)} + \beta^{(k)} q^{(k)}) & \geq c_2 (q^{(k)})^T \nabla E(m^{(k)}). \end{cases} \quad \text{Eq. 17}$$

When the search direction $q^{(k)}$ and the step size $\beta^{(k)}$ are determined, the update of the current iteration is updated according to Eq. 18:

$$m^{(k+1)} = m^{(k)} + \beta^{(k)} q^{(k)}. \quad \text{Eq. 18}$$

In the following, the computational methods for solving the acoustic wave Eq. 1 via a spatially variant modified TV regularization incorporating the two minimization problems of Eq. 13 and Eq. 14 in accordance with the present invention are shown with reference to FIGS. 21, 22, and 23, in addition to Algorithms 1, 2, and 3 below.

Figure 21:
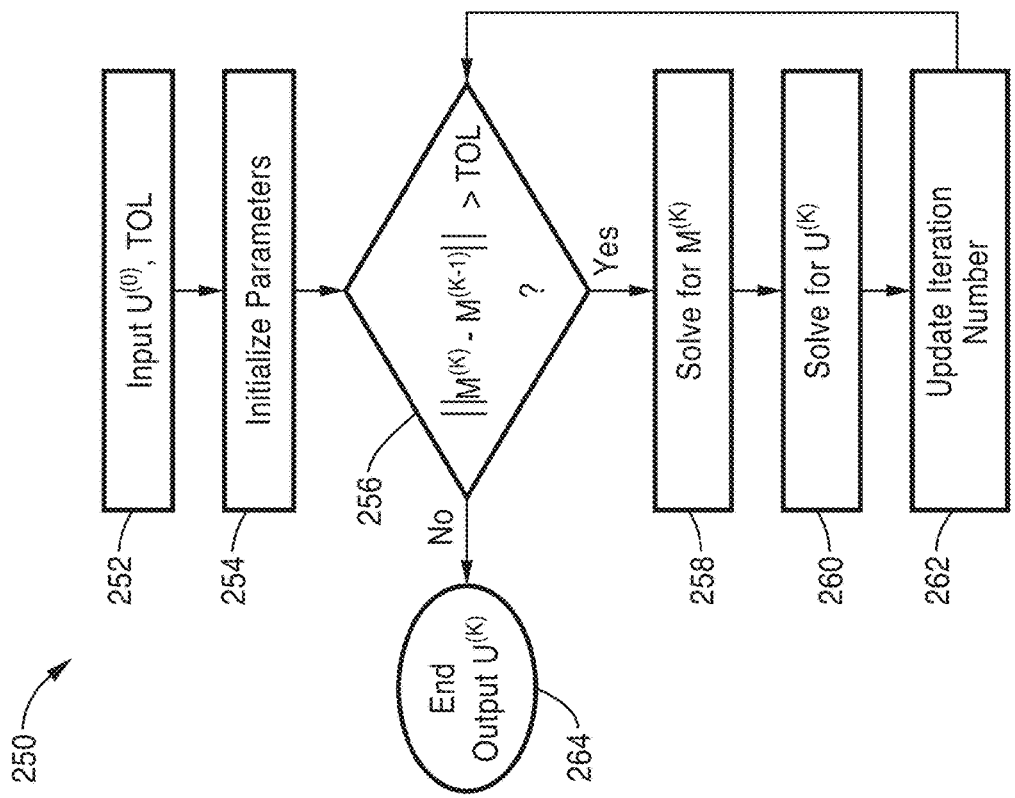
FIG. 21 shows a flow diagram of a computational method for solving the acoustic wave equation via spatially-variant minimization according to Algorithm 1.

Referring to FIG. 21, the computational method 250 for solving Eq. 1 via spatially-variant minimization Eq. 13 and Eq. 14 comprises first inputting the specified tolerance TOL, in addition to the initial model $u^{(0)}$ at step 252. The initial model $u^{(0)}$ may be generated via applying ray approximation step 212 on the input reflection and transmission data 210 as shown in FIG. 19, and further with step 220 in FIG. 20 to obtain spatial regions $\Omega_i$ via migration of the model.

At step 254, the parameters are initialized (e.g. the current iteration value k is set at zero).

A step 256, the algorithm queries whether the current iteration of the model has met the minimum value set by the assigned tolerance TOL.

Figure 22:
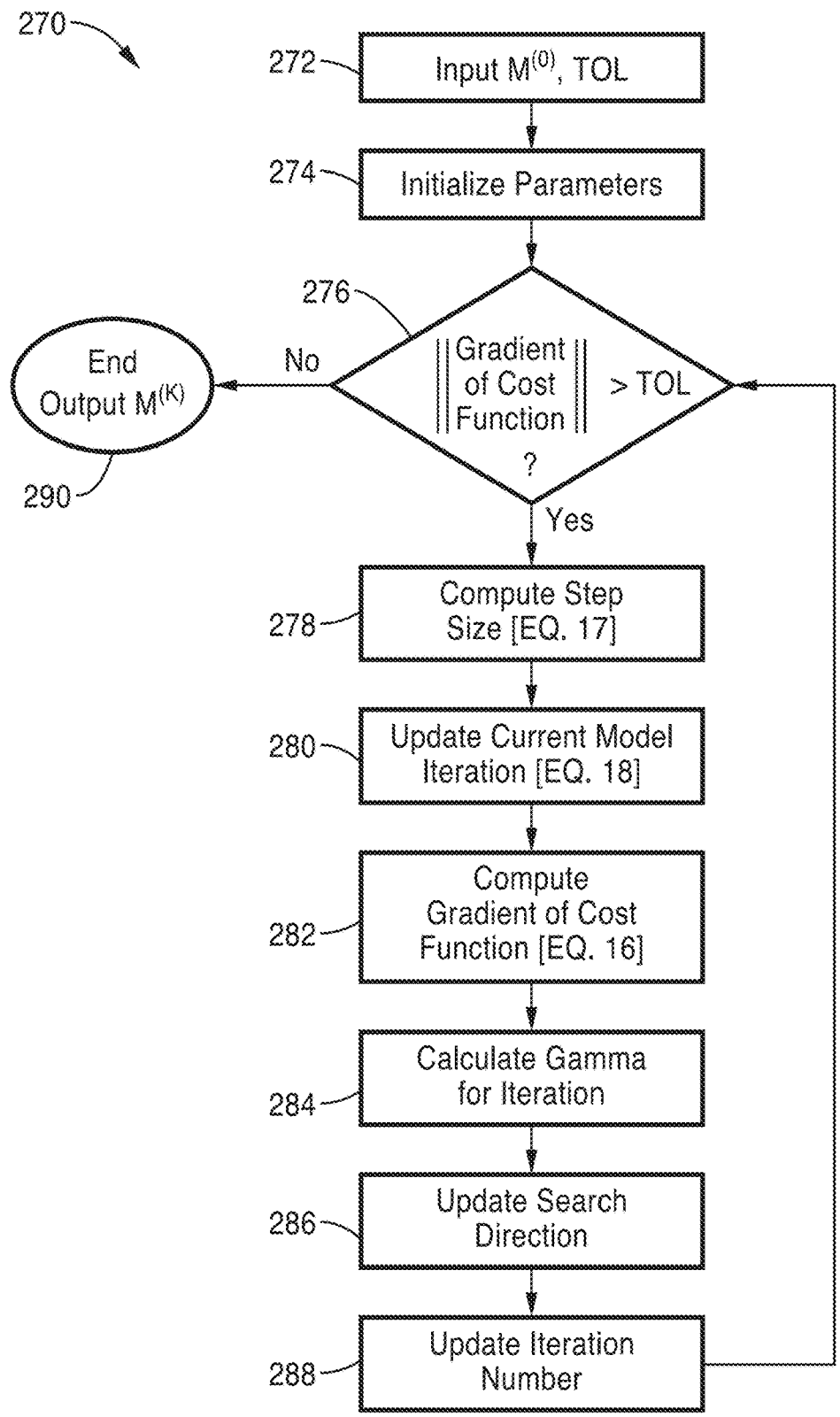
FIG. 22 shows a flow diagram of an algorithm to compute the model according to Algorithm 2.

If the threshold value has not been met, the algorithm, at step 258, solves Eq. 13 to compute $m^{(k)}$ according to Algorithm 1 and method 270 of FIG. 22.

Figure 23:
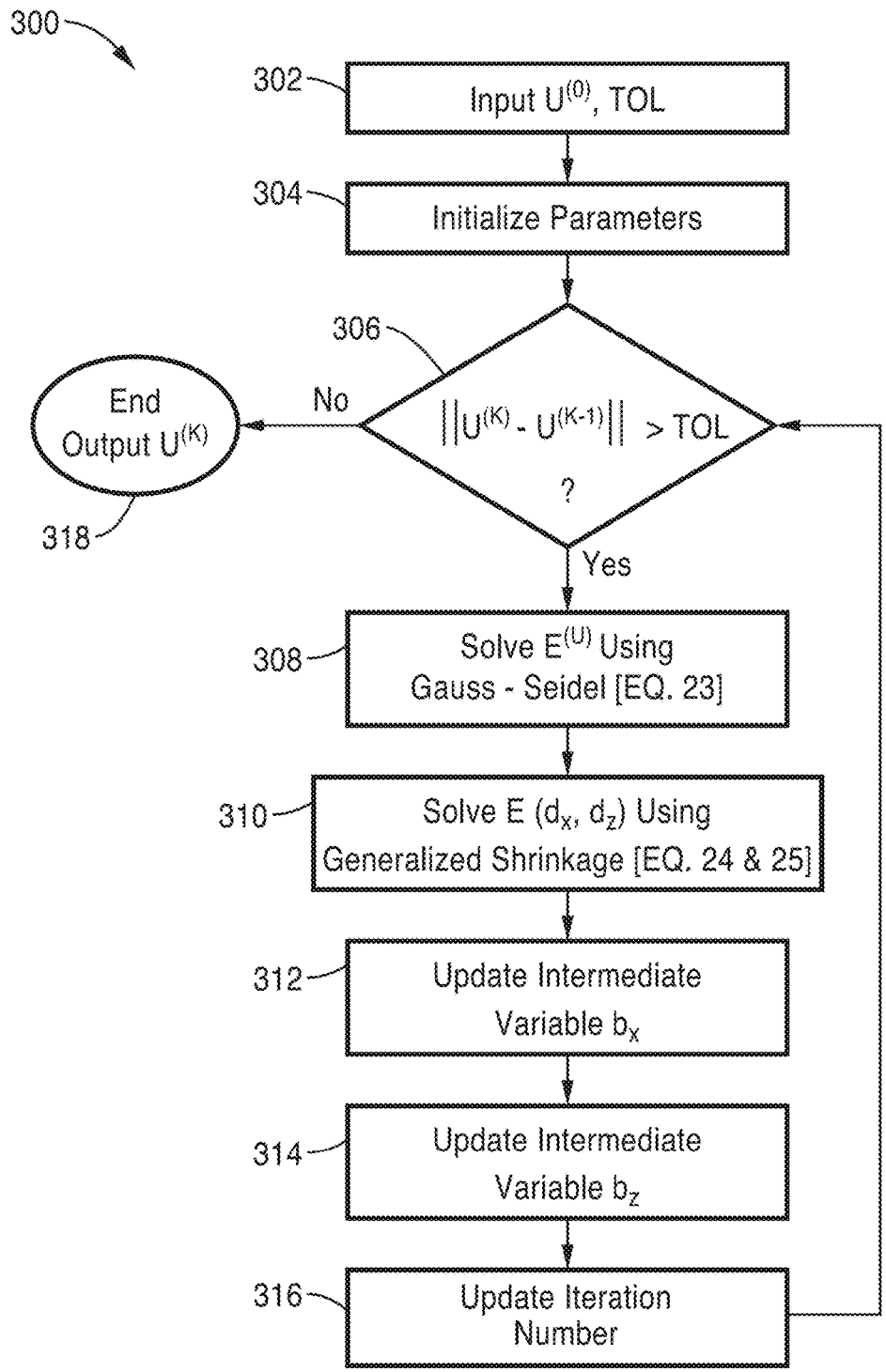
FIG. 23 shows a flow diagram of an algorithm to compute the model according to Algorithm 3.

At step 260, $u^{(k)}$ is computed according to Algorithm 2 and method 300 of FIG. 23. The current iteration value is then updated at step 262, and the routine returns to step 256. If the threshold is met, the algorithm ends and outputs $u^{(k)}$ at step 264. If not, Algorithm 1 continues to iterate.

---

Algorithm 1 Computational method for solving ultrasound waveform tomography with the spatially-variant modified total-variation regularization

---

Input: $u^{(0)}$, TOL
Output: $u^{(k)}$
1: Initialize k = 0 ;
2: while $\{ \| m^{(k)} - m^{(k-1)} \| > \text{TOL} \}$ do
3:   Solve Eq. 13 for $m^{(k)}$ according to Alg. 2;
4:   Solve Eq. 14 for $u^{(k)}$ according to Alg. 3;
5:   Next iteration: k ← k + 1 ;
6: end while

---

The NCG algorithm 270 shown in FIG. 22, used for solving Eq. 14, is also embodied in Algorithm 2 below. The first step in the method 270 is to input the specified tolerance TOL, in addition to the initial model $m^{(0)}$. Other parameters, such as $\lambda_1$ and $\lambda_2$, may also be input in this step. The initial model $m^{(0)}$ may be generated via applying ray approximation step 212 of the input reflection and transmission data 210 as shown in FIG. 19.

At step 274, the parameters are initialized (e.g. the current iteration value k is set at zero).

A step 276, the algorithm queries whether the current iteration of the model has met the minimum value set by the assigned tolerance TOL.

If the threshold value has not been met, the algorithm computes the step size by computing Eq. 17 at step 278.

Next, at step 280, the current iteration model $m^{(k)}$ is updated based on step size $\beta^{(k)}$ and search direction $q^{(k)}$ according to Eq. 18.

At step 282, the gradient of the cost function $\nabla E^{(k+1)}$ is computed according to Eq. 16.

At step 284, the ratio of the inner product of the gradient $\nabla E$ is computed to find the term $\gamma^{(k+1)}$ according to:

$$\gamma^{(k+1)} = \frac{\langle \nabla E^{(k+1)}, \nabla E^{(k+1)} \rangle}{\langle \nabla E^{(k)}, \nabla E^{(k)} \rangle}.$$

Finally, the search direction $q^{(k)}$ is updated at step 286 according to:

$$q^{(k+1)} = -\nabla E^{(k+1)} + \gamma^{(k+1)} q^{(k)}.$$

The current iteration value k is then updated at step 288, and the process repeated at step 276.

If the threshold tolerance has been met at step 276, then the process ends, and outputs the model $m^{(k)}$ at step 290. If not, the process continues to iterate until it does.

---

Algorithm 2:
Canonical NCG to solve $\min_m E(m)$

---

Input: $m^{(0)}$, TOL
Output: $m^{(k)}$
1:   Initialize k = 0, $E^{(0)} = E(m^{(0)})$, $E^{(0)} = \nabla E(m^{(0)})$, and $q^{(0)} = \nabla E^{(0)}$;
2:   while $\{ \|\nabla E^{(k)}\| > \text{TOL}\}$ do
3:     Compute the step size $\beta^{(k)}$ satisfying Eq. (17);
4:     Update the solution according to Eq. (18);
5:     Compute the gradient $\nabla E^{(k+1)}$ based on Eq. (16);
6:     Compute the ratio of the inner product of the gradient $\nabla E$:

$$\gamma^{(k+1)} = \frac{\langle \nabla E^{(k+1)}, \nabla E^{(k+1)} \rangle}{\langle \nabla E^{(k)}, \nabla E^{(k)} \rangle};$$

-continued

Algorithm 2:
Canonical NCG to solve $\min_m E(m)$

7:   Update the search direction: $q^{(k+1)} = -\nabla E^{(k+1)} + \gamma^{(k+1)} q^{(k)}$;
8:   Next iteration: k ← k + 1;
9:   end while While there are many numerical methods for solving the $L_2$-TV problem described in Eq. 25, the split-Bregman method approach was found to be appropriate.

For ultrasound waveform tomography with the spatially-variant regularization, we need to modify the original Split-Bregman iteration algorithm developed for solving the global regularization.

The basic idea of the Split-Bregman method is to reformulate Eq. 14 as an equivalent minimization problem based on the Bregman distance:

$$E(u, g_x, g_z) = \min_{u, g_x, g_z} \|u - m^{(k)}\|_2^2 + \sum_i \lambda_{2,i} \|u_i\|_{TV} + \sum_i \mu_i \|g_{x,i} - \nabla_x u_i - b_{x,i}^{(k)}\|_2^2 + \sum_i \mu_i \|g_{z,i} - \nabla_z u_i - b_{z,i}^{(k)}\|_2^2, \quad \text{Eq. 19}$$

where $g_{x,i}^{(k)} = \nabla_x u_i^{(k)},\ g_{z,i}^{(k)} = \nabla_z u_i^{(k)}$, $b_{x,i}^{(k+1)} = b_{x,i}^{(k)} + (\nabla_x u_i^{(k+1)} - g_{x,i}^{(k+1)})$, $b_{z,i}^{(k+1)} = b_{z,i}^{(k)} + (\nabla_z u_i^{(k+1)} - g_{z,i}^{(k+1)})$, and $\mu_i = 2\lambda_{2,i}$.

This equation becomes more complicated than the original one, because of the fact that spatially-variant regularization parameters are now taken into consideration. To solve this minimization problem, an alternating minimization algorithm in Eq. 19, leading to the following two minimization subproblems:

$$E(u) = \min_u \|u - m^{(k)}\|_2^2 + \sum_i \mu_i \|g_{x,i}^{(k)} - \nabla_x u_i - b_{x,i}^{(k)}\|_2^2 + \sum_i \mu_i \|g_{z,i}^{(k)} - \nabla_z u_i - b_{z,i}^{(k)}\|_2^2, \quad \text{Eq. 20}$$

and $$E(g_x, g_z) = \min_{g_x, g_z} \sum_i \lambda_{2,i} \|u_i\|_{TV} + \sum_i \mu_i \|g_{x,i} - \nabla_x u_i - b_{x,i}^{(k)}\|_2^2 + \sum_i \mu_i \|g_{z,i} - \nabla_z u_i - b_{z,i}^{(k)}\|_2^2. \quad \text{Eq. 21}$$

Applying the optimality condition to Eq. 20, we have:

$$u^{(k+1)} - \sum_i \mu_i \Delta u_i^{(k+1)} = m^{(k)} + \sum_i \mu_i \nabla_x^T (g_{x,i}^{(k)} - b_{x,i}^{(k)}) + \sum_i \mu_i \nabla_z^T (g_{z,i}^{(k)} - b_{z,i}^{(k)}), \quad \text{Eq. 22}$$

which is solved using the Gauss-Seidel iterative method:

$$u_{m,n}^{(k)} = \frac{\mu_i}{1 + 4\mu_i} \left( u_{m+1,n}^{(k)} + u_{m-1,n}^{(k)} + u_{m,n+1}^{(k)} + u_{m,n-1}^{(k)} + g_{x,m-1,n}^{(k)} - g_{x,m,n}^{(k)} + g_{z,m,n-1}^{(k)} - g_{z,m,n}^{(k)} - b_{x,m-1,n}^{(k)} + b_{x,m,n}^{(k)} - b_{z,m,n-1}^{(k)} + b_{y,m,n}^{(k)} \right) + \frac{1}{1 + 4\mu_i} m_{m,n}^{(k)}. \quad \text{Eq. 23}$$

Equation 21 is solved explicitly using a generalized shrinkage formula:

$$g_{x,i}^{(k+1)} = \max(s_i^{(k)} - \lambda_{2,i}/2\mu_i, 0) \frac{\nabla_x u_i^{(k)} + b_{x,i}^{(k)}}{s_i^{(k)}}, \quad \text{Eq. 24}$$

and $$g_{z,i}^{(k+1)} = \max(s_i^{(k)} - \lambda_{2,i}/2\mu_i, 0) \frac{\nabla_z u_i^{(k)} + b_{z,i}^{(k)}}{s_i^{(k)}}, \quad \text{Eq. 25}$$

where $$s_i^{(k)} = \sqrt{|\nabla_x u_i^{(k)} + b_{x,i}^{(k)}|^2 + |\nabla_z u_i^{(k)} + b_{z,i}^{(k)}|^2}.$$

The overall description of the algorithm for solving the ultrasound waveform tomography with the spatially-variant modified total-variation regularization is shown in Alg. 3. The numerical algorithm 300 of FIG. 26 for solving Eq. 14 using the split-Bregman iteration scheme is also provided in Algorithm 3.

The first step in the method 300 (FIG. 23) is to input the specified tolerance TOL, in addition to the initial model in addition to the initial model $u^{(0)}$ at step 302. The initial model $u^{(0)}$ may be generated via applying ray approximation step 212 on the input reflection and transmission data 210 as shown in FIG. 19.

At step 304, the parameters are initialized (e.g. the current iteration value k is set at zero).

A step 306, the algorithm queries whether the current iteration of the model has met the minimum value set by the assigned tolerance TOL.

If the threshold value has not been met, the algorithm solves Eq. 20 using the Gauss-Seidel equation (Eq. 23) at step 308.

At step 310, Eq. 21 is then solved using generalized shrinkage (Eq. 24 and Eq. 25).

Next, the intermediate variable $b_x$ is updated according to $b_x^{(k+1)} = b_x^{(k)} + (\nabla_x u^{(k+1)} - g_x^{(k+1)})$ at step 312.

The intermediate variable $b_z$ is then updated according to $b_z^{(k+1)} = b_z^{(k)} + (\nabla_z u^{(k+1)} - g_z^{(k+1)})$ at step 314.

The current iteration value is then updated at step 316, and the routine returns to step 306. If the threshold is met, the algorithm ends and outputs $u^{(k)}$ at step 318. If not, Algorithm 3 continues to iterate.

Algorithm 3: Split-Bregman iteration

Input: $u^{(0)}$, TOL
Output: $u^{(k)}$
1: Initialize k = 0, $g_x^{(0)} = g_z^{(0)} = b_x^{(0)} = b_z^{(0)} = 0$ ;
2: while { $\| u^{(k)} - u^{(k-1)} \| >$ TOL } do
3:   Solve Eq. (20) according to Eq. (23);
4:   Solve Eq. (21) according to Eq. (24) and Eq. (25);
5:   Update $b_x^{(k+1)} = b_x^{(k)} + (\nabla_x u^{(k+1)} - g_x^{(k+1)})$ ;

Algorithm 3: Split-Bregman iteration

6: Update $b_z^{(k+1)} = b_z^{(k)} + (\nabla_z u^{(k+1)} - g_z^{(k+1)})$ ;
7: Next iteration: k ← k + 1 ;
8: end while II. Synthetic Aperture Ultrasound Waveform Tomography with Edge Guided Regularization.

Figure 24:
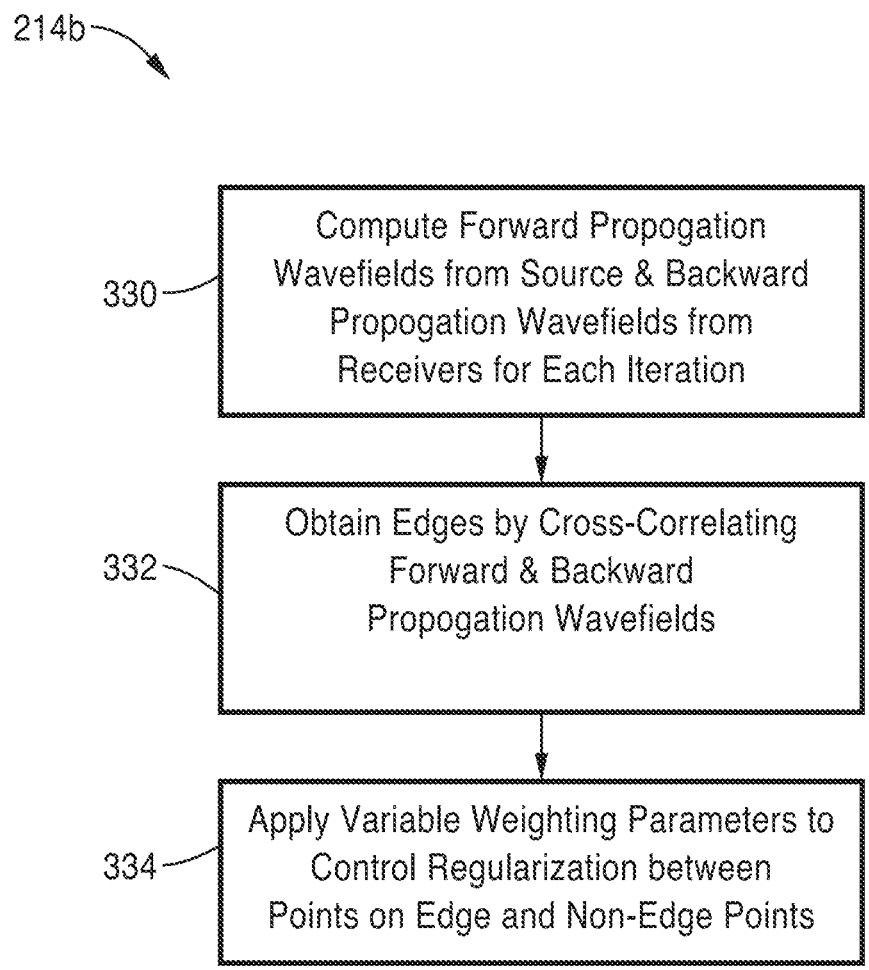
FIG. 24 shows a flow diagram for a computational method for solving the edge-guided regularization scheme of the present invention.

FIG. 24 shows a flow diagram of a method step 214b that is used to apply edge-guided regularization to perform the computation step 214 of FIG. 19.

At step 330, the method 214b computes the forward propagation wavefields from the sources and the backward propagation wavefields from the receivers for each iteration. Next, at step 232, the edges are obtained by cross-correlating the forward and backward wavefields. Finally, variable weighting parameters are applied to control regularization between points residing on an edge and point that are not on the edge (e.g. 0 if on edge, and 1 if not on the edge). This process is described in more detail below, particularly with reference to method 360 of FIG. 25.

The edge-guided regularization method 214b of the present invention may can be incorporated into any regularization scheme. A general form of the edge-guided regularization is provided. In addition, a preferred embodiment is disclosed wherein the edge-guided regularization techniques of the present invention are coupled the modified total-variation regularization for ultrasound waveform tomography. Ideally, the edge-guided regularization techniques of the present invention are used to process data related to transmission and reflection signals, or combination of transmission and reflection signals, of a synthetic aperture ultrasound array. However, it is appreciated that the edge-guided regularization method 214b of the present invention may can be used on data relating to transmission only, or reflection only.

A form of regularization is often written as $$E(m) = \min_{m} \{\|d - f(m)\|_2^2 + \lambda R(m)\}, \quad \text{Eq. 6}$$

where R(m) is the regularization term, whose form depends on the type of the regularization used, and the Tikhonov regularization and the TV regularization are the most commonly used schemes.

To incorporate the edge information, we reformulate the regularization term of R(m) as:

$$R(m) = R(w_{i,j} m) \quad \text{Eq. 26}$$

where the weighting parameter w controls the amount of regularization between neighboring points. We set up the weighting value as the following:

$$w_{i,j} = \begin{cases} 0 & \text{if point}(i, j) \text{ is on the edge} \\ 1 & \text{if point}(i, j) \text{ is not on the edge} \end{cases} \quad \text{Eq. 27}$$

The motivation of assigning a zero weight to the points on the edges is to free them from being penalized by the regularization. The weighting parameter therefore relies on the correct detection of the edge locations, an incorrect weighting value could result in incorrect edges in tomography reconstruction. Therefore, it is crucial to locate the edges as accurate as possible for ultrasound waveform tomography.

The following discussion is relating to the more specific application of edge-guided regularization to ultrasound waveform tomography with the modified total-variation regularization The cost function with the modified TV regularization is given by:

$$E(m, u) = \min_{m,u} \{\|d - f(m)\|_2^2 + \lambda_1 \|m - u\|_2^2 + \lambda_2 \|u\|_{TV}\}, \quad \text{Eq. 28}$$

where $\lambda_1$ and $\lambda_2$ are both positive regularization parameters, u is an auxiliary vector with a dimension equal to m, and the TV regularizer $\|u\|_{TV}$ for a 2D model is defined as the $L_1$:

$$\|u\|_{TV} = \|\nabla u\|_1 = \sum_{1 \leq i,j \leq n} \sqrt{|(\nabla_x u)_{i,j}|^2 + |(\nabla_z u)_{i,j}|^2}, \quad \text{Eq. 29}$$

with $(\nabla_x u)_{i,j} = u_{i+1,j} - u_{i,j}$ and $(\nabla_z u)_{i,j} = u_{i,j+1} - u_{i,j}$.

Neither of the preceding regularizers use any edge information. To incorporate the edge information, we reformulate the conventional TV term given by Eq. 30 as:

$$\|m\|_{ETV} = \|w \nabla m\|_1 = \sum_{1 \leq i,j \leq n} \sqrt{w_{i,j}(|(\nabla_x m)_{i,j}|^2 + |(\nabla_z m)_{i,j}|^2)}, \quad \text{Eq. 30}$$

where w is a weighting parameter

Using the edge-guided TV regularization in Eq. 31, the edge-guided modified TV regularization is given by:

$$E(m, u) = \min_{m,u} \{\|d - f(m)\|_2^2 + \lambda_1 \|m - u\|_2^2 + \lambda_2 \|w \nabla u\|_1\}. \quad \text{Eq. 31}$$

The edge-guided modified TV regularization in Eq. 32 may be written in the form:

$$E(m, u) = \min_{u} \{\min_{m} \{\|d - f(m)\|_2^2 + \lambda_1 \|m - u\|_2^2\} + \lambda_2 \|u\|_{ETV}\}, \quad \text{Eq. 32}$$

An alternating-minimization algorithm is employed to solve the double minimization problem in Eq. 33. Beginning with a starting model $u^{(0)}$, and solving for Eq. 33, leads to the solutions of two minimization problems:

$$\begin{cases} m^{(k)} = \underset{m}{\text{argmin}} \, \|d - f(m)\|_2^2 + \lambda_1 \|m - u^{(k-1)}\|_2^2, \\ u^{(k)} = \underset{u}{\text{argmin}} \, \|m^{(k)} - u\|_2^2 + \lambda_2 \|u\|_{ETV}, \end{cases} \quad \text{Eq. 33}$$

During each iteration step of ultrasound waveform inversion, the forward propagation wavefields from sources and backward propagation wavefields from receivers are computed (see step 330 of FIG. 24). These wavefields are then exploited to obtain the edges of heterogeneities using reverse-time migration, that is, we obtain the edges using the cross-correlation of forward and backward propagation wavefields (see step 332 of FIG. 24). Therefore, we can gain the edge information with only a slightly increased computation time during ultrasound waveform inversion. After the edges are determined, the weighting coefficients is applied according to Eqn. 28 (see step 334 of FIG. 24).

Similar computational and numerical methods for solving ultrasound waveform tomography with the spatially variant modified TV regularization are used to solve the edge-guided modified TV regularization problem in Eq. 34. The problem is decomposed into two separate minimization problems: one canonical Tikhonov regularization, and one edge-guided modified TV regularization, given by:

$$E(m) = \min_{m} \ \|d - f(m)\|_2^2 + \lambda_1 \|m - u^{(k-1)}\|_2^2, \qquad \text{Eq. 34}$$

and $$E(u) = \min_{u} \ \|u - m^{(k)}\|_2^2 + \lambda_2 \|wu\|_{TV}. \qquad \text{Eq. 35}$$

Figure 25:
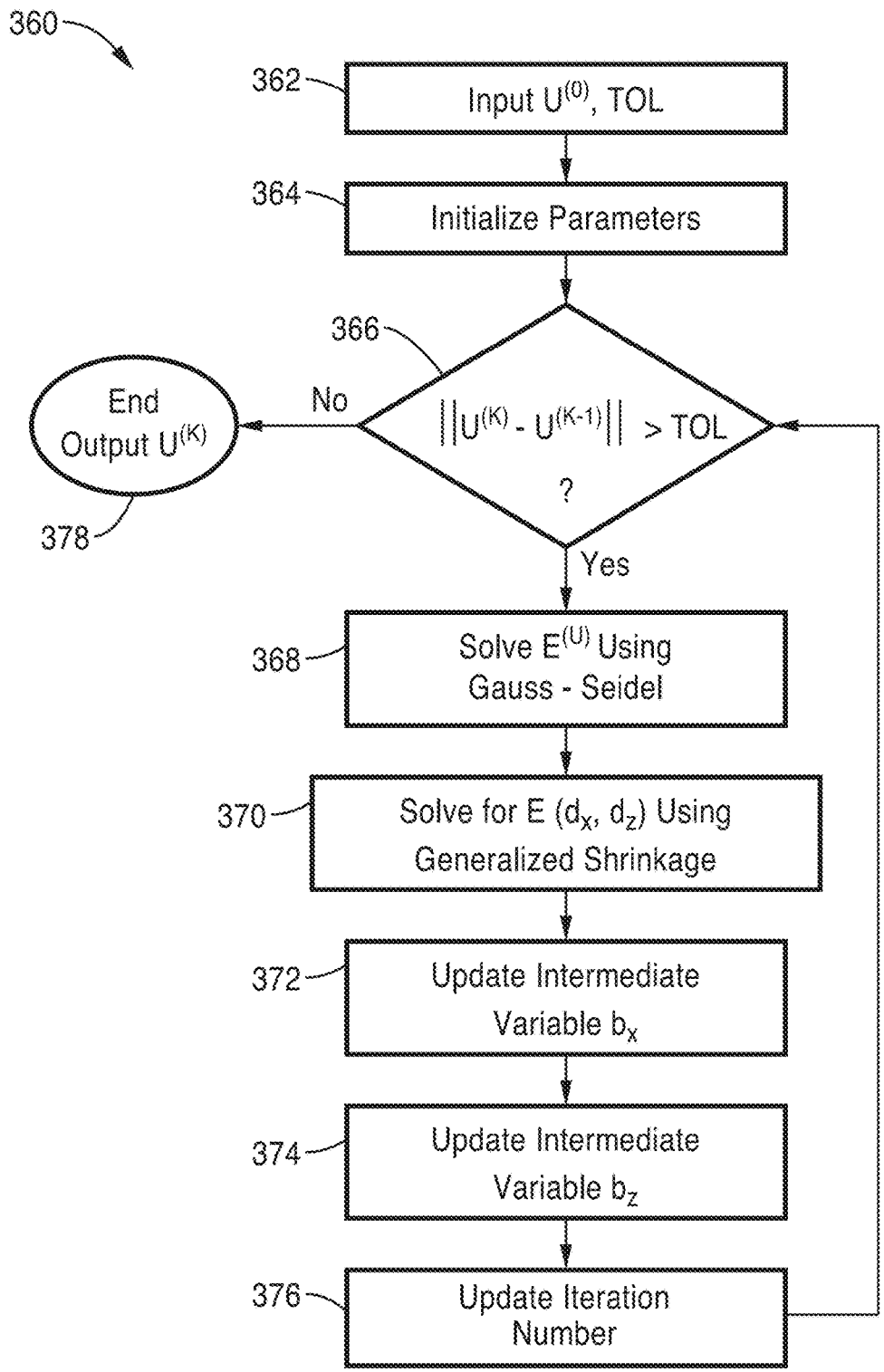
FIG. 25 shows an algorithm using Split Bregman iteration in accordance with Algorithm 4.

The following computational methods for solving these two minimization problems are shown as follows with reference to method 360 of FIG. 25. Additionally, method 250 of FIG. 21 and Algorithm 1, both used for the spatially-variant configuration, may be used to solve for the solving the edge-guided regularization Equations 12, 13.

A Nonlinear Conjugate Gradient (NCG) method for optimization is used to solve Eq. 35. The gradient of the misfit function is:

$$\nabla_m E(m) = \qquad \text{Eq. 36}$$

$$2\rho(C^{(k)}(r))^2 \sum_{shots} \sum_{t} \nabla \cdot \vec{u}^{(k)}(r,t) \nabla \cdot \vec{b}^{(k)}(r,t) + 2\lambda_1(m - u^{(i-1)}),$$

where $\vec{u}^{(k)}$ is the forward propagated wavefield, and $\vec{b}^{(k)}$ is the backward propagated residual at iteration k, defined as $r^{(k)} = d^{obs} - f(m^{(k)})$.

The search direction $q^{(k)}$ at iteration k is then defined to be the conjugate of the gradient at the current iteration step. Once the search direction $q^{(k)}$ at iteration k is obtained, the line search with the Armijo criterion below is used to obtain the optimal step size $\beta^{(k)}$:

$$\begin{cases} E(m^{(k)} + \beta^{(k)} q^{(k)}) & \leq E(m^{(k)}) + c_1 \beta^{(k)} (q^{(k)})^T \nabla E(m^{(k)}) \\ (q^{(k)})^T \nabla E(m^{(k)} + \beta^{(k)} q^{(k)}) & \geq c_2 (q^{(k)})^T \nabla E(m^{(k)}) \end{cases} \qquad \text{Eq. 37}$$

With the search direction $q^{(k)}$ and the step size $\beta^{(k)}$ determined, the update of the current iteration is given by:

$$m^{(k+1)} = m^{(k)} + \beta^{(k)} q^{(k)}. \qquad \text{Eq. 38}$$

The above equations for solving Eq. 35 via NCG may be visualized with reference to method 270 shown in FIG. 22, and Algorithm 2, for the spatially variant regularization model described above.

To solve Eq. 36, the high efficiency of the Split-Bregman iterative method is used and extended for specific use of the edge-guided modified TV regularization problem of the present invention.

In particular, the following equation is obtained where the edge-guided regularization term is taken into account:

$$E(u, g_x, g_z) = \min_{u, g_x, g_z} \ \|u - m^{(k)}\|_2^2 + \lambda_2 \|u\|_{ETV} + \qquad \text{Eq. 39}$$

$$\mu \|g_x - \nabla_x u - b_x^{(k)}\|_2^2 + \mu \|g_z - \nabla_z u - b_z^{(k)}\|_2^2,$$

where $$g_x^{(k)} = \nabla_x u^{(k)}, \ g_z^{(k)} = \nabla_z u^{(k)}, \ b_x^{(k+1)} = b_x^{(k)} + (\nabla_x u^{(k+1)} - g_x^{(k+1)}),$$

and $$b_z^{(k+1)} = b_z^{(k)} + (\nabla_z u^{(k+1)} - g_z^{(k+1)}).$$

An alternating minimization algorithm is then applied to Eq. 39 to minimize two subproblems:

$$E(u) = \min_{u} \ \|u - m^{(k)}\|_2^2 + \qquad \text{Eq. 40}$$

$$\mu \|g_x^{(k)} - \nabla_x u - b_x^{(k)}\|_2^2 + \mu \|g_z^{(k)} - \nabla_z u - b_z^{(k)}\|_2^2,$$

and $$E(g_x, g_z) = \qquad \text{Eq. 41}$$

$$\min_{g_x, g_z} \ \lambda_2 \|u\|_{ETV} + \mu \|g_x - \nabla_x u - b_x^{(k)}\|_2^2 + \mu \|g_z - \nabla_z u - b_z^{(k)}\|_2^2.$$

The edge-guided modified TV regularization of the present invention is thus provided in Eq. 41.

By applying the optimality condition to Eq. 40, i.e., take the derivative of Eq. 40, and set it to be zero, we have:

$$(I - \mu \Delta) u^{(k+1)} = m^{(k)} + \mu \nabla_x^T (g_x^{(k)} - b_x^{(k)}) + \mu \nabla_z^T (g_z^{(k)} - b_z^{(k)}). \qquad \text{Eq. 42}$$

The Gauss-Seidel iterative method is then used to obtain the solution of Eq. 43, given by $$u_{i,j}^{(k)} = \qquad \text{Eq. 43}$$

$$\frac{\mu}{1 + 4\mu} \left( u_{i+1,j}^{(k)} + u_{i-1,j}^{(k)} + u_{i,j+1}^{(k)} + u_{i,j-1}^{(k)} + g_{x,i-1,j}^{(k)} - g_{x,i,j}^{(k)} + g_{z,i,j-1}^{(k)} - \right.$$

$$\left. g_{z,i,j}^{(k)} - b_{x,i-1,j}^{(k)} + b_{x,i,j}^{(k)} - b_{z,i,j-1}^{(k)} + b_{y,i,j}^{(k)} \right) + \frac{1}{1 + 4\mu} m_{i,j}^{(k)}.$$

The generalized shrinkage formula is then used to explicitly solve the edge-guided regularization problem in Eq. 41, and obtain $$g_x^{(k+1)} = \qquad \text{Eq. 44}$$

$$\begin{cases} \max(s^{(k)} - \lambda_2/2\mu, 0) \dfrac{\nabla_x u^{(k)} + b_x^{(k)}}{s^{(k)}}, & \text{for points on edges} \\ \max(\nabla_x u^{(k)} + b_x^{(k)} - \lambda_2/2\mu, 0), & \text{for points not on edges} \end{cases}$$

and $$g_z^{(k+1)} = \qquad \text{Eq. 45}$$

$$\begin{cases} \max(s^{(k)} - \lambda_2/2\mu, 0) \dfrac{\nabla_z u^{(k)} + b_z^{(k)}}{s^{(k)}}, & \text{for points on edges} \\ \max(\nabla_z u^{(k)} + b_z^{(k)} - \lambda_2/2\mu, 0), & \text{for points not on edges} \end{cases}$$

where:

$$s^{(k)} = \sqrt{w(|\nabla_x u^{(k)} + b_x^{(k)}|^2 + |\nabla_z u^{(k)} + b_z^{(k)}|^2)}. \qquad \text{Eq. 46}$$

The numerical algorithm 360 of FIG. 25 for solving Eq. 36 using the split-Bregman iteration scheme is also provided in Algorithm 4 below.

The first step in the method 362 is to input the specified tolerance TOL, in addition to the initial model in addition to the initial model $u^{(0)}$ at step 362. The initial model $u^{(0)}$ may be generated via applying ray approximation step 212 on the input reflection and transmission data 210 as shown in FIG. 19.

At step 364, the parameters are initialized (e.g. the current iteration value k is set at zero).

A step 366, the algorithm queries whether the current iteration of the model has met the minimum value set by the assigned tolerance TOL.

If the threshold value has not been met, the algorithm solves Eq. 40 using the Gauss-Seidel equation (Eq. 43) at step 368.

At step 370, Eq. 21 is then solved using generalized shrinkage (Eq. 44 and Eq. 45).

Next, the intermediate variable $b_x$ is updated according to $b_x^{(k+1)} = b_x^{(k)} + (\nabla_x u^{(k+1)} - g_x^{(k+1)})$ at step 372.

The intermediate variable $b_z$ is then updated according to $b_z^{(k+1)} = b_z^{(k)} + (\nabla_z u^{(k+1)} - g_z^{(k+1)})$ at step 374.

The current iteration value is then updated at step 376, and the routine returns to step 306. If the threshold is met, the algorithm ends and outputs $u^{(k)}$ at step 378. If not, Algorithm 4 continues to iterate.

| Algorithm 4: Split-Bregman iteration |
| --- |
| Input: $u^{(0)}$, TOL |
| Output: $u^{(k)}$ |
| 1: Initialize k = 0, $g_x^{(0)} = g_z^{(0)} = b_x^{(0)} = b_z^{(0)} = 0$ ; |
| 2: while { $\| u^{(k)} - u^{(k-1)} \| >$ TOL } do |
| 3:    Solve Eq. (40) according to Eq. (43); |
| 4:    Solve Eq. (41) according to Eq. (44), (45) and (46); |
| 5:    Update $b_x^{(k+1)} = b_x^{(k)} + (\nabla_x u^{(k+1)} - g_x^{(k+1)})$ ; |
| 6:    Update $b_z^{(k+1)} = b_z^{(k)} + (\nabla_z u^{(k+1)} - g_z^{(k+1)})$ ; |
| 7:    Next iteration: k ← k + 1 ; |

Two groups of numerical examples were generated to validate the feasibility and improvement of our ultrasound waveform tomography with the spatially-variant modified total-variation regularization. Tomographic reconstructions were generated using a globally constant regularization parameter for comparison, and it was demonstrated that algorithm of the present invention resulted in improved resolution.

Synthetic-aperture ultrasound data from two parallel transducer arrays (e.g. similar to scanner 12 of FIG. 5) to test the capability of ultrasound waveform tomography with the spatially-variant modified TV regularization scheme for reconstructing the sound speeds of breast tumors. The result was also compared with that obtained using the modified TV regularization with a constant regularization parameter. Each transducer array comprised 384 evenly distributed transducer elements, with a pitch size of 0.55 mm. The two transducer arrays were separated by 20 cm. The ultrasound source function used was a Ricker wavelet with a central frequency of 1.0 MHz.

Figures 26A, 26B:
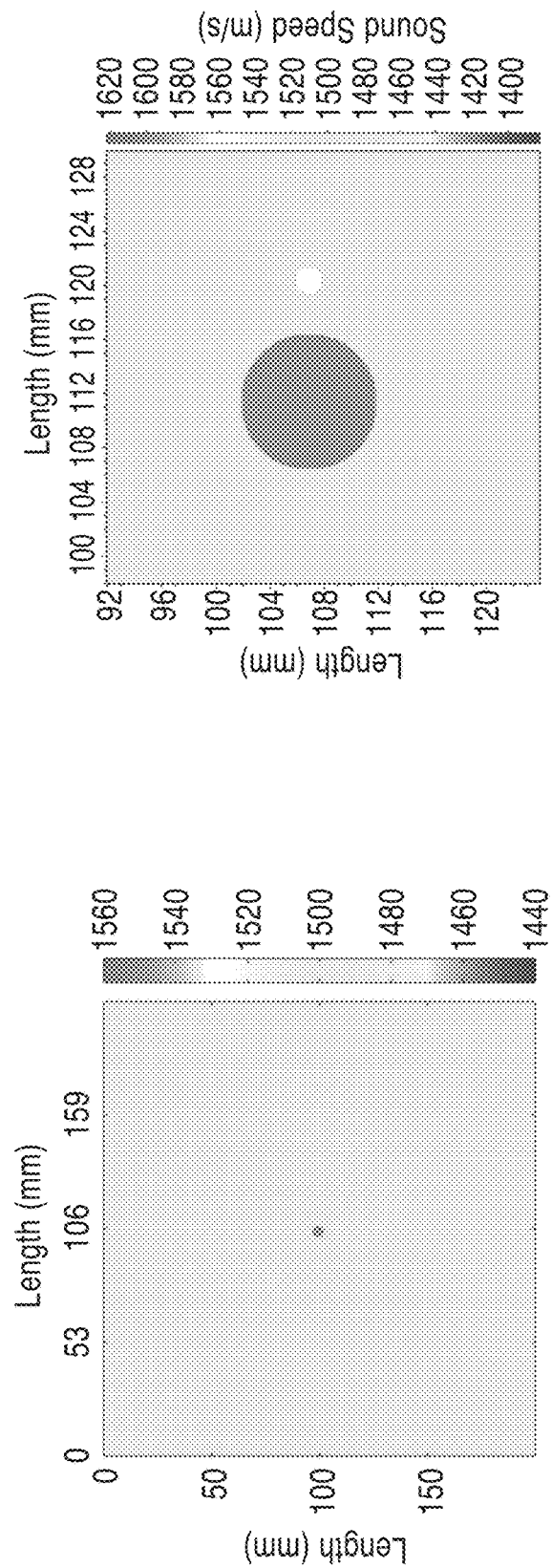
FIG. 26A and FIG. 26B are images showing a numerical breast phantom containing two small breast tumors.

We use a numerical breast phantom, as shown in FIG. 26A and FIG. 26B, to test our new ultrasound waveform tomography method. The size of the phantom is 200×220 mm, which is discretized into a 2000×2200 grid with a grid size of 0.1×0.1 mm. The background sound speed is 1500 m/s. The two circular regions with different sound speeds simulate small breast tumors. Their sound speeds are 1530 m/s and 1550 m/s, and their diameters are 2.0 mm and 10.0 mm, respectively. These diameters represent approximately 1.3 wavelengths and 6.6 wavelengths. To better visualize the tumors, we enlarge the central portion of the phantom in FIG. 26B.

We perform ultrasound waveform tomography using the modified TV regularization with a constant regularization parameter and using the spatially-variant modified TV regularization. The stopping criterion for tomography inversion is either the $L_2$-norm of the gradient is less than $10^{-3}$ or the maximum number of iterations (200) is reached.

Selecting the global regularization parameter according to the reconstruction of the large tumor, we obtain the tomographic reconstruction result shown in FIG. 27A. We notice that the large tumor is reasonably well reconstructed, but the small tumor is not. The sound speed of the small tumor is obviously smaller than its true value. This is because the global regularization parameter is definitely too large for a good reconstruction of the small tumor. On the other hand, if we reduce the global regularization parameter and make it suitable for the tomographic reconstruction of the small tumor, we obtain the result in FIG. 27B. In this situation, the small tumor is very well reconstructed, but the large tumor is poorly reconstructed, leading to those strong artifacts in the upper and lower parts of the large tumor.

We applied the ultrasound waveform tomography with spatially-variant modified TV regularization for the same data, and obtain the reconstruction result in FIG. 26B. Comparing FIG. 27A with 27B, we see that both large and small tumors are well reconstructed. Not only are the edges very well preserved, but also the unwanted artifacts almost completely eliminated. Our new algorithm accurately reconstructs the shapes and locations of both large and small tumors, which are difficult to be obtained using a constant regularization parameter.

To better show the sound speed quantitatively, we plot the vertical and horizontal profiles for FIG. 27A, FIG. 27B and FIG. 27C at three different locations: two at the vertical position of 111 mm and 120 mm, and one at the horizontal position of 107 mm. We notice that the global regularization either yields an over-regularized reconstruction, as seen in FIG. 28A through FIG. 28C or an under-regularized reconstruction, as in FIG. 29A through FIG. 29C. The sound speeds of the tumors lie below their true values. Specifically, for the smaller breast tumor in the over-regularization situation, the reconstruction results in a sound-speed value of 1520 m/s, while the true value is 1530 m/s. For comparison, the reconstructed sound-speed of spatially-variant regularization yields a value that is almost the same to the true value, 1530 m/s. The similar reconstruction accuracy is also true for the results of the large tumor. Therefore, our ultrasound waveform tomography with the spatially-variant modified TV regularization produces a more accurate value of the sound speed than that with the modified TV regularization using a constant regularization parameter.

In the next example, we place the small tumor below the large tumor as shown in FIG. 31A and FIG. 31B. This phantom represents a different challenge for ultrasound waveform tomography. The sizes and sound-speeds of both large and small tumors are the same as in the previous example.

Again we compare the results of our new ultrasound waveform tomography with spatially-variant modified TV regularization with those obtained using ultrasound waveform tomography with the modified TV regularization. FIG. 32A through FIG. 32C illustrates three different reconstructions: two with global regularization and one with spatially-variant regularization. We see that the global regularization degrades the tomographic reconstruction of one or the other tumor because of the over or under-regularization problems. The spatially-variant regularization produces the best tomographic reconstruction among the three.

We also plotted in FIG. 33A through FIG. 33C and FIG. 34A through FIG. 32C the three profiles to quantitatively evaluate the reconstructions, including two horizontal profiles through the center of the two tumors and one vertical profile. From these profiles, we see that the global regularization not only yields inaccurate sound-speeds, but also degrades the edges of the tumors. By contrast, our new method consistently produces accurate tomographic reconstructions of sound speeds and the shapes of both large and small tumors.

Synthetic-aperture ultrasound data from two parallel phased transducer arrays were also used to study the capability of ultrasound waveform tomography with the edge-guided modified TV regularization scheme for reconstructing the sound speeds and shapes of small breast tumors. We compare the results with that obtained using the regular modified TV regularization. The geometry of synthetic-aperture ultrasound tomography system with two parallel phased transducer arrays is schematically illustrated in FIG. 5.

We used two numerical breast phantoms as shown in FIG. 36A and FIG. 36B to test the ultrasound waveform tomography method. The size of the phantom is 200×211 mm, which is discretized into a 2000×2110 grid with a cell size is 0.1×0.1 mm. The background sound speed is 1500 m/s. The sound speed of the tumor in both phantoms is 1565 m/s. The diameter of the first tumor in FIG. 36A is 6 mm, which is approximately four wavelengths of ultrasound. The diameter of the second tumor in FIG. 36C is 1.5 mm, or approximately one wavelength. To better visualize the tumor, we enlarge the central portions of the phantoms and display them in FIG. 36B and FIG. 36D We first compare the reconstruction results of the 6 mm tumor. FIG. 37A through FIG. 37C shows ultrasound waveform tomography results obtained using simulated ultrasound transmission and reflection data. The tomographic reconstruction with the regular modified TV regularization in FIG. 37A shows the tumor is reasonably well reconstructed. However, most parts of the edge of the tumor are actually not well reconstructed to some extent, resulting in unnecessary artifacts and the change of the tumor shape. To better visualize the reconstruction artifacts, we plot in FIG. 37B the difference between the true phantom and the tomographic reconstruction. The major differences occur are around the edge of the tumor.

Figure 38A:
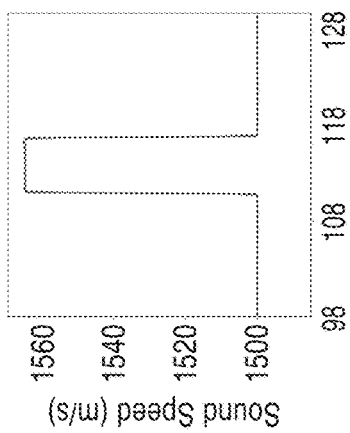
Figure 38B:
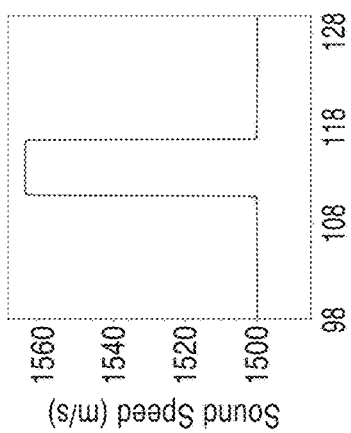
Figure 38C:
Figure 38D:
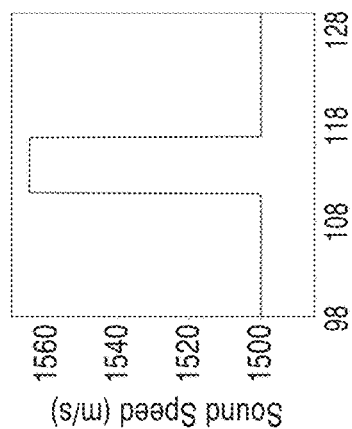
Figure 38E:
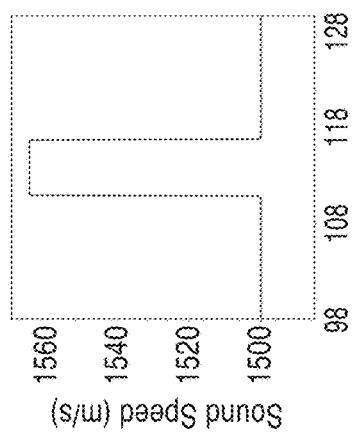
Figure 38F:
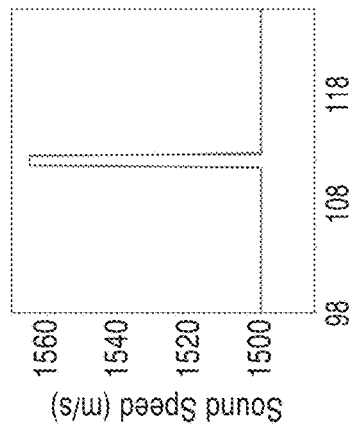

We applied the ultrasound waveform tomography with the edge-guided modified TV regularization to the same data, and obtain the tomographic reconstruction result in FIG. 37C. Comparing FIG. 37C with FIG. 37A, we see that not only the edge of the tumor along all directions is very well preserved in FIG. 37C, but also the size and shape of the reconstruction result are much closer to the true ones. The reconstruction difference from the true phantom is plotted in FIG. 37D, showing that most information of the tumor including the edge are well reconstructed using the edge-guided modified TV regularization. To better visualize the quantitative sound-speed values, we plot profiles in FIG. 38A through FIG. 38F for FIG. 36A and FIG. 36C at three different locations: one at the vertical position of 114 mm (FIG. 38A and FIG. 38D), one at the horizontal position of 108 mm (FIG. 38B and FIG. 38E), and one at the top-right tangent line (FIG. 38C and FIG. 38F). The sound speeds of the reconstructed tumors obtained using both regularization techniques are very close to the true value along the horizontal and vertical directions. However, the reconstructed sound-speed value along the diagonal direction obtained using the regular modified TV regularization is smaller than the true value. By contrast, the reconstructed sound-speed values along all profiles obtained using the edge-guided modified TV regularization are all very close to the true value.

Similarly, we provide the reconstruction results for the 1.5 mm tumor. FIG. 39A through FIG. 39D shows the reconstruction results obtained using ultrasound waveform tomography with the regular modified TV regularization and the edge-guided modified TV regularization. FIG. 40A through FIG. 40F displays the profiles of FIG. 39A through FIG. 39D for quantitative comparison. Again, this numerical example demonstrates that ultrasound waveform tomography with the edge-guided modified TV regularization not only well preserves the edge of a very small tumor along all directions, but also accurately reconstructs the sound speed of the small tumor.

Next, we studied the capability of our ultrasound waveform tomography with the edge-guided modified total-variation regularization for imaging spiculated tumors. We built a numerical breast phantom containing a spiculated tumor as shown in FIG. 41A and FIG. 41B, where FIG. 41A is the whole phantom and FIG. 41B is the central part of the phantom. The diameter of the tumor is 6 mm, and the maximum distance between the ends of the spiculated features is 12 mm. The sound speed of the tumor is 1545 m/s and the background sound speed is 1500 m/s.

We generated ultrasound reflection and transmission data using a finite-difference time-domain wave-equation scheme for the phantom scanned using the synthetic-aperture ultrasound system in FIG. 5. We apply ultrasound waveform tomography with the regular modified TV regularization and with the edge-guided modified TV regularization to the data to perform tomographic reconstructions, and show the results in FIG. 42A through FIG. 42D. FIG. 42A is the tomographic reconstruction image obtained using the regular modified TV regularization, and FIG. 42B depicts the difference between the reconstruction image in FIG. 42A and the true numerical phantom. The main difference or reconstruction error occurs along the edges of the tumor's spiculated features. By contrast, our ultrasound waveform tomography with the edge-guided modified TV regularization produces an improved reconstruction image in FIG. 42C, and its difference from the true numerical phantom shown in FIG. 42D is much smaller than that in FIG. 42B.

We plot in FIG. 43A through FIG. 43F three different profiles for the reconstruction images in FIG. 42A through FIG. 42D: one across the center of the tumor horizontally, one along the center of the tumor vertically, and one close to the right boundary of the tumor vertically. The differences of these profiles are most located along the spiculated features and tumor edges. Ultrasound waveform tomography with the edge-guided modified TV regularization gives more accurate reconstructions of the sound speed and edges of the tumor along all these three profiles than those obtained using ultrasound waveform tomography with the modified TV regularization.

From the discussion above it will be appreciated that the invention can be embodied in various ways, including the following:

1. A synthetic aperture ultrasound tomography imaging method for imaging a tissue medium with one or more ultrasound transducer arrays comprising a plurality of transducers, the method comprising: exciting a first transducer with plurality of transducers to generate an ultrasound field within the tissue medium; acquiring a transmission signal and a reflection signal from a second transducer within the one or more ultrasound transducer arrays; and generating an ultrasound waveform tomography image reconstruction; wherein generating an ultrasound waveform tomography image reconstruction is a function of computing an acoustic wave property of the reflection and transmission signals by calculating a minimum mean square difference between observed and synthetic waveforms relating to the reflection and transmission signals.

2. A method as recited in any of the preceding embodiments, wherein a regularization function is applied to the image reconstruction.

3. A method as recited in any of the preceding embodiments, wherein the image reconstruction is a function of:

$$E(m) = \min_{m} \{\|d - f(m)\|_2^2\},$$

where $\|d-f(m)\|_2^2$ comprises a misfit function, and d comprises data relating to the acquired reflection signal and transmission signal.

4. A method as recited in any of the preceding embodiments, further comprising applying a plurality of spatially-variant parameters to two or more spatial regions within the reconstruction.

5. A method as recited in any of the preceding embodiments, wherein the spatially-variant parameters vary based on a size of the one or more spatial regions.

6. A method as recited in any of the preceding embodiments, further comprising: performing total-variation regularization to generate sound-speed reconstructions of the acquired reflection and transmission signals, and wherein said total-variation regularization is a function of:

$$E(m) = \min_{m} \{\|d - f(m)\|_2^2 + \lambda_i R(m_i)\}$$

and where $\|d-f(m)\|_2^2$ comprises a misfit function, d comprises data relating to the acquired reflection signal and transmission signals, $\lambda_i$ is a positive regularization parameter, and $R(m_i)$ is a spatially-variant regularization term.

7. A method as recited in any of the preceding embodiments, wherein a gradient of the misfit function is obtained using an adjoint state method.

8. A method as recited in any of the preceding embodiments, wherein said spatially-variant regularization comprises a modified total-variation regularization comprising two minimization equations:

$$m^{(k)} = \underset{m}{\operatorname{argmin}} \|d - f(m)\|_2^2 + \sum_{i} \lambda_{1,i} \|m_i - u_i^{(k-1)}\|_2^2.$$

$$u^{(k)} = \underset{u}{\operatorname{argmin}} \|m^{(k)} - u\|_2^2 + \sum_{i} \lambda_{2,i} \|\nabla u_i\|_1.,$$

and where $\|d-f(m)\|_2^2$ comprises a data misfit function, d comprises data relating to the acquired reflection signal and transmission signals, where $\lambda_{1,i}$ and $\lambda_{2,i}$ are both positive regularization parameters, and $u_i$ is an auxiliary variable 9. A method as recited in any of the preceding embodiments, wherein said step of applying a plurality of spatially-variant parameters comprises: obtaining approximate locations of the two or more spatial regions; and applying the plurality of spatially-variant parameters to each of the located two or more spatial regions.

10. A method as recited in any of the preceding embodiments, further comprising using ray tomography migration results to obtain the approximate locations of the two or more spatial regions.

11. A method as recited in any of the preceding embodiments, further comprising assigning a variable weighting parameter to control an amount of regularization between neighboring points.

12. A method as recited in any of the preceding embodiments, wherein said step of assigning a variable weighting parameter comprises: locating an edge of an abnormality within the construction; assigning a first weight to points on the edge; and assigning a second weight to points not on the edge.

13. A method as recited in any of the preceding embodiments, further comprising assigning a weight of zero to points on the edge.

14. A method as recited in any of the preceding embodiments: wherein the one or more transducers comprise source transducers and receiving transducers; and wherein said step of locating an edge comprises: computing forward propagation wavefields from the source transducers and backward propagation wavefields from the receiving transducers; and cross-correlating the forward and backward wavefields.

15. A method as recited in any of the preceding embodiments, further comprising: performing edge-guided regularization to generate sound-speed reconstructions of the acquired reflection and transmission signals, and wherein said edge-guided total-variation regularization is a function of:

$$E(m, u) = \min_{m,u} \{\|d - f(m)\|_2^2 + \lambda_1 \|m - u\|_2^2 + \lambda_2 \|w\nabla u\|_1\},$$

and where $\|d-f(m)_2^2$ comprises a data misfit function, d comprises data relating to the acquired reflection signal and transmission signal, where $\lambda_1$ and $\lambda_2$ are both positive regularization parameters, u is an auxiliary vector, and w is a weighting parameter.

16. A method as recited in any of the preceding embodiments: wherein the plurality of transducers are configured such that a first set of two or more transducers are positioned at an opposing spaced-apart orientation from a second set of two or more transducers such that the first set of two or more transducers face the second set of two or more transducers; wherein the first and second sets of two or more transducers are positioned at spaced-apart locations so as to allow for the tissue medium to be positioned in between the first and second sets of two or more transducers; and wherein the method further comprises: exciting a first transducer with the first set of two or more transducers to generate an ultrasound field within the tissue medium; and receiving a transmission signal and a reflection signal from at least the second set of two or more transducers.

17. A method as recited in any of the preceding embodiments, further comprising receiving a reflection signal from all transducers in the one or more arrays.

18. A method as recited in any of the preceding embodiments, further comprising simultaneously receiving the reflection and transmission signals from the second set of two or more transducers.

19. A synthetic aperture ultrasound tomography imaging system for imaging a tissue medium with one or more ultrasound transducer arrays comprising a plurality of transducers, the system comprising: a processor; and programming executable on said processor and configured for: exciting a first transducer with plurality of transducers to generate an ultrasound field within the tissue medium; receiving a transmission signal and a reflection signal from a second transducer within the one or more ultrasound transducer arrays; and generating an ultrasound waveform tomography image reconstruction; wherein generating an ultrasound waveform tomography image reconstruction is a function of computing an acoustic wave property of the reflection and transmission signals by calculating a minimum mean square difference between observed and synthetic waveforms relating to the reflection and transmission signals.

20. A system as recited in any of the preceding embodiments, wherein a regularization function is applied to the image reconstruction.

21. A system as recited in any of the preceding embodiments, wherein the image reconstruction is a function of:

$$E(m) = \min_{m} \{\|d - f(m)\|_2^2\},$$

where $\|d-f(m)\|_2^2$ comprises a misfit function, and d comprises data relating to the acquired reflection signal and transmission signal.

22. A synthetic aperture ultrasound tomography imaging system as recited in any of the preceding embodiments, wherein said programming is further configured for applying a plurality of spatially-variant parameters to two or more spatial regions within the reconstruction.

23. A system as recited in any of the preceding embodiments, wherein the spatially-variant parameters vary based on a size of the one or more spatial regions.

24. A system as recited in any of the preceding embodiments: wherein said programming is further configured for performing spatially-variant regularization to generate sound-speed reconstructions of the acquired reflection and transmission signals, and wherein said spatially-variant regularization is a function of:

$$E(m) = \min_{m} \{\|d - f(m)\|_2^2 + \lambda_i R(m_i)\}$$

and where $\|d-f(m)\|_2^2$ comprises a data misfit function, d comprises data relating to the acquired reflection signal and transmission signal, $\lambda_i$ is a positive regularization parameter, and $R(m_i)$ is a spatially-variant regularization term.

25. A system as recited in any of the preceding embodiments, wherein said programming is further configured to obtain a gradient of the misfit function using an adjoint state system.

26. A system as recited in any of the preceding embodiments, wherein said total-variation regularization comprises a modified total-variation regularization that is a function of:

$$E(m, u) = \min_{m,u} \{\|d - f(m)\|_2^2 + \lambda_1 \|m - u\|_2^2 + \lambda_2 \|\nabla u\|_1\},$$

and where $\|d-f(m)\|_2^2$ comprises a misfit function, d comprises data relating to the acquired reflection signal and transmission signal, where $\lambda_1$ and $\lambda_2$ are both positive regularization parameters, and u is an auxiliary variable.

27. A system as recited in any of the preceding embodiments, wherein said step of applying a plurality of spatially-variant parameters comprises: obtaining approximate locations of the two or more spatial regions; and applying the plurality of spatially-variant parameters to each of the located two or more spatial regions.

28. A system as recited in any of the preceding embodiments, wherein said programming is further configured to use ray tomography migration results to obtain the approximate locations of the two or more spatial regions.

29. A system as recited in any of the preceding embodiments, wherein said programming is further configured for assigning a variable weighting parameter to control an amount of regularization between neighboring points.

30. A system as recited in any of the preceding embodiments, wherein said step of assigning a variable weighting parameter comprises: locating an edge of an abnormality within the construction; assigning a first weight to points on the edge; and assigning a second weight to points not on the edge.

31. A system as recited in any of the preceding embodiments, wherein said programming is further configured for assigning a weight of zero to points on the edge.

32. A system as recited in any of the preceding embodiments: wherein the one or more transducers comprise source transducers and receiving transducers; and wherein said step of locating an edge comprises: computing forward propagation wavefields from the source transducers and backward propagation wavefields from the receiving transducers; and cross-correlating the forward and backward wavefields.

33. A system as recited in any of the preceding embodiments: wherein said programming is further configured to perform edge-guided regularization to generate sound-speed reconstructions of the acquired reflection and transmission signals, and wherein said edge-guided regularization is a function of:

$$E(m, u) = \min_{m,u} \{\|d - f(m)\|_2^2 + \lambda_1 \|m - u\|_2^2 + \lambda_2 \|w\nabla u\|_1\}$$

and where $\|d-f(m)\|_2^2$ comprises a data misfit function, d comprises data relating to the acquired reflection signal and transmission signal, where $\lambda_1$ and $\lambda_2$ are both positive regularization parameters, u is an auxiliary vector, and w is a weighting parameter.

34. A synthetic aperture ultrasound tomography imaging system as recited in any of the preceding embodiments: wherein the plurality of transducers are configured such that a first set of two or more transducers are positioned at an opposing spaced-apart orientation from a second set of two or more transducers such that the first set of two or more transducers face the second set of two or more transducers; wherein the first and second sets of two or more transducers are positioned at spaced-apart locations so as to allow for the tissue medium to be positioned in between the first and second sets of two or more transducers; and wherein said programming is further configured for: exciting a first transducer with the first set of two or more transducers to generate an ultrasound field within the tissue medium; and receiving a transmission signal and a reflection signal from at least the second set of two or more transducers.

35. A system as recited in any of the preceding embodiments, wherein said programming is further configured for receiving a reflection signal from all transducers in the one or more arrays.

36. A system as recited in any of the preceding embodiments, wherein said programming is further configured for simultaneously receiving the reflection and transmission signals from the second set of two or more transducers.

37. A synthetic aperture ultrasound tomography imaging system for imaging a tissue medium, the system comprising: one or more ultrasound transducer arrays; said one or more ultrasound transducer arrays comprising a plurality of transducers; a processor; and programming executable on said processor and configured for: exciting a first transducer with plurality of transducers to generate an ultrasound field within the tissue medium; receiving a transmission signal and a reflection signal from a second transducer within the one or more ultrasound transducer arrays; and generating an ultrasound waveform tomography image reconstruction; wherein generating an ultrasound waveform tomography image reconstruction is a function of computing an acoustic wave property of the reflection and transmission signals by calculating a minimum mean square difference between observed and synthetic waveforms relating to the reflection and transmission signals.

38. A system as recited in any of the preceding embodiments: wherein the plurality of transducers are configured such that a first set of two or more transducers are positioned at an opposing spaced-apart orientation from a second set of two or more transducers such that the first set of two or more transducers face the second set of two or more transducers; and wherein the first and second sets of two or more transducers are positioned at spaced-apart locations so as to allow for the tissue medium to be positioned in between the first and second sets of two or more transducers.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A synthetic aperture ultrasound tomography imaging method for imaging a tissue medium utilizing a synthetic-aperture ultrasound tomography system comprising two or more ultrasound transducer arrays, the two or more ultrasound transducer arrays being spaced apart from each other, the two or more ultrasound transducer arrays comprising a plurality of transducers, the method comprising:
   exciting a first transducer of the plurality of transducers to generate an ultrasound field within the tissue medium;
   receiving a transmission signal and a reflection signal at a second transducer of the one or more ultrasound transducer arrays; and
   generating an ultrasound waveform tomography image reconstruction, the generating the ultrasound waveform tomography image reconstruction comprising:
      applying a regularization function;
      applying a plurality of spatially-variant parameters to two or more spatial regions within the ultrasound waveform tomography image reconstruction; and
      performing spatially-variant regularization as the regularization function to generate sound-speed reconstructions of the acquired reflection and transmission signals, wherein generating an ultrasound waveform tomography image reconstruction is a function of computing an acoustic wave property of the reflection and transmission signals by calculating a minimum mean square difference between observed and synthetic waveforms, wherein the synthetic waveform is generated from simulated ultrasound transmission and reflection data, wherein the observed waveform is calculated using the reflection and transmission signals, and wherein the image reconstruction is a function of:

$$E(m) = \min_{m} \{\|d - f(m)\|_2^2 + \lambda_i R(m_i)\}$$

where $\|d-f(m)\|_2^2$ comprises a misfit function, d comprises data relating to the acquired reflection signal and transmission signal, $\lambda_i$ is a positive regularization parameter, and $R(m_i)$ is a spatially-variant regularization term.

2. A method as recited in claim 1, wherein the spatially-variant parameters vary based on a size of the one or more spatial regions.

3. A method as recited in claim 1, wherein a gradient of the misfit function is obtained using an adjoint state method.

4. A method as recited in claim 1, wherein said spatially-variant regularization comprises a modified total-variation regularization comprising two minimization equations:

$$m^{(k)} = \underset{m}{\text{argmin}} \|d - f(m)\|_2^2 + \sum_i \lambda_{1,i} \|m_i - u_i^{(k-1)}\|_2^2,$$

$$u^{(k)} = \underset{u}{\text{argmin}} \|m^{(k)} - u\|_2^2 + \sum_i \lambda_{2,i} \|\nabla u_i\|_1,$$

and where $\|d-f(m)\|_2^2$ comprises a data misfit function, d comprises data relating to the acquired reflection signal and transmission signals, where $\lambda_1$ and $\lambda_2$ are both positive regularization parameters, and $u_i$ is an auxiliary variable.

5. A method as recited in claim 4, wherein said step of applying a plurality of spatially-variant parameters comprises:

obtaining approximate locations of the two or more spatial regions; and applying the plurality of spatially-variant parameters to each of the located two or more spatial regions.

6. A method as recited in claim 5, further comprising using ray tomography migration results to obtain the approximate locations of the two or more spatial regions.

7. A synthetic aperture ultrasound tomography imaging system for imaging a tissue medium, the system comprising:

two or more ultrasound transducer arrays, the two or more ultrasound transducer arrays being spaced apart from each other, the two or more ultrasound transducer arrays comprising a plurality of transducers;

a processor; and programming executable on said processor and configured for:

exciting a first transducer of the plurality of transducers to generate an ultrasound field within the tissue medium;

receiving a transmission signal and a reflection signal at a second transducer of the one or more ultrasound transducer arrays; and generating an ultrasound waveform tomography image reconstruction, the generating the ultrasound waveform tomography image reconstruction comprising:

applying a regularization function;

applying a plurality of spatially-variant parameters to two or more spatial regions within the ultrasound waveform tomography image reconstruction; and performing a spatially-variant regularization to generate sound-speed reconstructions of the acquired reflection and transmission signals, wherein generating an ultrasound waveform tomography image reconstruction is a function of computing an acoustic wave property of the reflection and transmission signals by calculating a minimum mean square difference between observed and synthetic waveforms, wherein the synthetic waveform is generated from simulated ultrasound transmission and reflection data, wherein the observed waveform is calculated using the reflection and transmission signals, and wherein the image reconstruction is a function of:

$$E(m) = \min_{m} \{\|d - f(m)\|_2^2 + \lambda_i R(m_i)\}$$

where $\|d-f(m)\|_2^2$ comprises a misfit function, d comprises data relating to the acquired reflection signal and transmission signal, $\lambda_i$ is a positive regularization parameter, and $R(m_i)$ is a spatially-variant regularization term.

8. A system as recited in claim 7, wherein the spatially-variant parameters vary based on a size of the one or more spatial regions.

9. A system as recited in claim 7, wherein said programming is further configured to obtain a gradient of the misfit function using an adjoint state system.

10. A system as recited in claim 9, wherein said spatially-variant regularization comprises a modified total-variation regularization comprising two minimization equations:

$$m^{(k)} = \underset{m}{\text{argmin}} \|d - f(m)\|_2^2 + \sum_i \lambda_{1,i} \|m_i - u_i^{(k-1)}\|_2^2,$$

$$u^{(k)} = \underset{u}{\text{argmin}} \|m^{(k)} - u\|_2^2 + \sum_i \lambda_{2,i} \|\nabla u_i\|_1,$$

and where $\|d-f(m)\|_2^2$ comprises a data misfit function, d comprises data relating to the acquired reflection signal and transmission signals, where $\lambda_{1,i}$ and $\lambda_{2,i}$ are both positive regularization parameters, and $u_i$ is an auxiliary variable.

11. A synthetic aperture ultrasound tomography imaging system for imaging a tissue medium, the system comprising:

one or more ultrasound transducer arrays;

said one or more ultrasound transducer arrays comprising a plurality of transducers;

a processor; and programming executable on said processor and configured for:

exciting a first transducer of the plurality of transducers to generate an ultrasound field within the tissue medium;

receiving a transmission signal and a reflection signal at a second transducer of the plurality of transducers of the one or more ultrasound transducer arrays; and generating an ultrasound waveform tomography image reconstruction, the generating the ultrasound waveform tomography image reconstruction comprising:
applying a regularization function;
applying a plurality of spatially-variant parameters to two or more spatial regions within the ultrasound waveform tomography image reconstruction; and
performing a spatially-variant regularization to generate sound-speed reconstructions of the acquired reflection and transmission signals, wherein generating an ultrasound waveform tomography image reconstruction is a function of computing an acoustic wave property of the reflection and transmission signals by calculating a minimum mean square difference between observed and synthetic waveforms, wherein the synthetic waveform is generated from simulated ultrasound transmission and reflection data, and wherein the observed waveform is calculated using the reflection and transmission signals, and wherein the image reconstruction is a function of:

$$E(m) = \min_{m} \{\|d - f(m)\|_2^2 + \lambda_i R(m_i)\}$$

where $\|d-f(m)\|_2^2$ comprises a misfit function, d comprises data relating to the acquired reflection signal and transmission signal, $\lambda_i$ is a positive regularization parameter, and $R(m_i)$ is a spatially-variant regularization term.

12. A system as recited in claim 11:
wherein the plurality of transducers are configured such that a first set of two or more transducers are positioned at an opposing spaced-apart orientation from a second set of two or more transducers such that the first set of two or more transducers face the second set of two or more transducers; and wherein the first and second sets of two or more transducers are positioned at spaced-apart locations so as to allow for the tissue medium to be positioned in between the first and second sets of two or more transducers.

* * * * *